US012588902B2

(12) United States Patent
    Mokadam

(10) Patent No.: US 12,588,902 B2
(45) Date of Patent: Mar. 31, 2026

(54) OCCLUSION DEVICES AND METHODS HAVING LATERAL POCKETS OR SLEEVES

(71) Applicant: Ohio State Innovation Foundation, Columbus, OH (US)

(72) Inventor: Nahush Mokadam, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 0 days.

(21) Appl. No.: 18/962,711

(22) Filed: Nov. 27, 2024

(65) Prior Publication Data

US 2025/0143682 A1      May 8, 2025

Related U.S. Application Data

(63) Continuation of application No. PCT/US2024/054146, filed on Nov. 1, 2024.
(Continued)

(51) Int. Cl.
    *A61B 17/00*          (2006.01)
(52) U.S. Cl.
    CPC .................... *A61B 17/0057* (2013.01); *A61B 2017/00477* (2013.01); *A61B 2017/00584* (2013.01);
(Continued)

(58) Field of Classification Search
    CPC .............. A61B 17/1227; A61B 17/122; A61B 2017/00584
    See application file for complete search history.

(56) References Cited

U.S. PATENT DOCUMENTS

| | | | | |
|---|---|---|---|---|
| 643,003 | A | * | 2/1900 | Pollock ................ A61B 17/122 606/120 |
| 2,384,697 | A | * | 9/1945 | Riccardi .............. A61B 17/122 606/120 |

(Continued)

FOREIGN PATENT DOCUMENTS

| | | |
|---|---|---|
| EP | 1694218 A2 | 8/2006 |
| WO | 2005060838 A2 | 7/2005 |

(Continued)

OTHER PUBLICATIONS

International Searching Authority (ISA/US). International Search Report and Written Opinion. PCT Application No. PCT/US2022/042503. Issued on Dec. 28, 2022. 10 pages.
(Continued)

*Primary Examiner* — Alexander J Orkin
(74) *Attorney, Agent, or Firm* — Meunier Carlin & Curfman LLC

(57)          ABSTRACT

An occlusion device for occluding a left atrial appendage extending from a lateral wall of a left atrium of a heart including a first clamping portion and a second clamping portion movably connected to one another and configured for positioning along opposed sides of the left atrial appendage. The first clamping portion and the second clamping portion each may include an inner side configured to face toward the left atrial appendage when the device is in a deployed configuration, an outer side disposed opposite the inner side and configured to face away from the left atrial appendage when the device is in the deployed configuration. A pair of sleeves may be coupled to the outer side of each clamping portion. Each sleeve defines a channel configured to accept a medical tool to facilitate moving the device between an open and closed configuration.

19 Claims, 22 Drawing Sheets

Related U.S. Application Data

(60) Provisional application No. 63/660,694, filed on Jun. 17, 2024, provisional application No. 63/595,830, filed on Nov. 3, 2023.

(52) U.S. Cl.
CPC .............. *A61B 2017/00623* (2013.01); *A61B 2017/00632* (2013.01); *A61B 2017/00646* (2013.01); *A61B 2017/00743* (2013.01)

(56) References Cited

U.S. PATENT DOCUMENTS

| | | | | |
|---|---|---|---|---|
| 2,813,269 | A * | 11/1957 | John ...................... A61B 90/90 | 227/19 |
| 4,919,152 | A * | 4/1990 | Ger ........................ A61B 17/29 | 128/898 |
| 5,074,870 | A | 12/1991 | Von Zeppelin | |
| 5,282,812 | A * | 2/1994 | Suarez, Jr. ........... A61B 17/128 | 206/340 |
| 5,695,505 | A * | 12/1997 | Yoon ...................... A61B 17/12 | 606/151 |
| 6,015,417 | A * | 1/2000 | Reynolds, Jr. ....... A61B 17/122 | 606/151 |
| 6,226,843 | B1 * | 5/2001 | Crainich ............ A61B 17/1227 | 24/546 |
| 7,645,285 | B2 | 1/2010 | Cosgrove et al. | |
| 8,663,245 | B2 | 3/2014 | Francischelli et al. | |
| 8,956,278 | B2 | 2/2015 | Torrie et al. | |
| 9,282,973 | B2 | 3/2016 | Hughett, Sr. et al. | |
| 9,445,820 | B2 * | 9/2016 | Whiting ............... A61B 17/122 | |
| 9,517,178 | B2 | 12/2016 | Chancibot | |
| 10,166,024 | B2 | 1/2019 | Williamson, IV et al. | |
| 10,433,854 | B2 | 10/2019 | Miller et al. | |
| 10,743,885 | B2 | 8/2020 | Menovsky et al. | |
| 10,799,288 | B2 | 10/2020 | Fung et al. | |
| 10,925,615 | B2 | 2/2021 | Deville et al. | |
| 11,389,167 | B2 | 7/2022 | Clark, III et al. | |
| 2004/0147942 | A1 * | 7/2004 | Chao ..................... A61F 5/0086 | 606/153 |
| 2004/0193213 | A1 * | 9/2004 | Aranyi ............... A61B 17/1285 | 606/205 |
| 2005/0149068 | A1 | 7/2005 | Williams et al. | |
| 2005/0149069 | A1 | 7/2005 | Bertolero et al. | |
| 2006/0100646 | A1 * | 5/2006 | Hart ...................... A61B 17/083 | 606/151 |
| 2007/0038233 | A1 * | 2/2007 | Martinez ............ A61B 17/1227 | 606/157 |
| 2007/0149988 | A1 | 6/2007 | Michler et al. | |
| 2008/0039879 | A1 | 2/2008 | Chin et al. | |
| 2008/0208324 | A1 | 8/2008 | Glithero et al. | |
| 2009/0012545 | A1 | 1/2009 | Williamson, IV et al. | |
| 2009/0209986 | A1 | 8/2009 | Stewart et al. | |
| 2010/0145361 | A1 | 6/2010 | Francischelli et al. | |
| 2011/0144662 | A1 * | 6/2011 | McLawhorn ...... A61B 17/1227 | 606/151 |
| 2012/0029557 | A1 | 2/2012 | Prestezog et al. | |
| 2012/0172850 | A1 | 7/2012 | Kappel et al. | |
| 2013/0245653 | A1 * | 9/2013 | Litherland ........... A61B 17/128 | 606/158 |
| 2014/0058411 | A1 * | 2/2014 | Soutorine .............. A61B 17/10 | 606/151 |
| 2015/0223813 | A1 | 8/2015 | Williamson et al. | |
| 2015/0374380 | A1 * | 12/2015 | Miller ................ A61B 17/1227 | 606/142 |
| 2016/0008001 | A1 * | 1/2016 | Winkler ........... A61B 17/12031 | 606/157 |
| 2016/0174981 | A1 * | 6/2016 | Fago ................... A61B 17/1227 | 606/157 |
| 2016/0287387 | A1 * | 10/2016 | Wei ......................... A61F 2/246 | |
| 2018/0036008 | A1 * | 2/2018 | Ramsey .............. A61B 17/083 | |
| 2018/0146965 | A1 * | 5/2018 | Bachar ................ A61B 17/122 | |
| 2019/0231356 | A1 * | 8/2019 | Deville ............. A61B 17/1285 | |
| 2019/0357912 | A1 | 11/2019 | Privitera et al. | |
| 2020/0038024 | A1 * | 2/2020 | Siegenthaler ........ A61B 17/083 | |
| 2021/0007847 | A1 * | 1/2021 | Eggert ................ A61B 17/122 | |
| 2021/0106336 | A1 | 4/2021 | Winkler et al. | |
| 2021/0186511 | A1 | 6/2021 | Shellenberger et al. | |
| 2023/0076759 | A1 * | 3/2023 | Happle ............... A61B 17/122 | |
| 2023/0082963 | A1 | 3/2023 | Mata et al. | |
| 2023/0083170 | A1 | 3/2023 | Biehle et al. | |
| 2023/0083697 | A1 | 3/2023 | Recker et al. | |

FOREIGN PATENT DOCUMENTS

| | | | |
|---|---|---|---|
| WO | 2008020975 A2 | 2/2008 | |
| WO | WO-2023014925 A1 * | 2/2023 | ....... A61B 17/00234 |
| WO | 2023034593 A1 | 3/2023 | |

OTHER PUBLICATIONS

Non-Final Office Action issued in connection with U.S. Appl. No. 18/962,504, dated Feb. 24, 2025, 19 pages.

International Searching Authority (ISA/US). International Search Report and Written Opinion. Issued in PCT Application No. PCT/US2024/054146 on Jan. 17, 2025. 12 pages.

International Searching Authority (ISA/US). International Search Report and Written Opinion. Issued in PCT Application No. PCT/US2024/054149 on Jan. 17, 2025. 11 pages.

European Patent Office. Extended European search report. Issued in EP Application No. 22865622.9. Jun. 3, 2025. 8 pages.

U.S. Patent and Trademark Office. Non-Final Office Action for U.S. Appl. No. 18/962,504, dated Feb. 24, 2025, 13 Pages.

U.S. Patent and Trademark Office. Notice of Allowance and Fees Due for U.S. Appl. No. 18/962,737, dated Mar. 4, 2025, 9 Pages.

U.S. Patent and Trademark Office. Final office action. Issued in U.S. Appl. No. 18/962,504, filed Jun. 5, 2025. 23 pages.

* cited by examiner

1000

1000

1000

1000

SECTION B-B

3600

3500

2000

3600

3500

2000

2000

2000

OCCLUSION DEVICES AND METHODS HAVING LATERAL POCKETS OR SLEEVES

CROSS-REFERENCE TO RELATED APPLICATIONS

This application is a continuation of International Application PCT/US2024/054146, filed Nov. 1, 2024, which claims priority to U.S. Provisional Patent Application No. 63/595,830 filed Nov. 3, 2023, and U.S. Provisional Patent Application No. 63/660,694 filed Jun. 17, 2024, each of which are incorporated herein by reference in their entirety.

FIELD OF THE DISCLOSURE

The present disclosure relates generally to devices and methods for occluding a hollow tissue structure of a living subject, including but not limited to, devices and methods for occluding a left atrial appendage of a subject's heart.

BACKGROUND OF THE DISCLOSURE

In various instances, a hollow tissue structure of a living subject (i.e., a human or an animal) may be occluded for different medical purposes. For example, occlusion may be used to reduce pressure on aneurysms, restrict a hemorrhage, reduce blood supply to tumors, clamp a bowel, or occlude a variety of vascular structures. In one common example, a left atrial appendage of a subject's heart often may be occluded, either surgically or percutaneously, for subjects with atrial fibrillation. The left atrial appendage is a hollow tissue structure extending from the lateral wall of the left atrium of the heart. During normal heart function, the left atrial appendage typically contracts along with the remainder of the left atrium, thereby moving blood throughout the hollow space of the left atrial appendage. However, during atrial fibrillation, the left atrial appendage may fail to contract, such that blood may be allowed to pool within the appendage and become stagnated, which may lead to thrombus or clot formation. Such clots may be released from the left atrial appendage into the left atrium and then into the bloodstream, potentially resulting in an obstruction in the subject's brain or other vascular structures and thus increasing the risk of stroke. Various techniques may be used to prevent clots from forming within the left atrial appendage and then being released into the patient's bloodstream.

Occlusion of the left atrial appendage is one common approach for decreasing the risk of stroke caused by clots formed in the appendage. Left atrial appendage occlusion typically may be performed to prevent blood from entering the appendage and forming clots therein, while also preventing any clots already formed within the appendage from entering the bloodstream. Various types of techniques may be performed, either surgically or percutaneously, to occlude the left atrial appendage of a subject, such as those with atrial fibrillation. Certain techniques use an occlusion device that is formed as a clip, a clamp, or similar structure, which devices are intended to be implanted near the base of the left atrial appendage to isolate the appendage from the subject's blood circulatory system. Examples of this type of occlusion device include the AtriClip device and the AtriClip PRO-V device, both manufactured by AtriCure, Inc. Although such occlusion devices may be suitable in some instances, they may present limitations in certain instances. For example, the use of such occlusion devices may result in incomplete occlusion of the left atrial appendage in certain subjects, which may be attributed to the shape of portions of the occlusion device that engage the left atrial appendage near the base thereof. As discussed further below, the base of the left atrial appendage may have a linear, or substantially linear, shape when the heart is elevated out the subject's chest for implantation of the occlusion device, but the base may assume a non-linear shape when the heart is in situ. The relevant portions of the occlusion device may not be adapted to accommodate this non-linear shape of the base, and thus implantation of the occlusion device may result in incomplete occlusion of the left atrial appendage, leaving a residual stump of the appendage which may lead to thrombus formation and thus subsequent risk of stroke. Furthermore, existing devices may require specialized surgical tools and equipment, such as screws, holders, cross clamps, wires, knobs, and handles (e.g., on the deployment device associated with the AtriClip device). These specialized tools increase the complexity and manufacturing costs of existing devices.

A need therefore exists for improved devices and methods for occluding a hollow tissue structure of a living subject (e.g., a left atrial appendage of a subject's heart), which may overcome one or more of the above-mentioned limitations associated with existing techniques for left atrial appendage occlusion.

SUMMARY OF THE DISCLOSURE

According to one aspect, an occlusion device for occluding a hollow tissue structure of a living subject (e.g., a left atrial appendage extending from a lateral wall of a left atrium of a heart) is disclosed, the occlusion device including: a first clamping portion configured for positioning along a first side of the left atrial appendage; and a second clamping portion movably connected to the first clamping portion on a first end of the occlusion device and configured for positioning along an opposite second side of the left atrial appendage while the first clamping portion is positioned along the first side. The first clamping portion and the second clamping portion each include: an inner side configured to face toward the left atrial appendage when the occlusion device is in a deployed configuration; an outer side disposed opposite the inner side and configured to face away from the left atrial appendage when the occlusion device is in the deployed configuration; and at least one sleeve, including a first sleeve coupled to (e.g., integrally coupled to) and extending from the outer side of the first clamping portion, the first sleeve defining a first opening on a first end of the first sleeve and a first channel extending from the first opening towards a second end of the first sleeve.

In another aspect, a method for occluding a hollow tissue structure of a living subject (e.g., a left atrial appendage extending from a lateral wall of a left atrium of a heart) is disclosed, the method including: causing an occlusion device to transition from a closed configuration to an open configuration, wherein the occlusion device includes a first clamping portion and a second clamping portion movably connected to the first clamping portion, and wherein the first clamping portion and the second clamping portion each include: an inner side; an outer side disposed opposite the inner side; and a first sleeve coupled to (e.g., integrally coupled to) and extending from the outer side of the first clamping portion and a second sleeve coupled to (e.g., integrally coupled to) and extending from the outer side of the second clamping portion; positioning the occlusion device relative to the left atrial appendage such that the first clamping portion is positioned along a first side of the left atrial appendage and the second clamping portion is positioned along an opposite second side of the left atrial appendage; and causing the occlusion device to transition from the open configuration to a deployed configuration in which the occlusion device occludes the left atrial appendage, wherein, when the occlusion device is in the deployed configuration, the inner sides of the first clamping portion and the second clamping portion each face toward the left atrial appendage, the outer sides of the first clamping portion and the second clamping portion each face away from the left atrial appendage.

In another aspect, a system is disclosed, the system including: an occlusion device disclosed herein; and a pair of forceps having opposing tips, wherein the first sleeve of the device is configured to accept a tip of the forceps.

In another aspect, an occlusion device for occluding a hollow tissue structure of a living subject is disclosed. The occlusion device includes a first inner arm, a second inner arm, a first outer arm, and a second outer arm. The first inner arm extends from a first end to a second end along a first direction parallel to a curved longitudinal axis of the occlusion device. The second inner arm extends from a first end to a second end along the first direction. The second inner arm is adjacent to first inner arm in a second direction that is perpendicular to the curved longitudinal axis. The first outer arm extends from a first end to a second end along the first direction. The first end of the first outer arm is coupled to the second end of the first inner arm to define a first distal extent at a distal end of the occlusion device. The first outer arm is spaced apart from the first inner arm in the second direction on a side of the first inner arm opposite of the second inner arm. The second outer arm extends from a first end to a second end along the first direction. The first end of the second outer arm is coupled to the second end of the second inner arm to define a second distal extent at the distal end of the occlusion device. The second outer arm is spaced apart from the second inner arm in the second direction on a side of the second inner arm opposite of the first inner arm. The second end of the first outer arm is coupled to the second end of the second outer arm at a proximal end of the occlusion device via a hinge portion. Each of the first outer arm, the second outer arm, and the hinge portion define an opening within which the first inner arm and the second inner arm are disposed.

In another aspect, a method of using an occlusion device is disclosed. The method includes: (1) providing an occlusion device including: a first inner arm extending from a first end to a second end along a first direction parallel to a curved longitudinal axis of the occlusion device; a second inner arm extending from a first end to a second end along the first direction, the second inner arm being adjacent to first inner arm in a second direction that is perpendicular to the curved longitudinal axis; a first outer arm extending from a first end to a second end along the first direction, the first end of the first outer arm being coupled to the second end of the first inner arm to define a first distal extent at a distal end of the occlusion device, wherein the first outer arm is spaced apart from the first inner arm in the second direction on a side of the first inner arm opposite of the second inner arm; and a second outer arm extending from a first end to a second end along the first direction, the first end of the second outer arm being coupled to the second end of the second inner arm to define a second distal extent at the distal end of the occlusion device, wherein the second outer arm is spaced apart from the second inner arm in the second direction on a side of the second inner arm opposite of the first inner arm; wherein the second end of the first outer arm is coupled to the second end of the second outer arm at a proximal end of the occlusion device via a hinge portion, and wherein each of the first outer arm, the second outer arm, and the hinge portion define an opening within which the first inner arm and the second inner arm are disposed. The method further includes (2) coupling a first arm of a medical instrument to at least a first suture hole defined by and extending at least partially through the first distal extent of the occlusion device. The method further includes (3) coupling a second arm of the medical instrument to at least a second suture hole defined by and extending at least partially through the first distal extent of the occlusion device, wherein the second arm of the medical instrument is hingably coupled to the first arm of the medical instrument. The method further includes (4) moving the occlusion device from (i) a closed configuration wherein the second end of the first inner arm is spaced apart from the second end of the second inner arm by a first lateral distance, to (ii) an open configuration, wherein the second end of the first inner arm is spaced apart from the second end of the second inner arm by a second lateral distance that is greater than the first lateral distance.

In another aspect, a method for occluding a hollow tissue structure is disclosed. The method includes (1) moving an occlusion device from a closed configuration to an open configuration, wherein the occlusion device includes: a first inner arm extending from a first end to a second end along a first direction parallel to a curved longitudinal axis of the occlusion device, the first inner arm having an inner surface and an outer surface opposite the inner surface; a second inner arm extending from a first end to a second end along the first direction, the second inner arm having an inner surface and an outer surface opposite the inner surface, wherein the second inner arm is adjacent to first inner arm in a second direction that is perpendicular to the curved longitudinal axis; a first outer arm extending from a first end to a second end along the first direction, the first end of the first outer arm being coupled to the second end of the first inner arm to define a first distal extent at a distal end of the occlusion device, wherein the first outer arm is spaced apart from the first inner arm in the second direction on a side of the first inner arm opposite of the second inner arm; and a second outer arm extending from a first end to a second end along the first direction, the first end of the second outer arm being coupled to the second end of the second inner arm to define a second distal extent at the distal end of the occlusion device, wherein the second outer arm is spaced apart from the second inner arm in the second direction on a side of the second inner arm opposite of the first inner arm, wherein the second end of the first outer arm is coupled to the second end of the second outer arm at a proximal end of the occlusion device via a hinge portion, and wherein each of the first outer arm, the second outer arm, and the hinge portion define an opening within which the first inner arm and the second inner arm are disposed, and wherein the occlusion device and the curved longitudinal axis thereof defines a concave side of the occlusion device and a convex side of the occlusion device opposite from the concave side. The method further includes (2) positioning the occlusion device relative to the hollow tissue structure such that the first inner arm is positioned along a first side of the hollow tissue structure and the second inner arm is positioned along an opposite second side of the hollow tissue structure. The method further includes (3) causing the occlusion device to transition from the open configuration toward the closed configuration in which the occlusion device occludes the hollow tissue structure, wherein, when the occlusion device is in the closed configuration, the inner surface of the first inner arm and the inner surface of the second inner arm each face toward the hollow tissue structure.

These and other aspects and improvements of the present disclosure will become apparent to one of ordinary skill in the art upon review of the following detailed description when taken in conjunction with the several drawings and the appended claims.

Figures 5A, 5B, 5C, 5D, 5E, 5F:
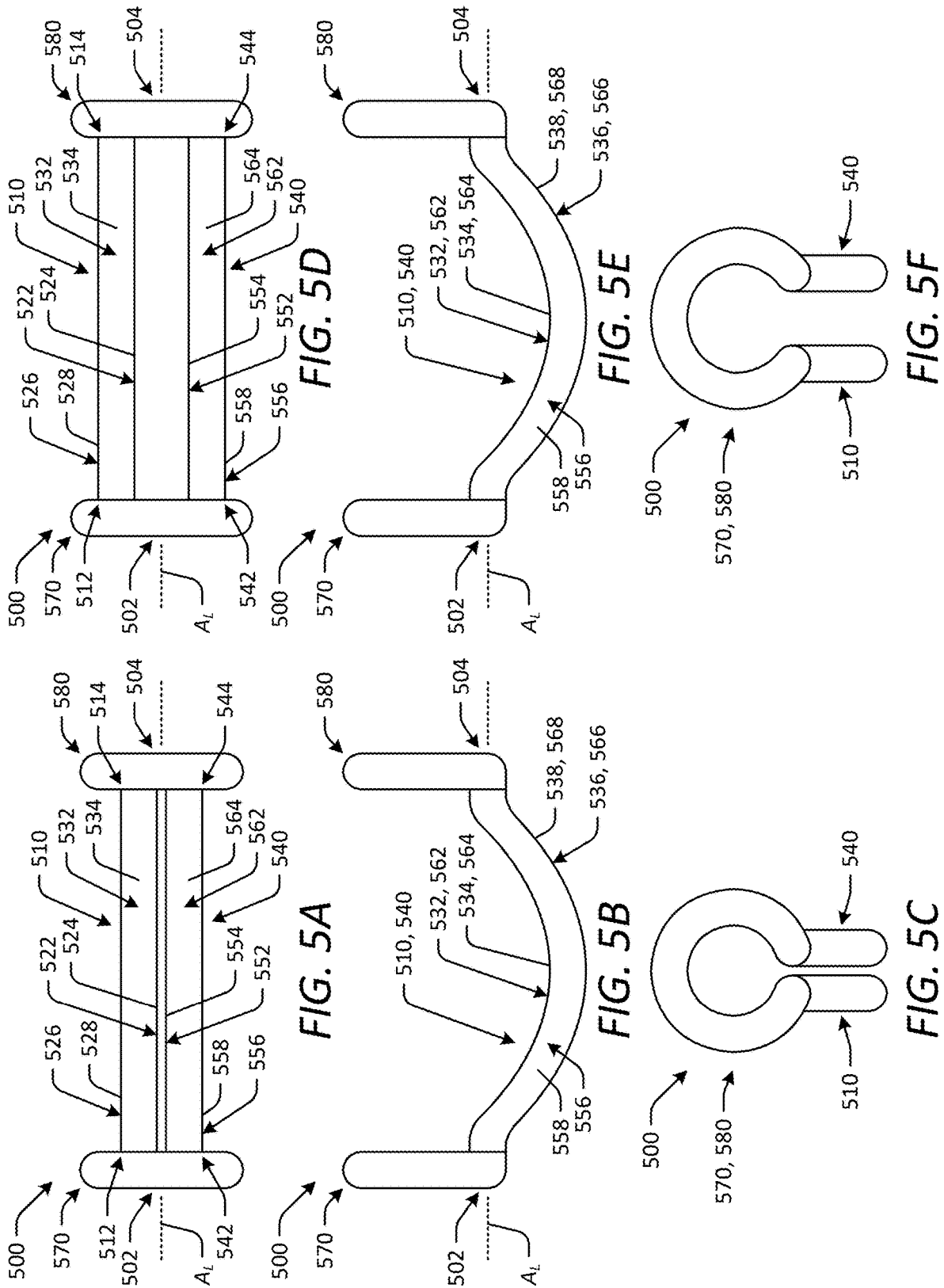
FIG. 5A is a top view of an example occlusion device in accordance with one or more embodiments of the disclosure, showing the occlusion device in a closed configuration.
FIG. 5B is a side view of the occlusion device of FIG. 5A in the closed configuration.
FIG. 5C is an end view of the occlusion device of FIG. 5A in the closed configuration.
FIG. 5D is a top view of the occlusion device of FIG. 5A in an open configuration.
FIG. 5E is a side view of the occlusion device

6 of FIG. 5A in the open configuration. FIG. 5F is an end view of the occlusion device of FIG. 5A in the open configuration.

Figures 6A, 6B, 6C, 6D, 6E, 6F:
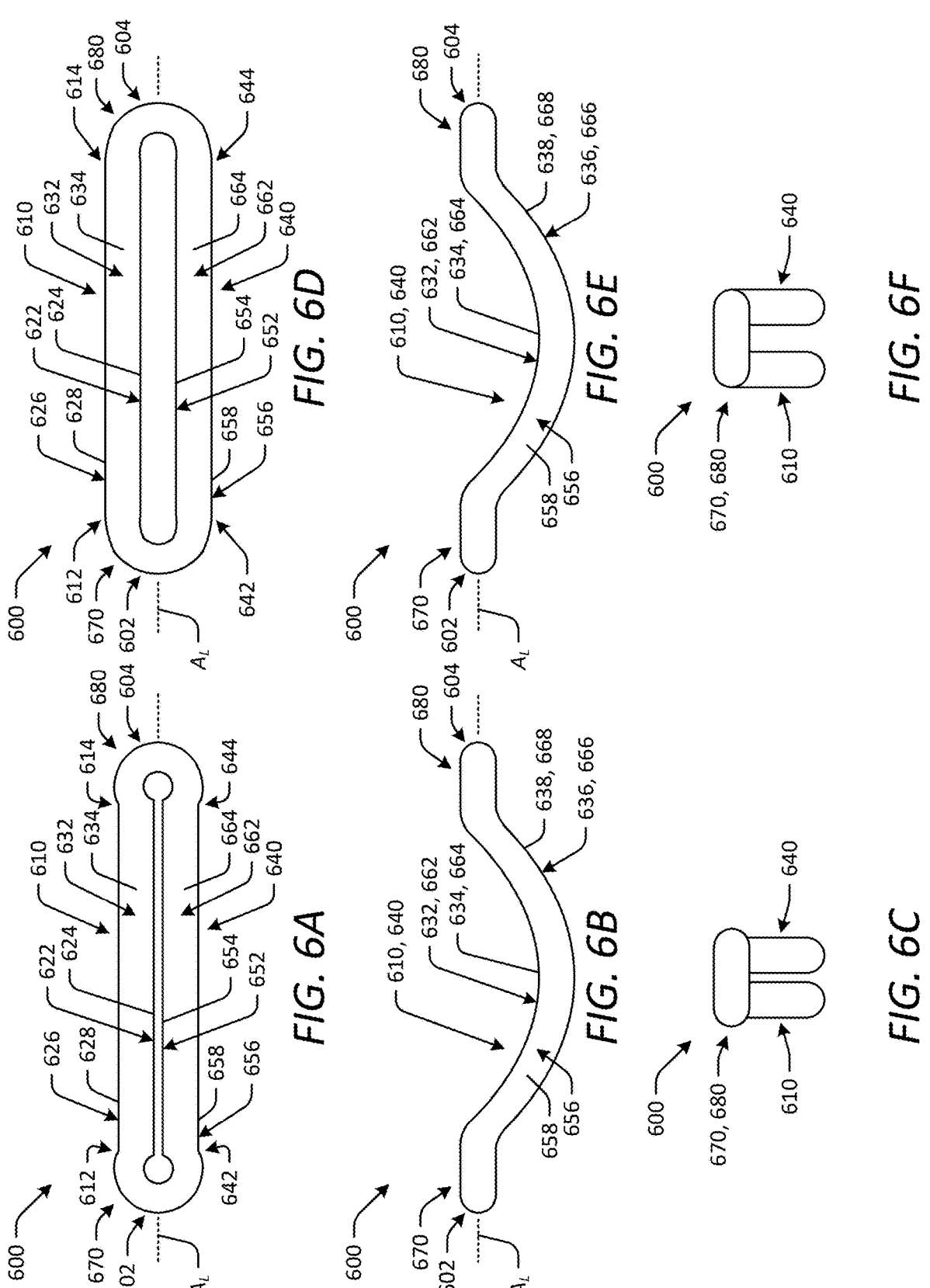

FIG. 6A is a top view of an example occlusion device in accordance with one or more embodiments of the disclosure, showing the occlusion device in a closed configuration. FIG. 6B is a side view of the occlusion device of FIG. 6A in the closed configuration. FIG. 6C is an end view of the occlusion device of FIG. 6A in the closed configuration. FIG. 6D is a top view of the occlusion device of FIG. 6A in an open configuration. FIG. 6E is a side view of the occlusion device of FIG. 6A in the open configuration. FIG. 6F is an end view of the occlusion device of FIG. 6A in the open configuration.

Figures 7A, 7B, 7C, 7D:
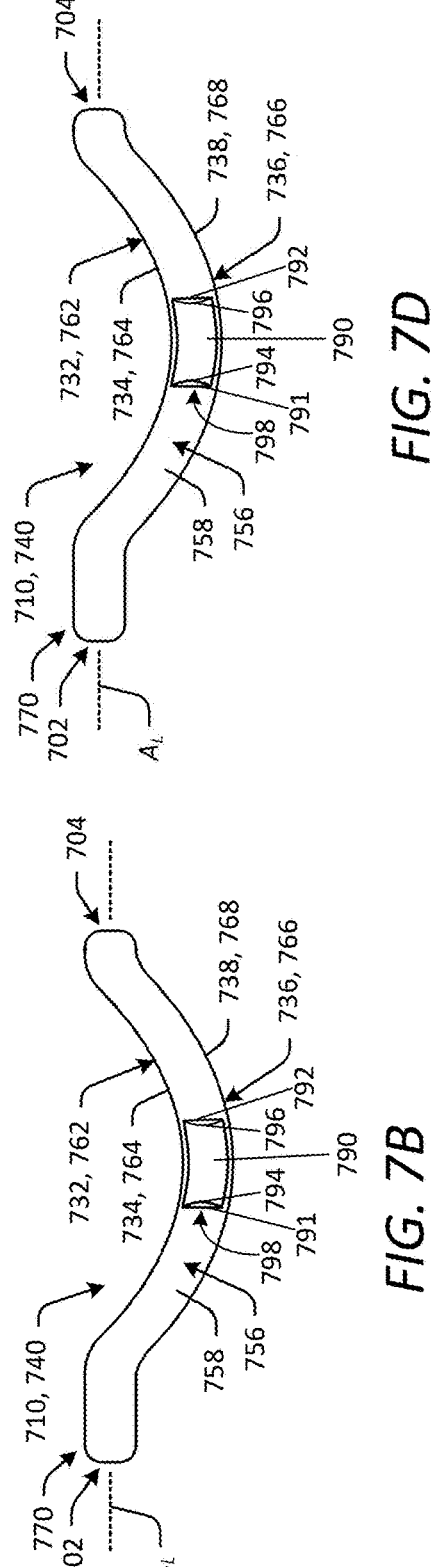

FIG. 7A is a top view of an example occlusion device in accordance with one or more embodiments of the disclosure, showing the occlusion device in a closed configuration. FIG. 7B is a side view of the occlusion device of FIG. 7A in the closed configuration. FIG. 7C is a top view of the occlusion device of FIG. 7A in an open configuration. FIG. 7D is a side view of the occlusion device of FIG. 7A in the open configuration.

Figures 8, 9:
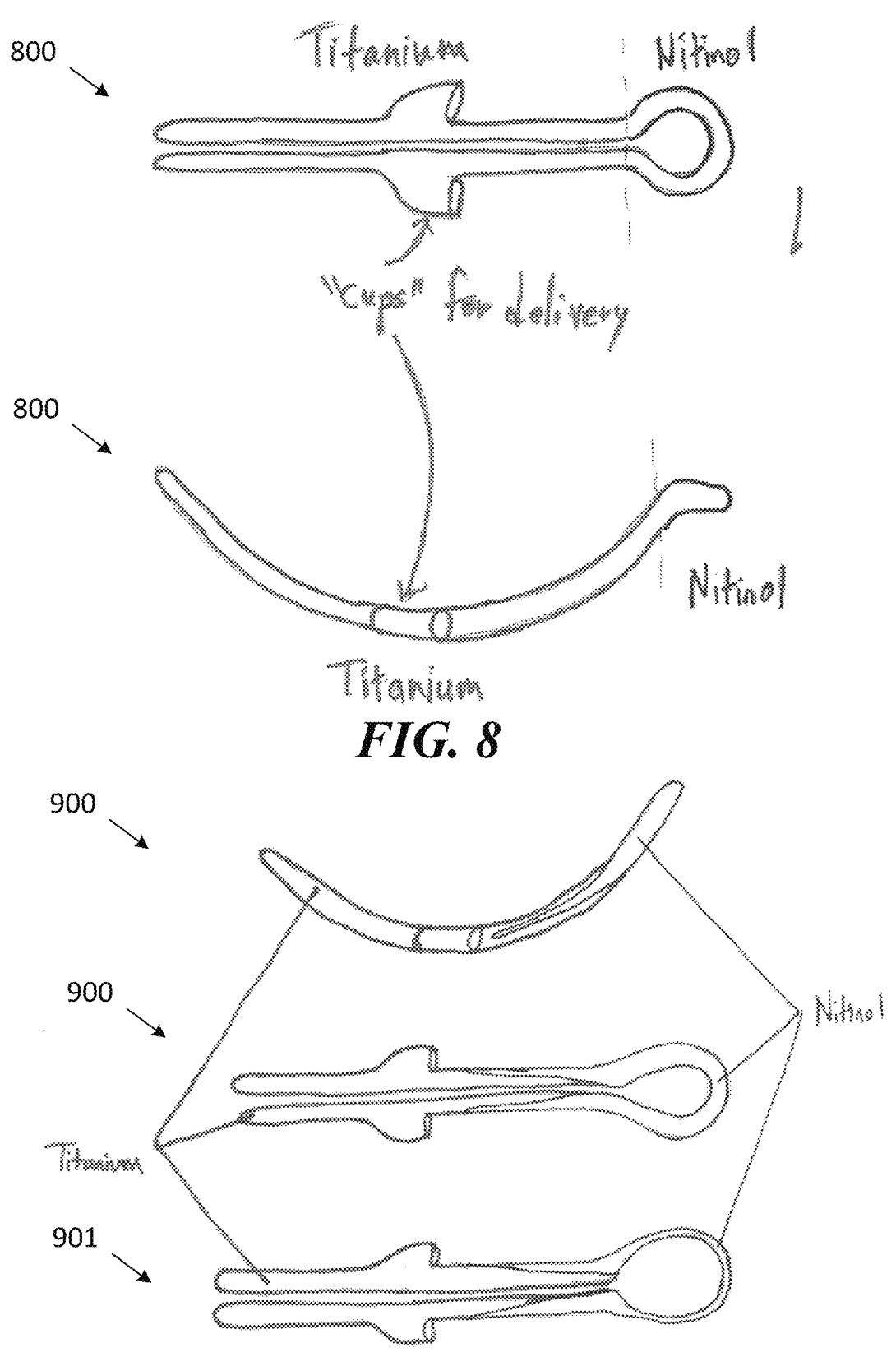
Figure 10A:
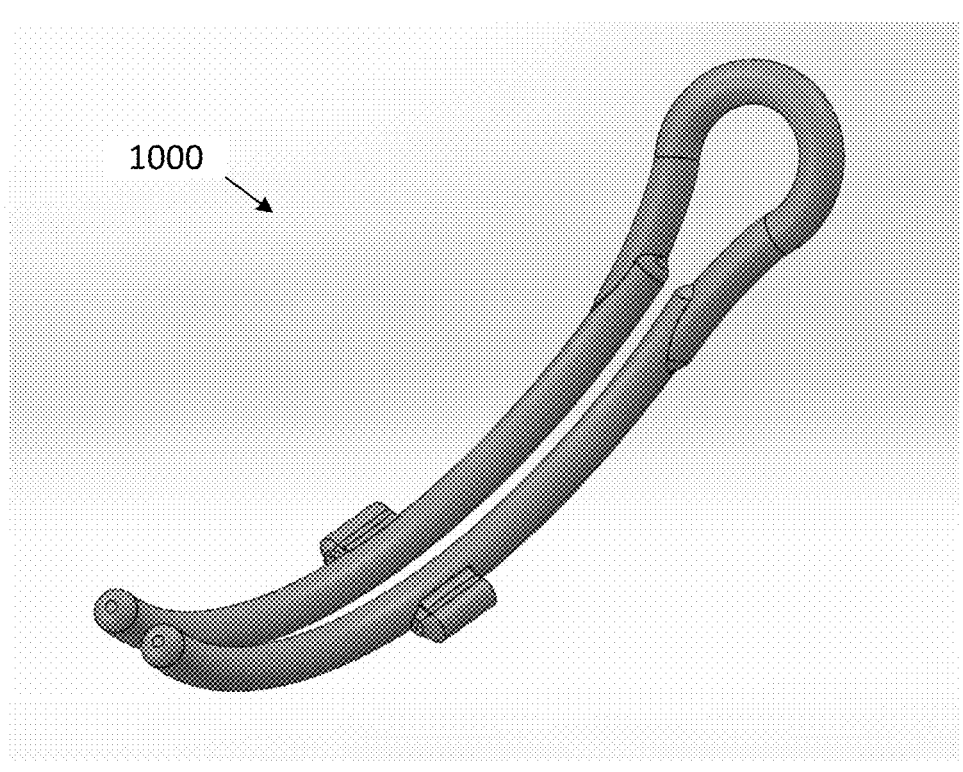
Figure 10B:
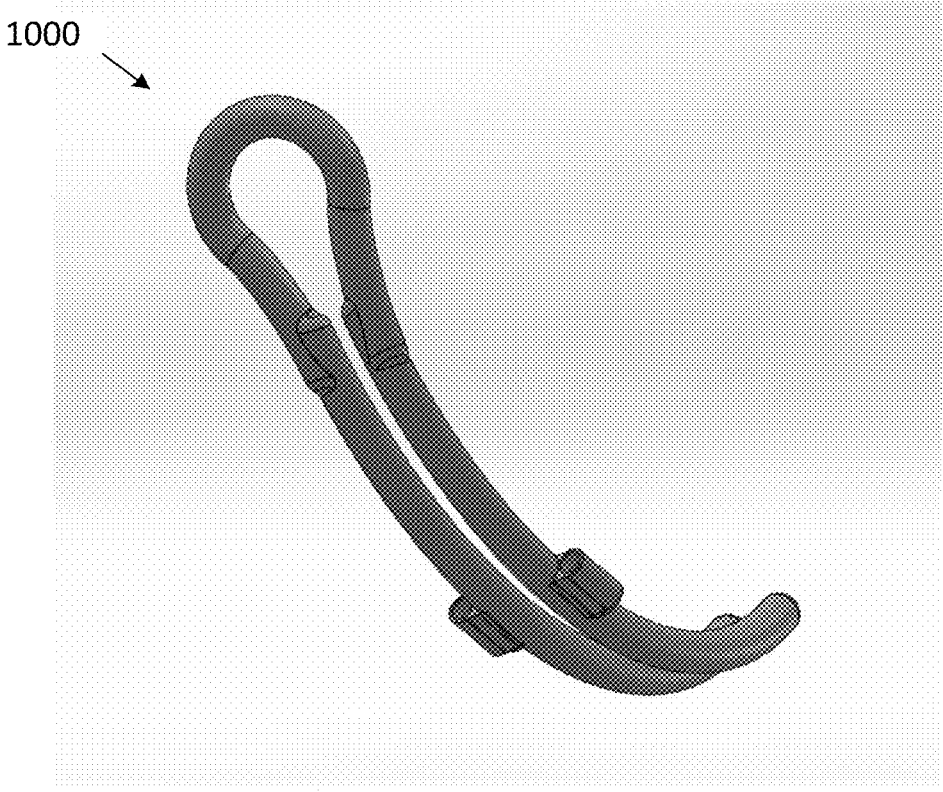
Figure 10C:
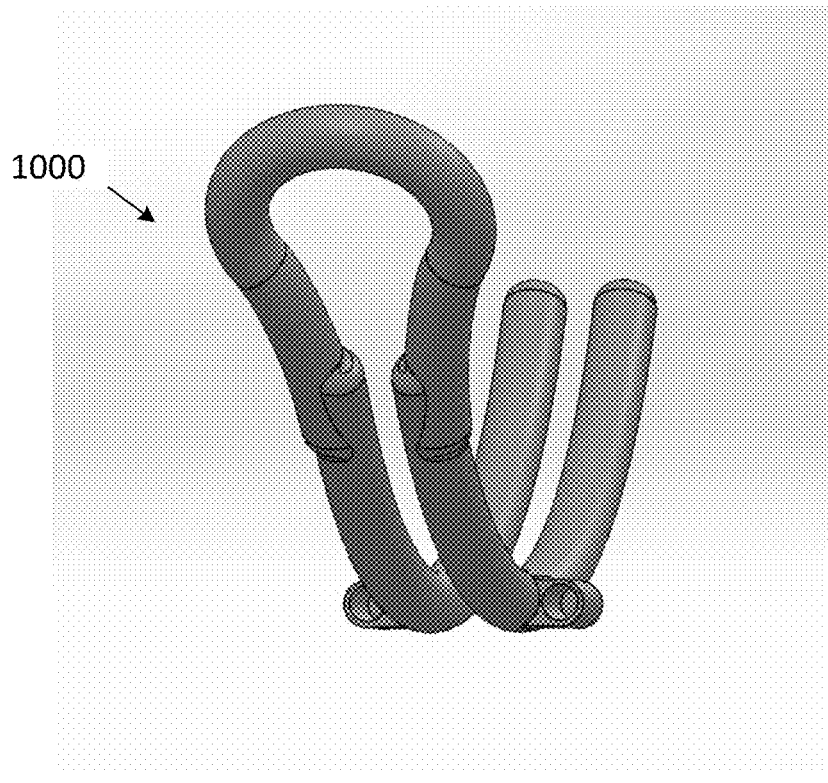
Figure 10D:
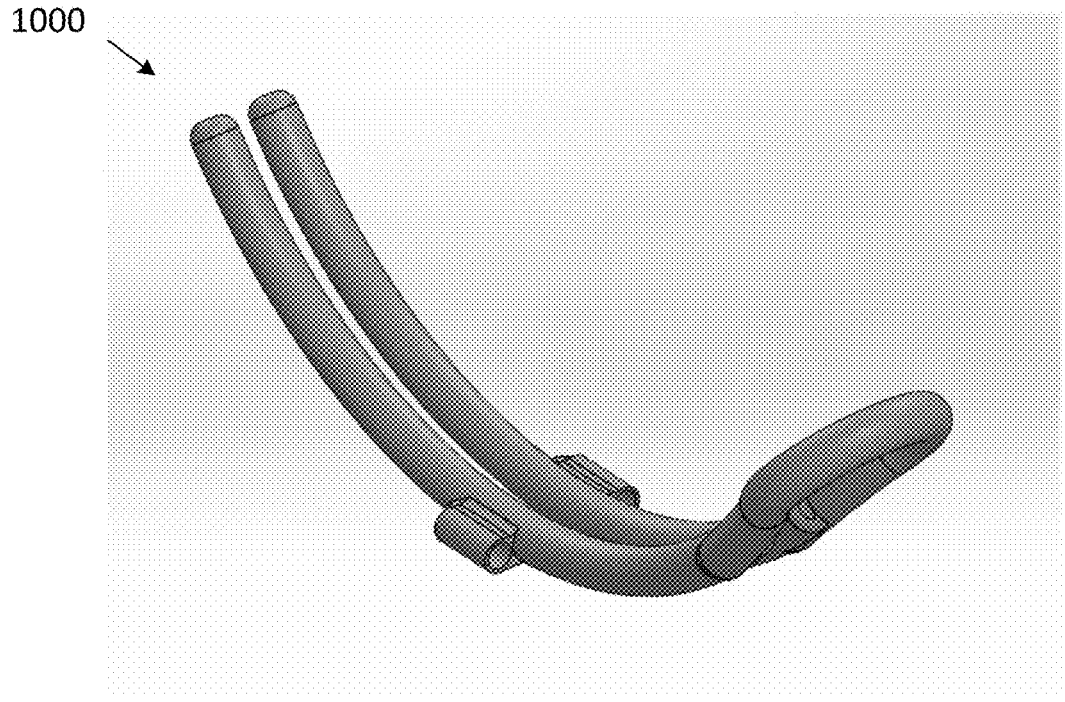

FIG. 8 is a top and side view of an example occlusion device in accordance with one or more embodiments of the disclosure.

FIG. 9 is a top and side view of example occlusion devices in accordance with one or more embodiments of the disclosure.

FIGS. 10A-10D are isometric views of an example occlusion device in accordance with one or more embodiments of the disclosure.

Figure 11A:
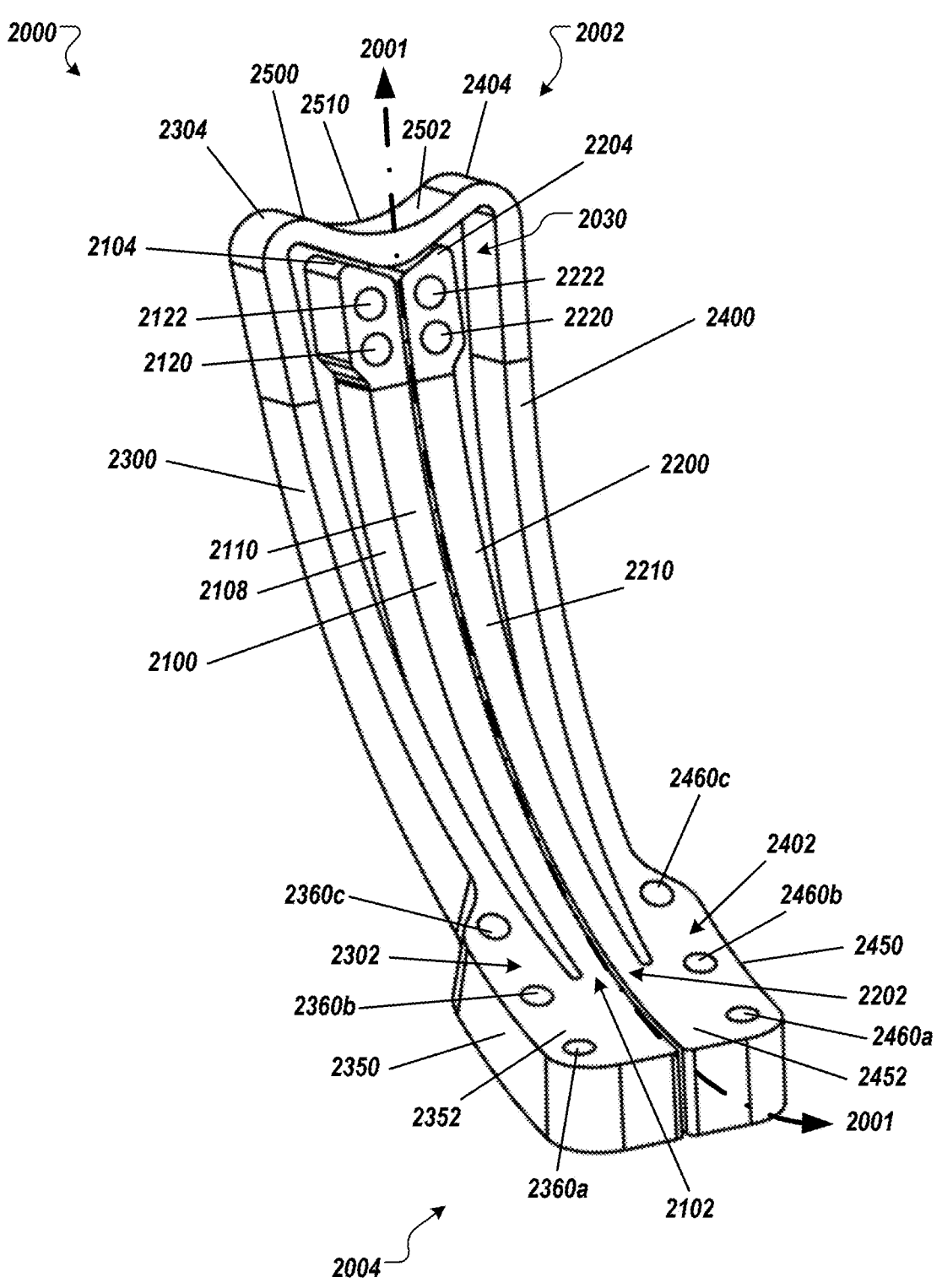
Figures 11B, 11C:
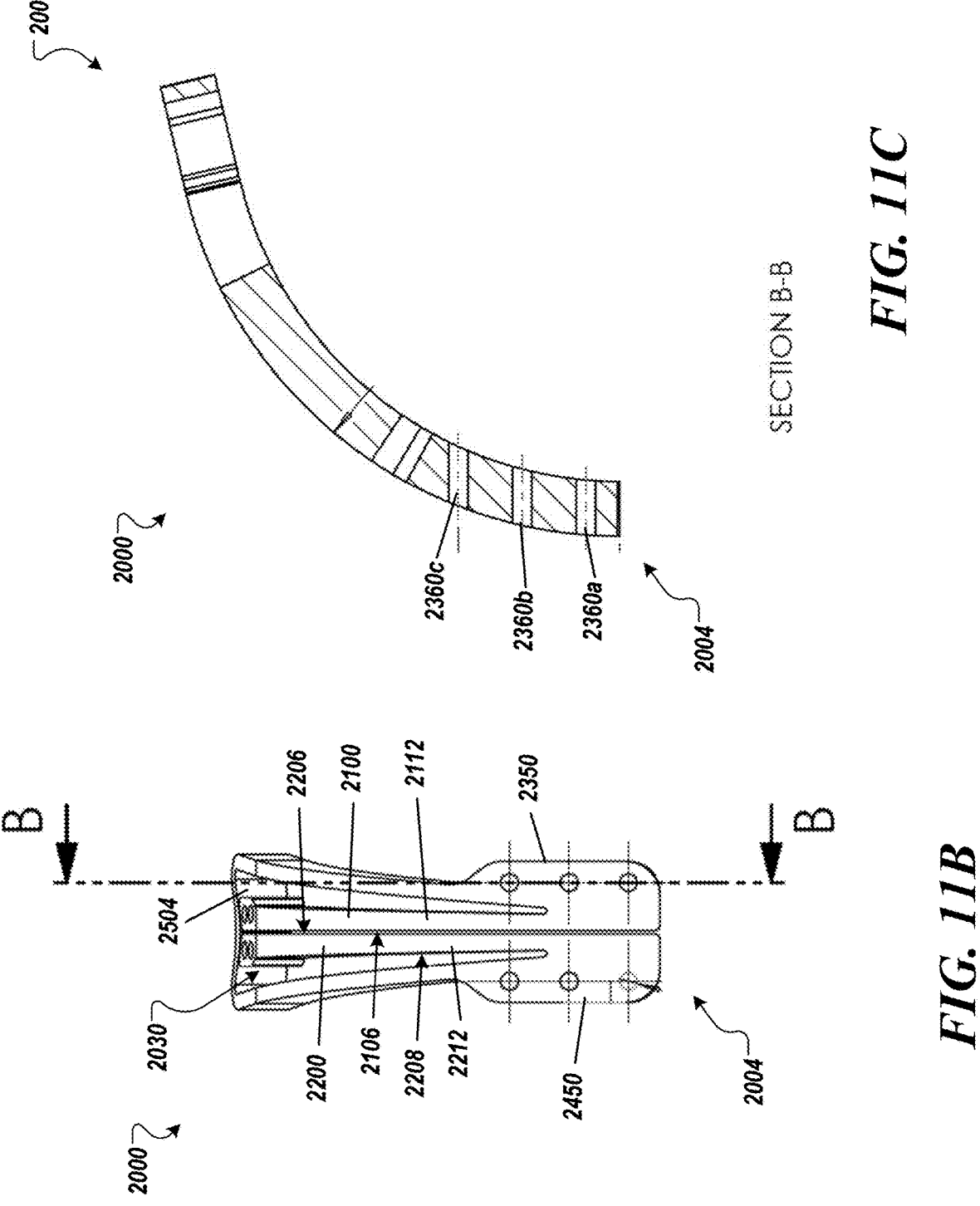

FIG. 11A shows an isometric view of an example occlusion device in accordance with one or more embodiments of the disclosure. FIG. 11B shows a view of the occlusion device of FIG. 11A along the curved longitudinal axis on the convex side. FIG. 11C shows a cross-sectional view of the occlusion device taken along line B-B in FIG. 11B.

Figure 12A:
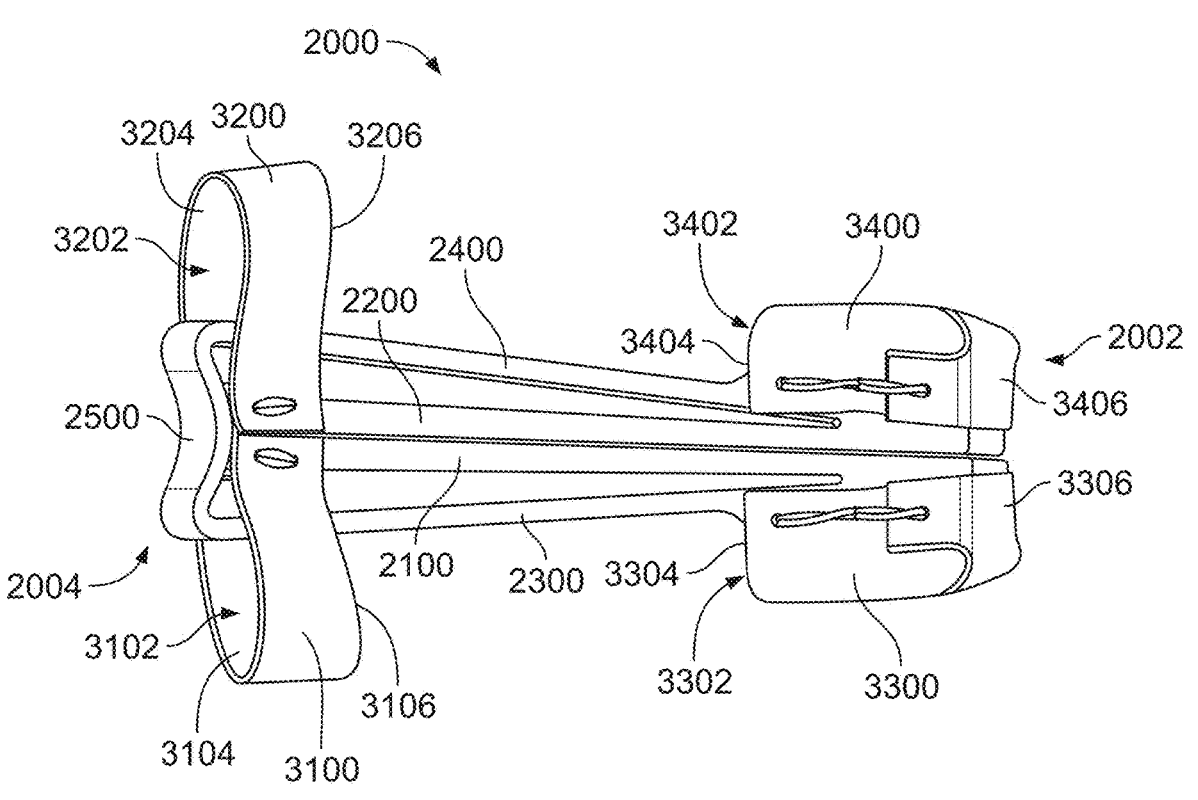
Figure 12B:
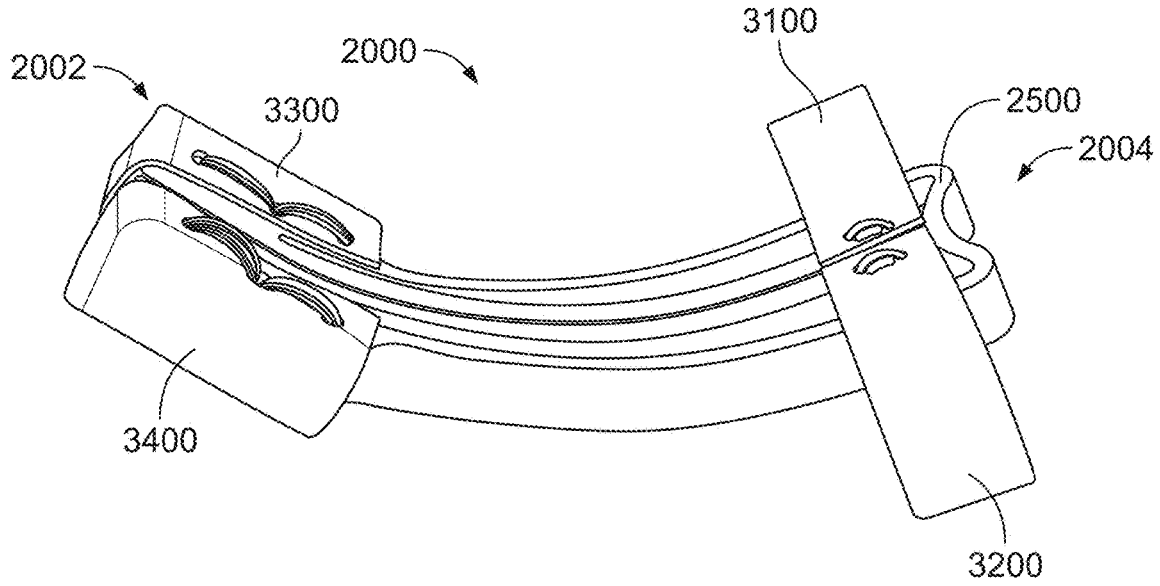
Figure 12C:
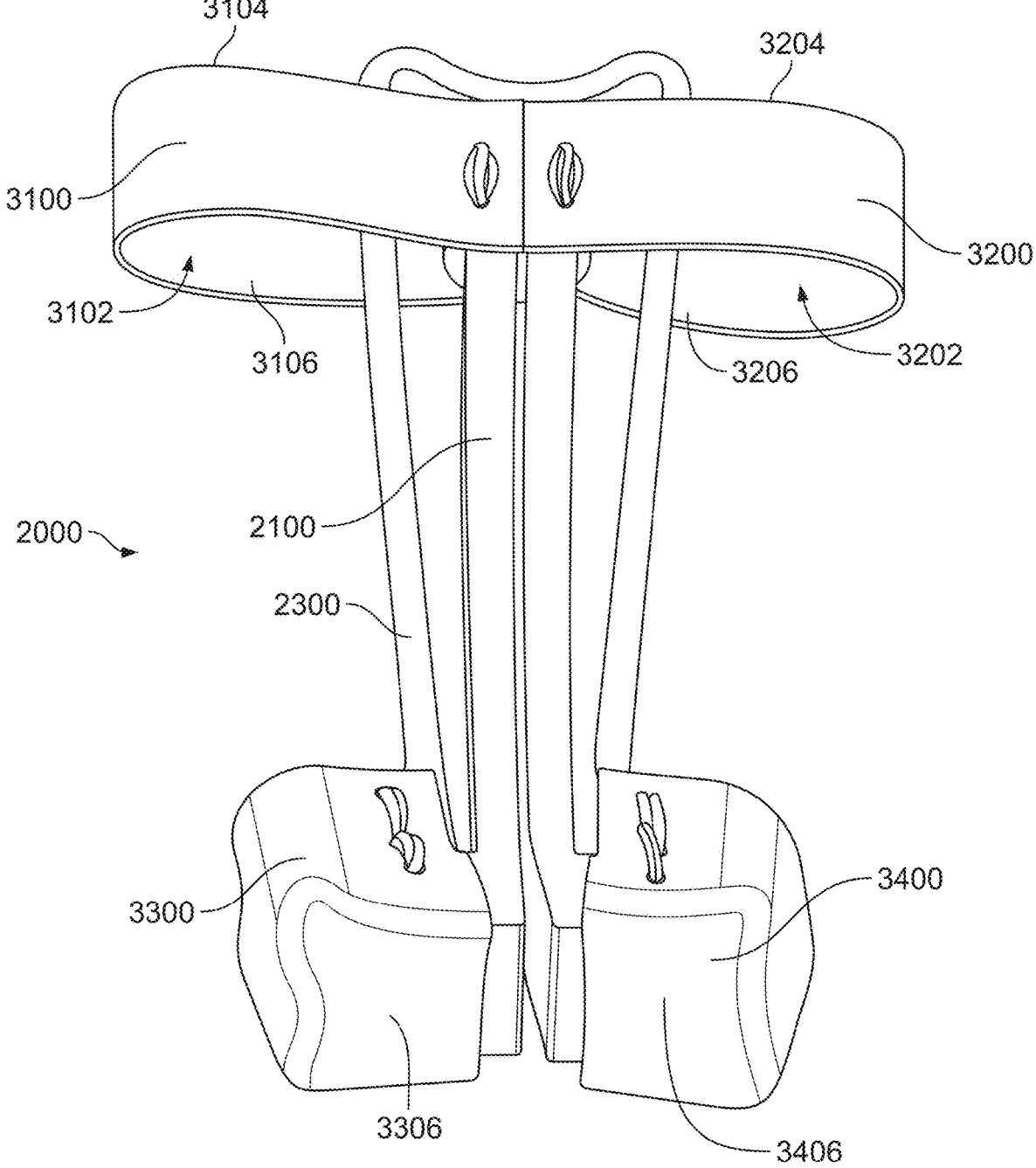

FIG. 12A shows a top view of the occlusion device of FIG. 11A with sleeves coupled to the device, according to one implementation. FIG. 12B shows another view of the occlusion device with sleeves of FIG. 12A. FIG. 12C shows another view of the occlusion device with sleeves of FIG. 12A.

Figure 13A:
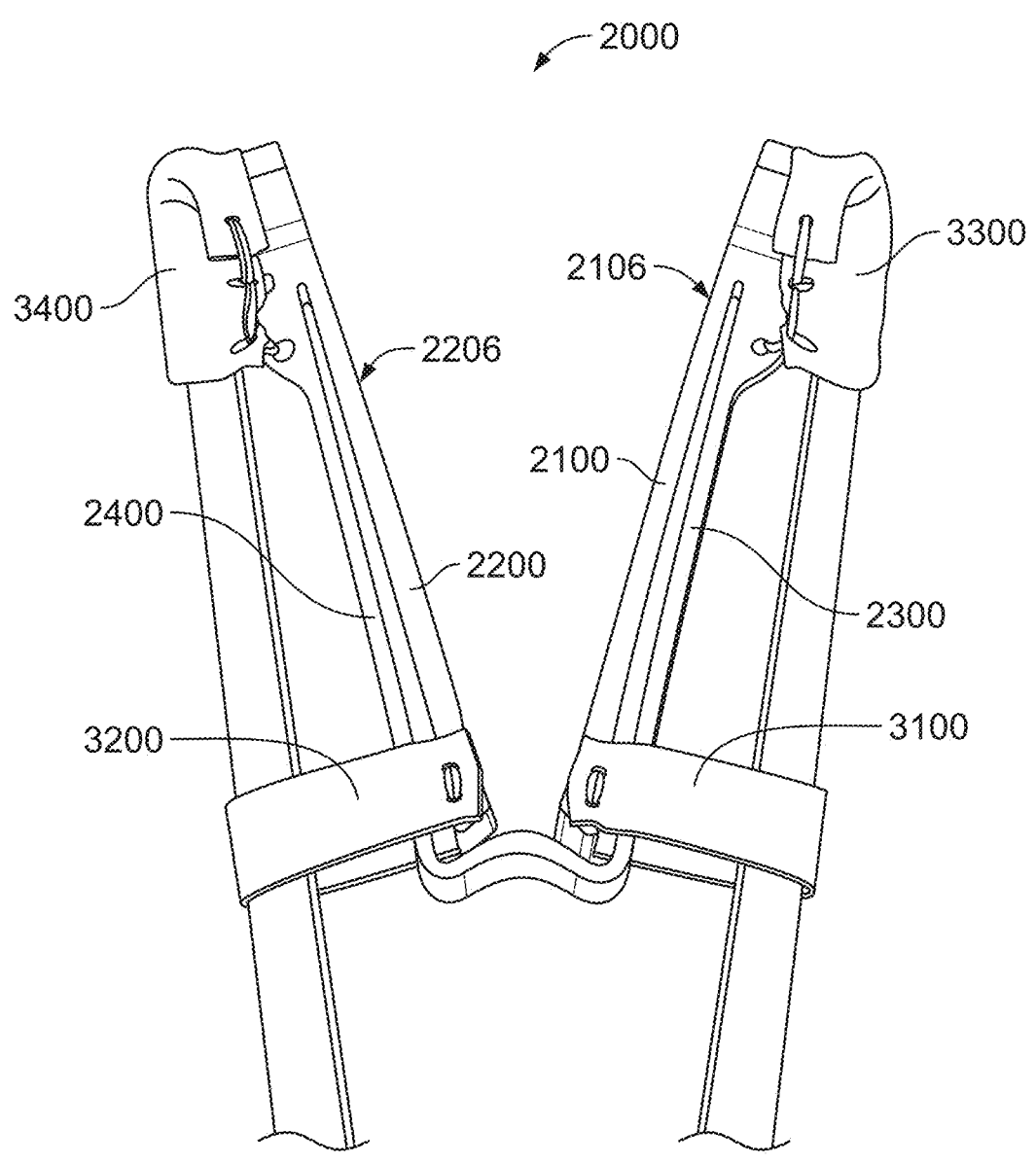

FIG. 13A shows an example occlusion device with sleeves engaged with a medical instrument to expand the occlusion device into an open configuration, according to one implementation.

Figure 13B:
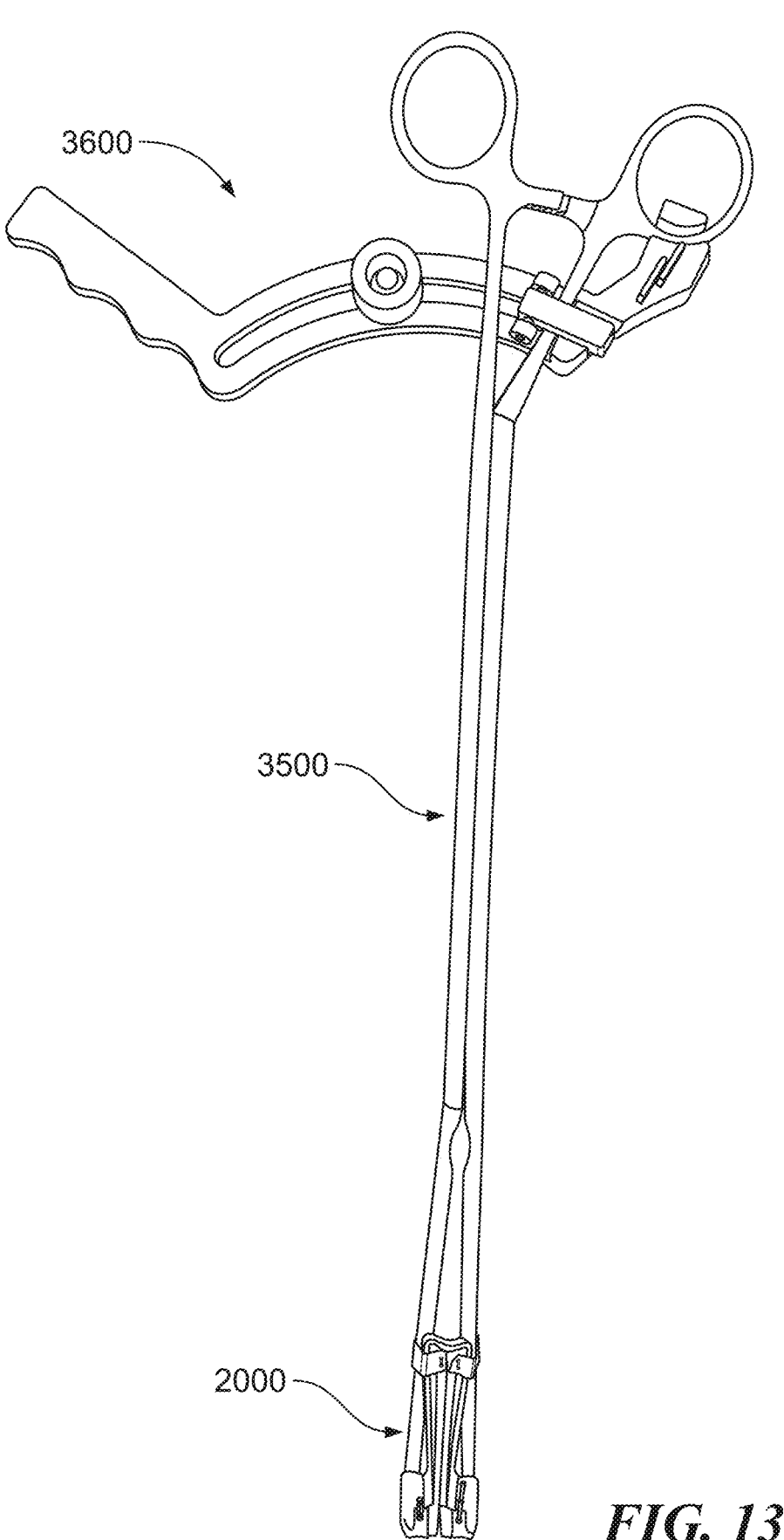

FIG. 13B shows an example occlusion device with sleeves in the closed configuration, the occlusion device engaged with a medical instrument that is engaged with a retention device, according to one implementation.

Figure 13C:
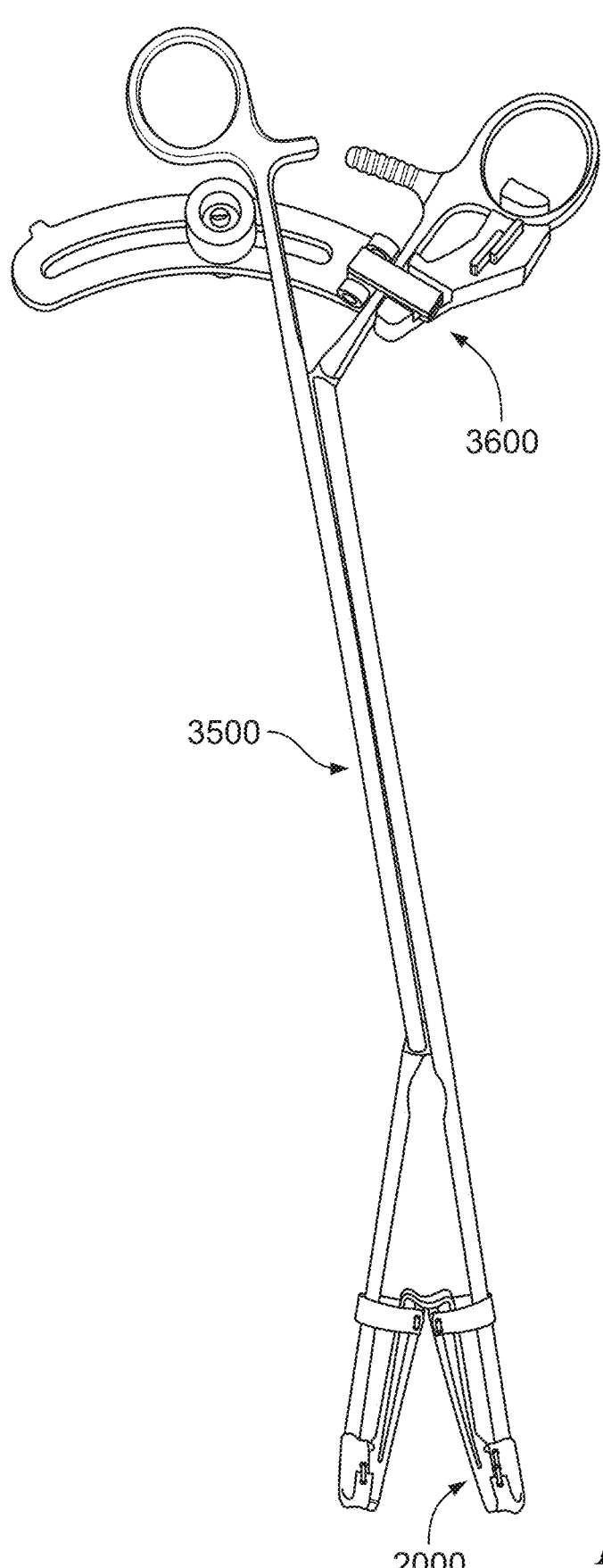

FIG. 13C shows an example occlusion device with sleeves in the open configuration, the occlusion device engaged with a medical instrument that is engaged with a retention device, according to one implementation.

Figure 14A:
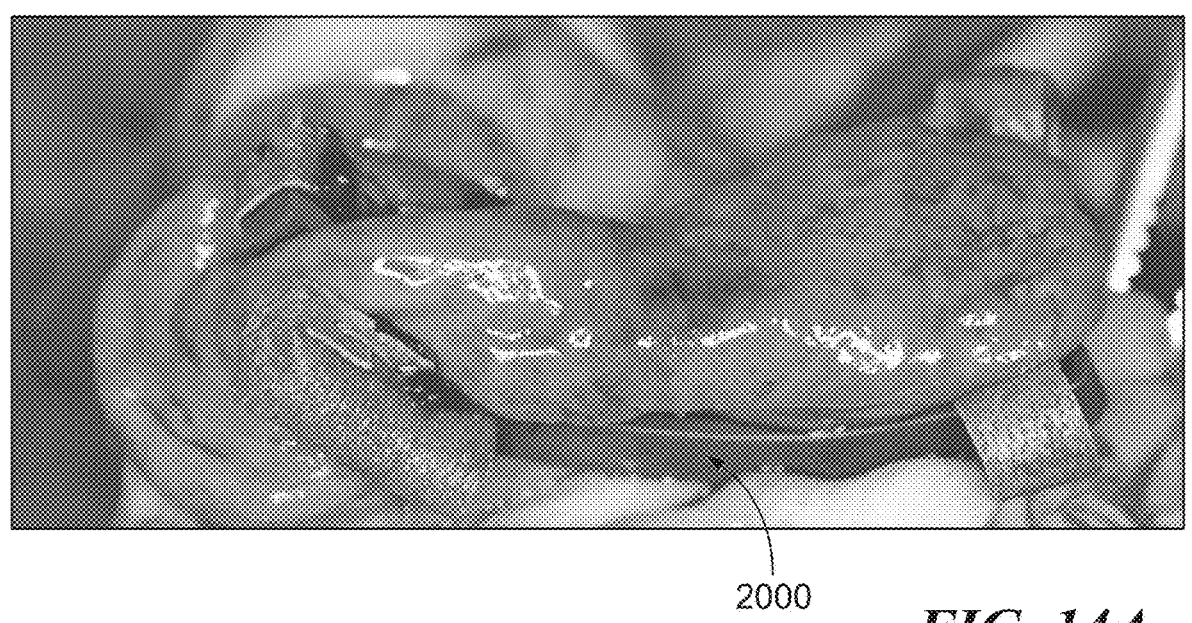
Figure 14B:
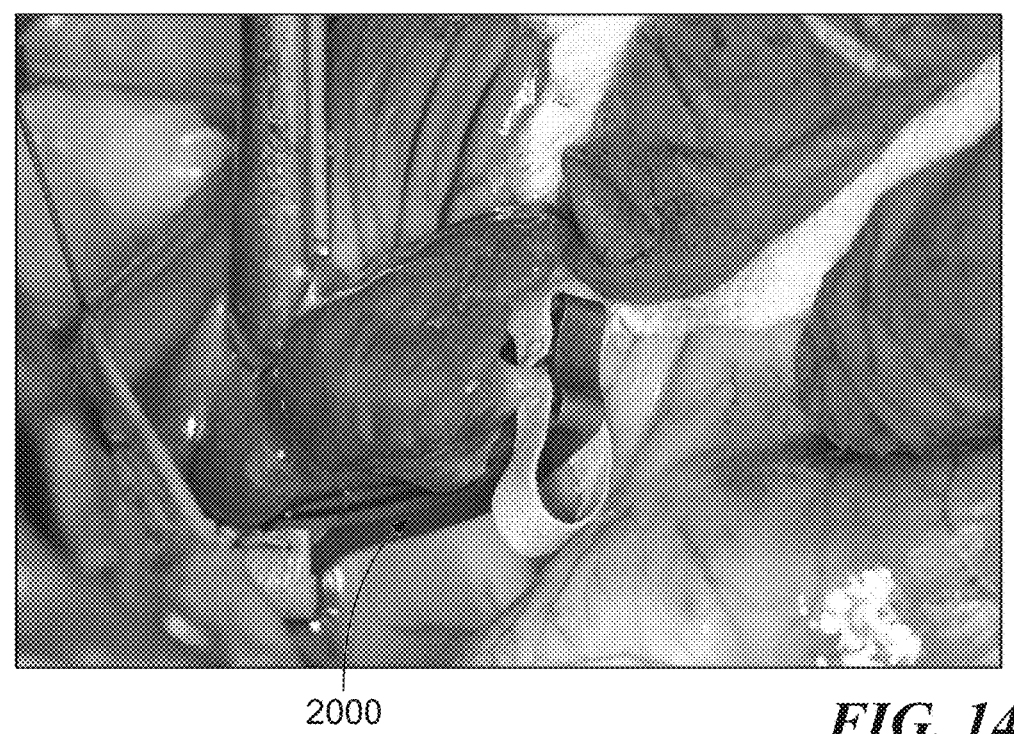

FIGS. 14A and 14B show images of an example occlusion device deployed onto the left atrial appendage, according to one implementation.

Figure 15A:
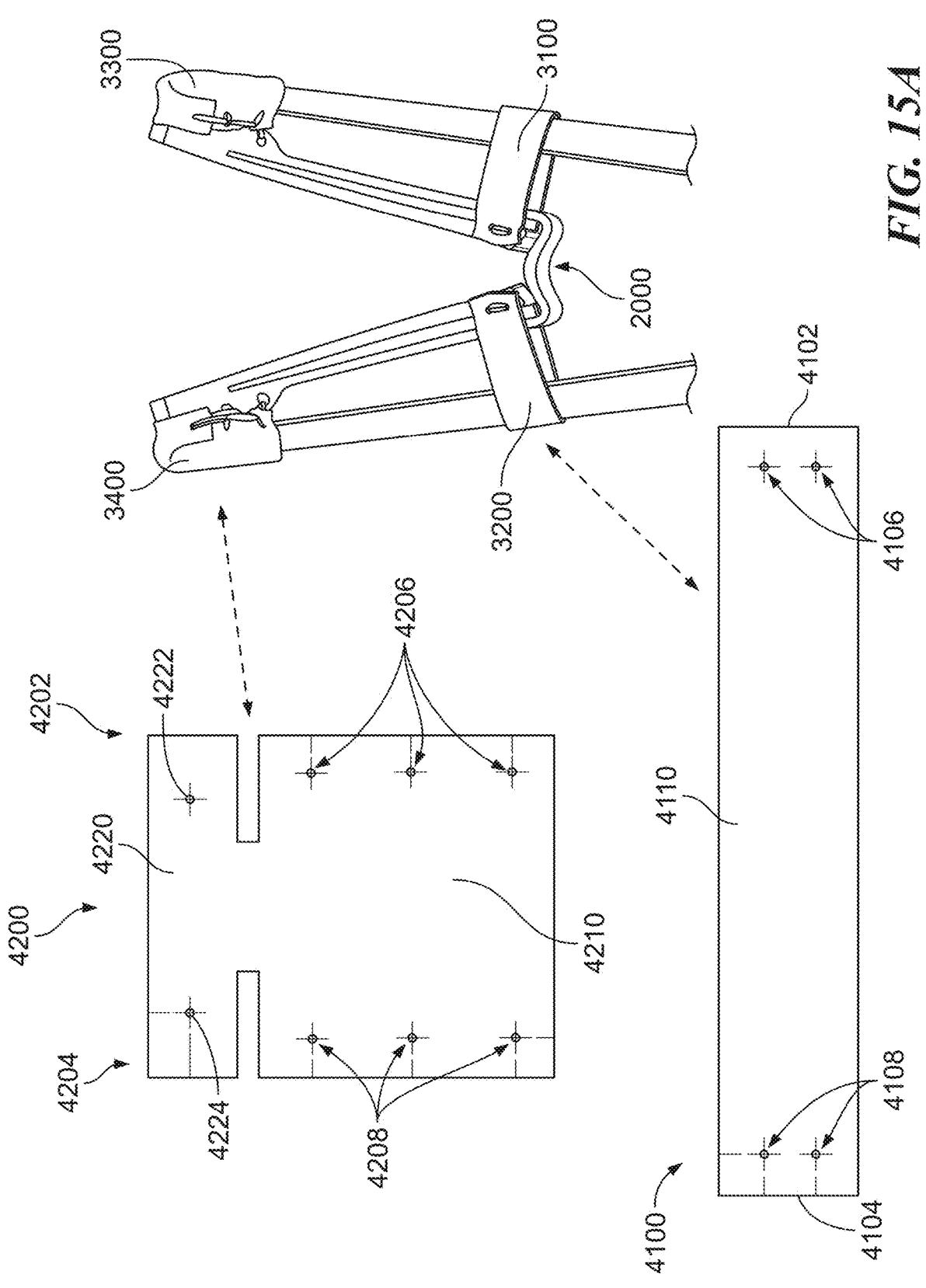

FIG. 15A shows exemplary sleeve layouts and their corresponding assembled configurations attached to an occlusion device, according to one implementation.

Figures 15B, 15C:
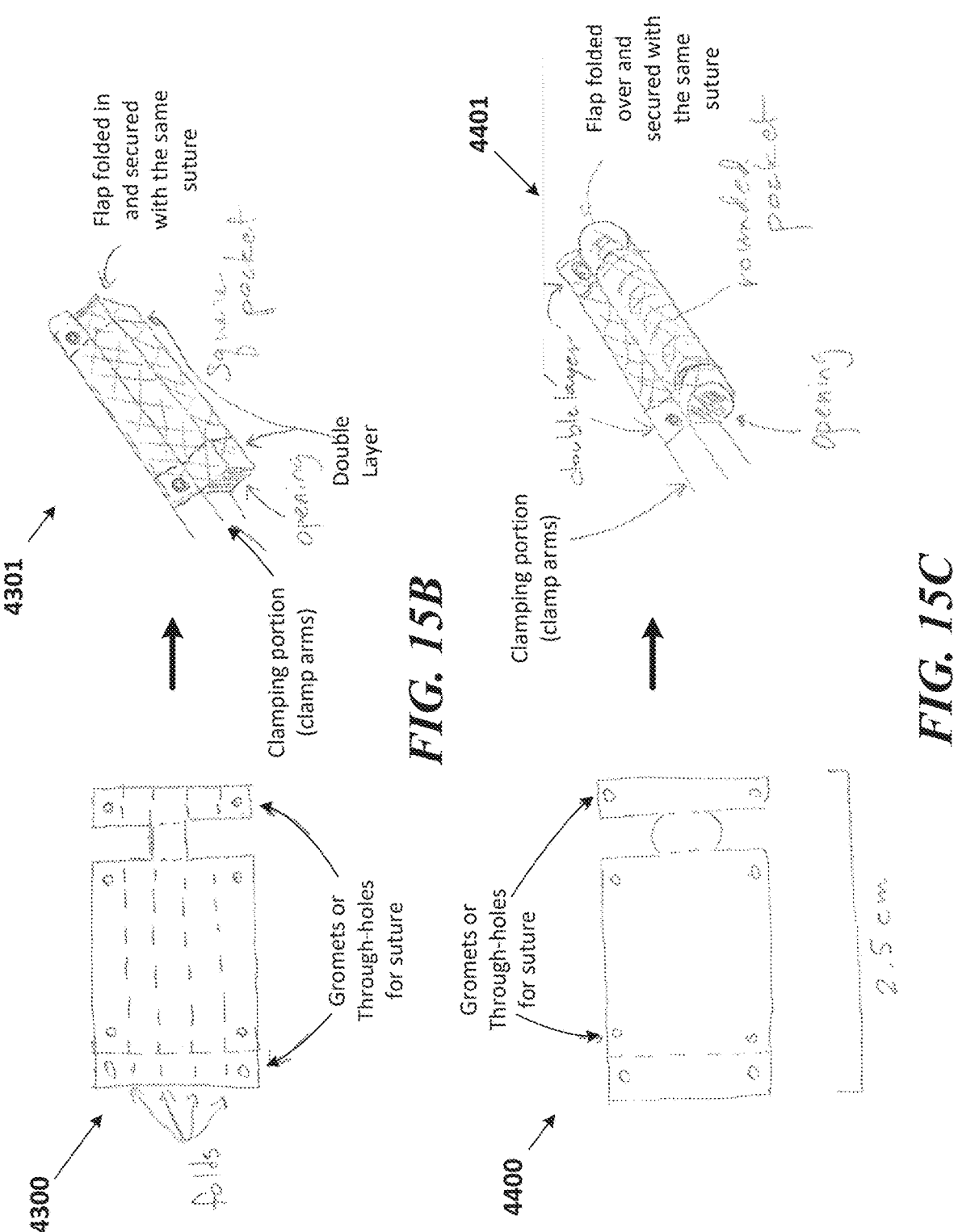

FIGS. 15B and 15C each show a foldable cloth sleeve layout in a flat configuration and an assembled configuration, according to various implementations.

The detailed description is set forth with reference to the accompanying drawings. The drawings are provided for purposes of illustration only and merely depict example embodiments of the disclosure. The drawings are provided to facilitate understanding of the disclosure and shall not be deemed to limit the breadth, scope, or applicability of the disclosure. The use of the same reference numerals indicates similar, but not necessarily the same or identical components. Different reference numerals may be used to identify similar components. Various embodiments may utilize elements or components other than those illustrated in the drawings, and some elements and/or components may not be present in various embodiments. The use of singular terminology to describe a component or element may, depending on the context, encompass a plural number of such components or elements and vice versa.

DETAILED DESCRIPTION OF THE DISCLOSURE

In the following description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional. In some instances, well known methods, procedures, and components have not been described in detail so as not to unnecessarily obscure aspects of the embodiments.

Section I. Overview

Embodiments of devices and methods for occlusion of a hollow tissue structure of a living subject are provided herein, including, for example, occlusion of a left atrial appendage. According to disclosed embodiments, an occlusion device generally may include a first clamping portion and a second clamping portion configured for positioning along opposite sides of the left atrial appendage. The second clamping portion may be movably connected to the first clamping portion, and the occlusion device may be configured to transition between an open configuration and a closed configuration. In this manner, the occlusion device may be introduced and positioned with respect to the hollow tissue structure while the device is in the open configuration. Upon proper positioning of the occlusion device, the device may be transitioned from the open configuration toward the closed configuration. Specifically, the occlusion device may be transitioned from the open configuration to a deployed configuration in which the device occludes the hollow tissue structure (e.g., the left atrial appendage).

According to disclosed embodiments, the first clamping portion and the second clamping portion each may include an inner side, an outer side, a concave side, and a convex side. When the occlusion device is in the deployed configuration, the inner side may face toward the left atrial appendage, the outer side may face away from the left atrial appendage, the concave side may face away from the lateral wall of the left atrium from which the left atrial appendage extends, and the convex side may face toward the lateral wall. As described below, the shape of the first clamping portion and the second clamping portion of the occlusion device advantageously may decrease the incidence of incomplete occlusion as compared to certain existing occlusion devices. In particular, the shapes of the concave sides and the convex sides of the first clamping portion and the second clamping portion may better accommodate the shape of the base of the left atrial appendage in a manner that avoids a residual stump remaining un-occluded. According to various embodiments, the radius of curvature and the depth of curvature of the concave sides and the convex sides may be varied to better accommodate the anatomy of different subjects.

According to disclosed embodiments, one or more sleeves may be disposed on the outer side of each of the first clamping portion and the second clamping portion. Each of the sleeves is coupled to and/or integrally formed to extend out from the outer surface of the first and second clamping portions. Each of the sleeves defines an opening extending from a first end to a second end (e.g., an open second end or a closed second end) to define a channel. Each of the channels of the sleeves is sized and configured to accept the tips of a medical instrument. The sleeves facilitate moving the device between a closed configuration and an open configuration via an inserted medical device (e.g., forceps or clamps). By accommodating off-the-shelf instruments in the sleeves of the device, the device provides a simple and efficient method of attaching the device to the hollow tissue structure (e.g., to the left atrial appendage).

Still other benefits and advantages of the occlusion devices and methods provided herein over existing technology for hollow tissue structure occlusion (e.g., left atrial appendage occlusion) will be appreciated by those of ordinary skill in the art from the following description and the appended drawings.

Figures 1A, 1B, 1C:
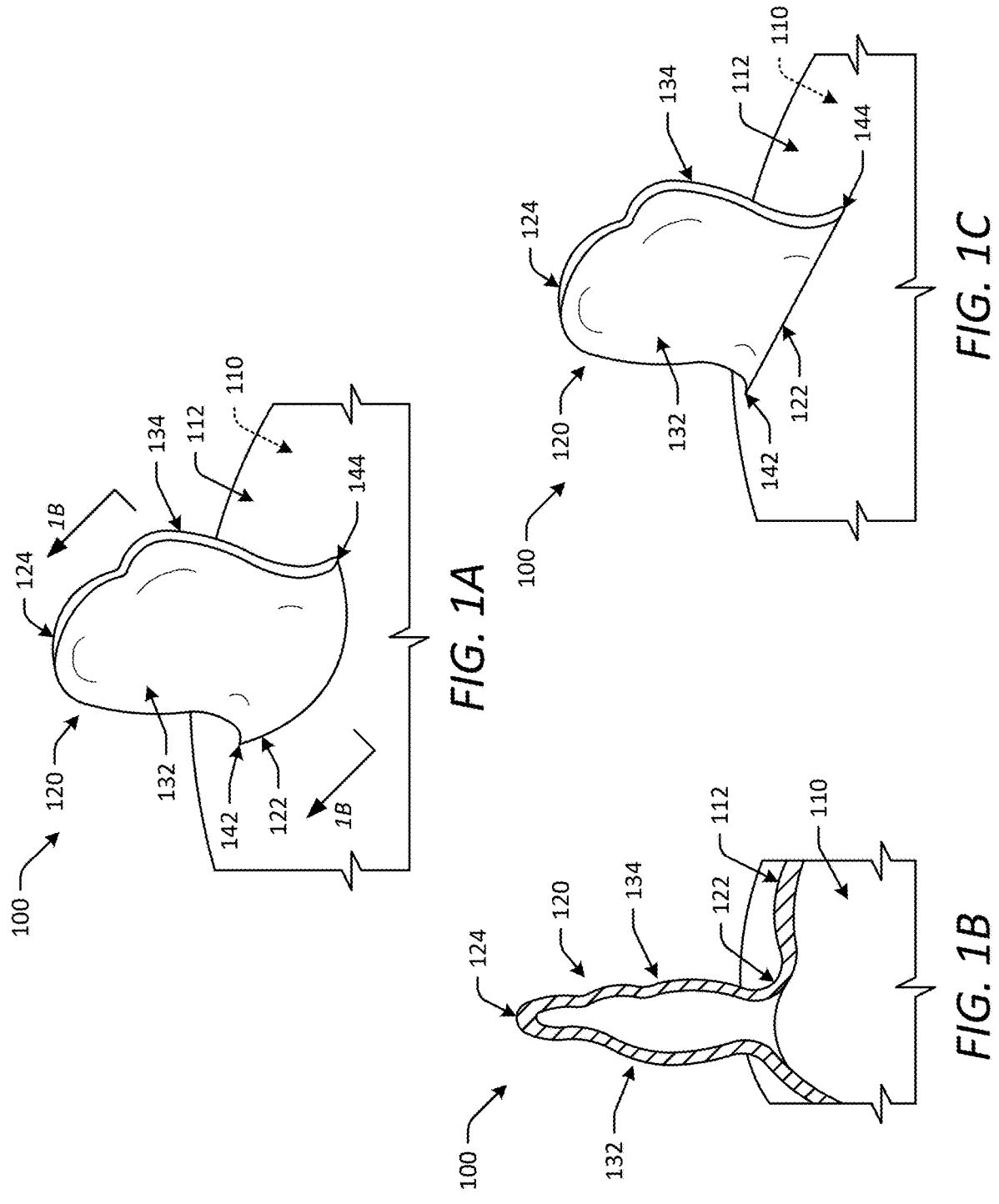
FIG. 1A is a perspective view of a portion of a heart while the heart is in situ, showing a left atrial appendage extending from a lateral wall of a left atrium of the heart, with a base of the left atrial appendage having a non-linear shape.
FIG. 1B is a cross-sectional view of the portion of the heart of FIG. 1A while the heart is in situ, with the cross-section taken along plane 1B-1B of FIG. 1A.
FIG. 1C is a perspective view of the portion of the heart of FIG. 1A while the heart is elevated from the chest, showing the base of the left atrial appendage having a linear shape.

Referring now to FIGS. 1A-1C, a portion of a heart 100 of a living subject (i.e., a human or an animal) is depicted. FIGS. 1A and 1B show the portion of the heart 100 while the heart 100 is in situ. FIG. 1C shows the portion of the heart 100 while the heart 100 is elevated from the chest of the subject, which positioning often may be used when performing a left atrial appendage occlusion procedure. As shown, a left atrial appendage 120 may extend from a lateral wall 112 of a left atrium 110 of the heart 100. It will be appreciated that the shape and size of the illustrated left atrial appendage 120 is merely an example, as the shape and size of the tissue structure may vary from one subject to another. As shown, the left atrial appendage 120 may include a base 122 and a tip 124 disposed opposite one another, with the base 122 connected to the lateral wall 112. The left atrial appendage 120 may have an overall height extending from the base 122 to the tip 124. As shown, the left atrial appendage 120 may include a first side 132 and a second side 134 disposed opposite one another, with the left atrial appendage 120 having an overall width extending from the first side 132 to the second side 134. The left atrial appendage 120 may include a first end 142 and a second end 144 disposed opposite one another, with the left atrial appendage 120 having an overall length extending from the first end 142 to the second end 144.

As shown, the shape of the base 122 of the left atrial appendage 120 may be different when the heart 100 is elevated from the chest as compared to when the heart 100 is in situ. In particular, the present inventor has observed that, while the heart 100 is elevated, the base 122 may have a linear, or substantially linear, shape, as shown in FIG. 1C, and that, while the heart 100 is in situ, the base 122 may have a non-linear shape, as shown in FIG. 1A. The non-linear shape of the base 122 may be generally C-shaped, with a radius of curvature and a depth of curvature of the base 122 varying from one subject to another. The non-linear shape of the base 122 is due to the positioning of the left atrial appendage 120 at the reflection of the left superior pulmonary vein and the body of the left atrium 110, which forms a fold. The present inventor has observed that, when performing an occlusion procedure with certain existing occlusion devices, the non-linear shape of the base 122 may result in incomplete occlusion of the left atrial appendage 120 in a varying number of subjects, depending on the series and the degree to which this is evaluated by imaging. Such incomplete occlusion may leave a residual stump of the left atrial appendage 120, which may be a source of thrombus formation and thus may present a subsequent risk of stroke. It is estimated that procedures using certain existing occlusion devices may result in incomplete occlusion in as many as 25% of cases.

Figures 2A, 2B, 2C, 2D:
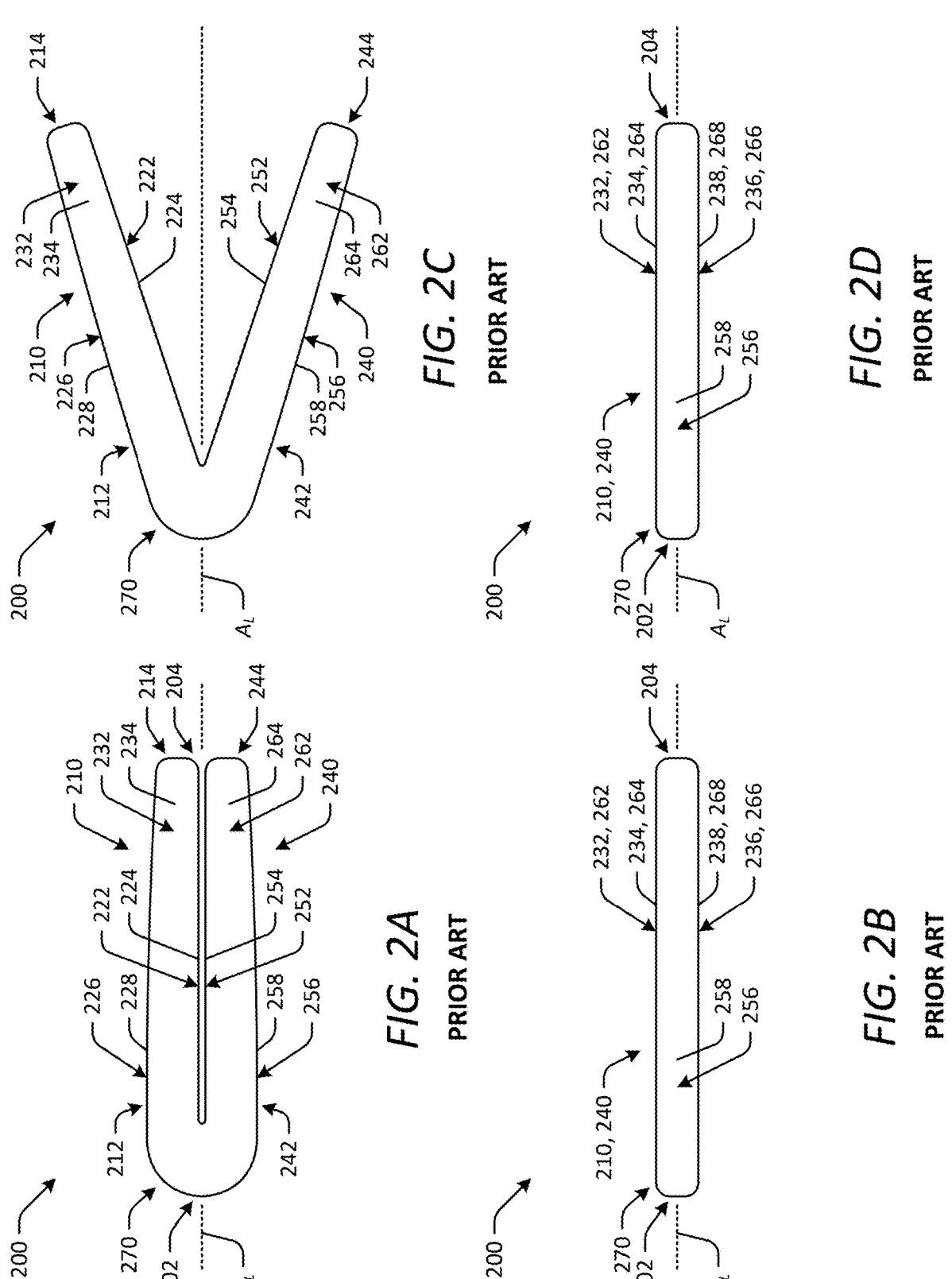
FIG. 2A is a top view of an example occlusion device in a closed configuration.
FIG. 2B is a side view of the occlusion device of FIG. 2A in the closed configuration.
FIG. 2C is a top view of the occlusion device of FIG. 2A in an open configuration.
FIG. 2D is a side view of the occlusion device of FIG. 2A in the open configuration.

FIGS. 2A-2F illustrate an example occlusion device 200, which generally may be representative of certain existing occlusion devices. The occlusion device 200 may be formed as an elongate structure, with a first end 202 and a second end 204 disposed opposite one another along a longitudinal axis A$_L$ of the device 200. As shown, the device 200 may include a first clamping portion 210 and a second clamping portion 240 connected to one another by a connecting portion 270. The connecting portion 270 may be configured to allow the first clamping portion 210 and the second clamping portion 240 to move relative to one another. Specifically, the occlusion device 200 may be configured to transition between a closed configuration, as shown in FIGS. 2A and 2B, and an open configuration, as shown in FIGS. 2C and 2D. The device 200 may be biased from the open configuration toward, or to, the closed configuration. For example, the connecting portion 270 may bias the device 200 from the open configuration toward, or to, the closed configuration. As shown, the connecting portion 270 may be formed as a hinge and configured to allow the first clamping portion 210 and the second clamping portion 240 to pivot relative to one another as the device 200 transitions between the closed configuration and the open configuration.

The first clamping portion 210 may be formed as an elongate structure, with a first end 212 and a second end 214 disposed opposite one another. The first clamping portion 210 may extend from the connecting portion 270 to the second end 204 of the device 200. As shown, the first clamping portion 210 may include an inner side 222 having an inner surface 224, an outer side 226 disposed opposite the inner side 222 and having an outer surface 228, a top side 232 having a top surface 234, and a bottom side 236 disposed opposite the top side 232 and having a bottom surface 238. As shown, the inner surface 224 may be a planar surface having a linear profile when viewed from the top side or the bottom side of the device 200, while the outer surface 228 may be a slightly contoured surface having a non-linear profile when viewed from the top side or the bottom side of the device 200. As shown, the top surface 234 may be a planar surface having a linear profile when viewed from one of the lateral sides of the device 200, and the bottom surface 238 may be a planar surface having a linear profile when viewed from one of the lateral sides of the device 200.

Similarly, the second clamping portion 240 may be formed as an elongate structure, with a first end 242 and a second end 244 disposed opposite one another. The second clamping portion 240 may extend from the connecting portion 270 to the second end 204 of the device 200. As shown, the second clamping portion 240 may include an inner side 252 having an inner surface 254, an outer side 256 disposed opposite the inner side 252 and having an outer surface 258, a top side 262 having a top surface 264, and a bottom side 266 disposed opposite the top side 262 and having a bottom surface 268. As shown, the inner surface 254 may be a planar surface having a linear profile when viewed from the top side or the bottom side of the device 200, while the outer surface 258 may be a slightly contoured surface having a non-linear profile when viewed from the top side or the bottom side of the device 200. As shown, the top surface 264 may be a planar surface having a linear profile when viewed from one of the lateral sides of the device 200, and the bottom surface 268 may be a planar surface having a linear profile when viewed from one of the lateral sides of the device 200. As shown, the second clamping portion 240 may be formed as a mirror image of the first clamping portion 210 across a plane extending through the longitudinal axis A$_L$ of the device 200.

Figure 2F:
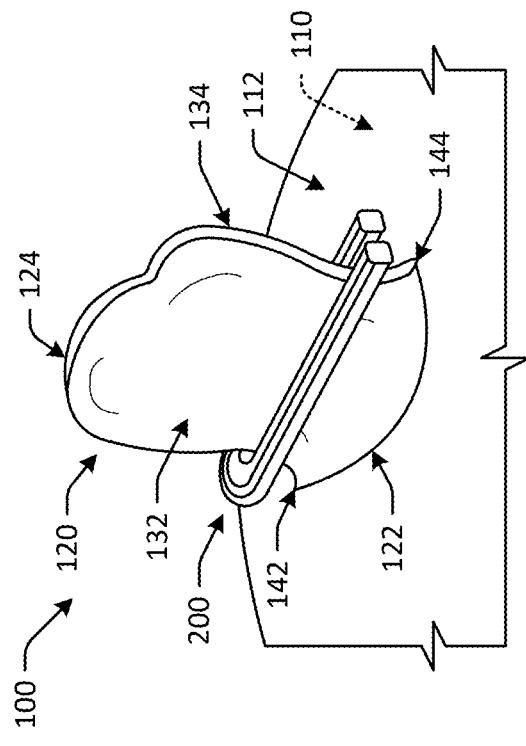
FIG. 2F is a perspective view of the occlusion device of FIG. 2A in the deployed configuration, showing the occlusion device secured to the left atrial appendage of the portion of the heart of FIG. 1A while the heart is in situ.
Figure 2E:
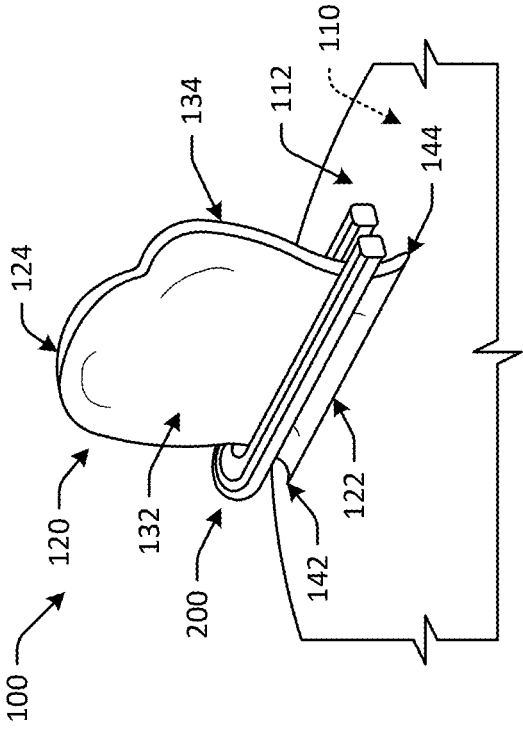
FIG. 2E is a perspective view of the occlusion device of FIG. 2A in a deployed configuration, showing the occlusion device secured to the left atrial appendage of the portion of the heart of FIG. 1A while the heart is elevated from the chest.

During use, the occlusion device 200 may be introduced and positioned relative to a left atrial appendage while the device 200 is in the open configuration. Upon positioning, the device 200 may be transitioned from the open configuration toward the closed configuration. It will be appreciated that, with the left atrial appendage positioned between the first clamping portion 210 and the second clamping portion 240, the appendage may inhibit the device 200 from transitioning all the way to the closed configuration shown in FIGS. 2A and 2B. Rather, the device 200 may transition to a deployed configuration, as shown in FIGS. 2E and 2F. As shown, one of the clamping portions 210, 240 may be positioned along the first side 132 of the left atrial appendage 120, while the other clamping portion 210, 240 may be positioned along the second side 134 of the left atrial appendage 120. When the device 200 is in the deployed configuration, the inner sides 222, 252 of the clamping portions 210, 240 may face toward the left atrial appendage 120, the outer sides 226, 256 of the clamping portions 210, 240 may face away from the left atrial appendage 120, the top sides 232, 262 of the clamping portions 210, 240 may face away from the lateral wall 112 of the left atrium 110, and the bottom sides 236, 266 of the clamping portions 210, 240 may face toward the lateral wall 112 of the left atrium 110.

FIGS. 2E and 2F illustrate the problem of incomplete occlusion of the left atrial appendage 120 due to the non-linear shape of the base 122 when the heart 100 is in situ. FIG. 2E illustrates the portion of the heart 100 while the heart 100 is elevated during implantation of the device 200, showing the base 122 having a linear, or substantially linear, shape. FIG. 2F illustrates the portion of the heart 100 while the heart 100 is in situ, showing the base 122 having a non-linear shape. As shown, the non-linear shape of the base 122 may result in incomplete occlusion of the left atrial appendage 120 when using the occlusion device 200, leaving a residual stump of the left atrial appendage 120.

Figures 3A, 3B, 3C, 3D, 3E, 3F:
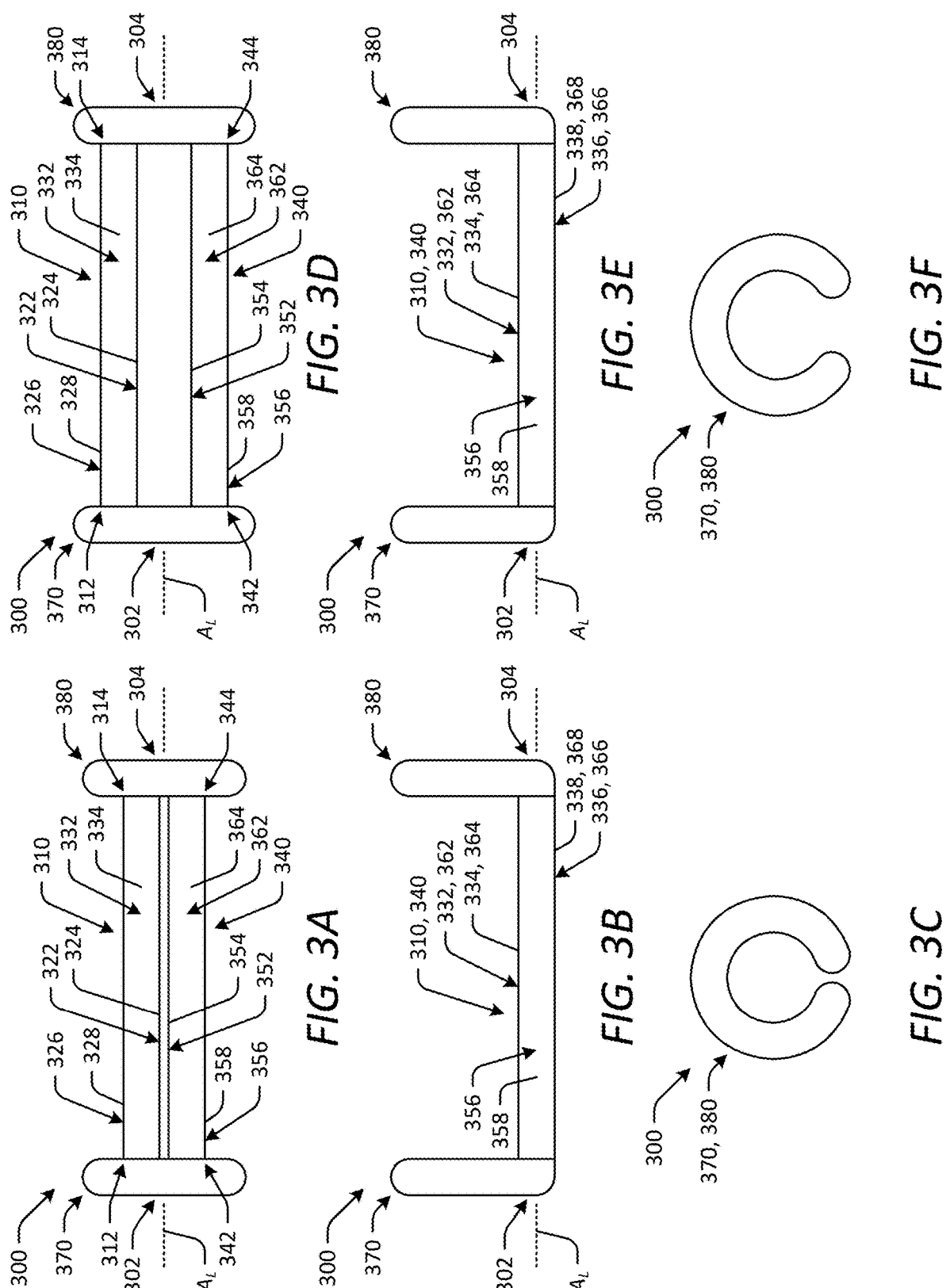
FIG. 3A is a top view of an example occlusion device in a closed configuration.
FIG. 3B is a side view of the occlusion device of FIG. 3A in the closed configuration.
FIG. 3C is an end view of the occlusion device of FIG. 3A in the closed configuration.
FIG. 3D is a top view of the occlusion device of FIG. 3A in an open configuration.
FIG. 3E is a side view of the occlusion device of FIG. 3A in the open configuration.
FIG. 3F is an end view of the occlusion device of FIG. 3A in the open configuration.

FIGS. 3A-3F illustrate an example occlusion device 300, which generally may be representative of certain existing occlusion devices. The occlusion device 300 may be formed as an elongate structure, with a first end 302 and a second end 304 disposed opposite one another along a longitudinal axis A$_L$ of the device 300. As shown, the device 300 may include a first clamping portion 310 and a second clamping portion 340 connected to one another by each of a first connecting portion 370 and a second connecting portion 380. The first connecting portion 370 and the second connecting portion 380 may be configured to allow the first clamping portion 310 and the second clamping portion 340 to move relative to one another. Specifically, the occlusion device 300 may be configured to transition between a closed configuration, as shown in FIGS. 3A-3C, and an open configuration, as shown in FIGS. 3D-3F. The device 300 may be biased from the open configuration toward, or to, the closed configuration. For example, the connecting portions 370, 380 may bias the device 300 from the open configuration toward, or to, the closed configuration. As shown, the connecting portions 370, 380 may be formed as curved members configured to allow the first clamping portion 310 and the second clamping portion 340 to translate relative to one another as the device 300 transitions between the closed configuration and the open configuration.

The first clamping portion 310 may be formed as an elongate structure, with a first end 312 and a second end 314 disposed opposite one another. The first clamping portion 310 may extend from the first connecting portion 370 to the second connecting portion 380. As shown, the first clamping portion 310 may include an inner side 322 having an inner surface 324, an outer side 326 disposed opposite the inner side 322 and having an outer surface 328, a top side 332 having a top surface 334, and a bottom side 336 disposed opposite the top side 332 and having a bottom surface 338. As shown, the inner surface 324 may be a curved surface having a linear profile when viewed from the top side or the bottom side of the device 300, and the outer surface 328 may be a curved surface having a linear profile when viewed from the top side or the bottom side of the device 300. As shown, the top surface 334 may be a curved surface having a linear profile when viewed from one of the lateral sides of the device 300, and the bottom surface 338 may be a curved surface having a linear profile when viewed from one of the lateral sides of the device 300.

Similarly, the second clamping portion 340 may be formed as an elongate structure, with a first end 342 and a second end 344 disposed opposite one another. The second clamping portion 340 may extend from the first connecting portion 370 to the second connecting portion 380. As shown, the second clamping portion 340 may include an inner side 352 having an inner surface 354, an outer side 356 disposed opposite the inner side 352 and having an outer surface 358, a top side 362 having a top surface 364, and a bottom side 366 disposed opposite the top side 362 and having a bottom surface 368. As shown, the inner surface 354 may be a curved surface having a linear profile when viewed from the top side or the bottom side of the device 300, and the outer surface 358 may be curved having a linear profile when viewed from the top side or the bottom side of the device 300. As shown, the top surface 364 may be a curved surface having a linear profile when viewed from one of the lateral sides of the device 300, and the bottom surface 368 may be a curved surface having a linear profile when viewed from one of the lateral sides of the device 300. As shown, the second clamping portion 340 may be formed as a mirror image of the first clamping portion 310 across a plane extending through the longitudinal axis $A_L$ of the device 300.

During use, the occlusion device 300 may be introduced and positioned relative to a left atrial appendage while the device 300 is in the open configuration. Upon positioning, the device 300 may be transitioned from the open configuration toward the closed configuration. It will be appreciated that, with the left atrial appendage positioned between the first clamping portion 310 and the second clamping portion 340, the appendage may inhibit the device 300 from transitioning all the way to the closed configuration shown in FIGS. 3A-3C. Rather, the device 300 may transition to a deployed configuration between the open configuration and the closed configuration. One of the clamping portions 310, 340 may be positioned along the first side 132 of the left atrial appendage 120, while the other clamping portion 310, 340 may be positioned along the second side 134 of the left atrial appendage 120. When the device 300 is in the deployed configuration, the inner sides 322, 352 of the clamping portions 310, 340 may face toward the left atrial appendage 120, the outer sides 326, 356 of the clamping portions 310, 340 may face away from the left atrial appendage 120, the top sides 332, 362 of the clamping portions 310, 340 may face away from the lateral wall 112 of the left atrium 110, and the bottom sides 336, 366 of the clamping portions 310, 340 may face toward the lateral wall 112 of the left atrium 110.

It will be appreciated that use of the occlusion device 300, similar to the occlusion device 200 described above, also may result in the problem of incomplete occlusion of the left atrial appendage 120 due to the non-linear shape of the base 122 when the heart 100 is in situ, leaving a residual stump of the left atrial appendage 120.

Section II. Example Embodiments of Occlusion Devices

Figures 4A, 4B, 4C, 4D:
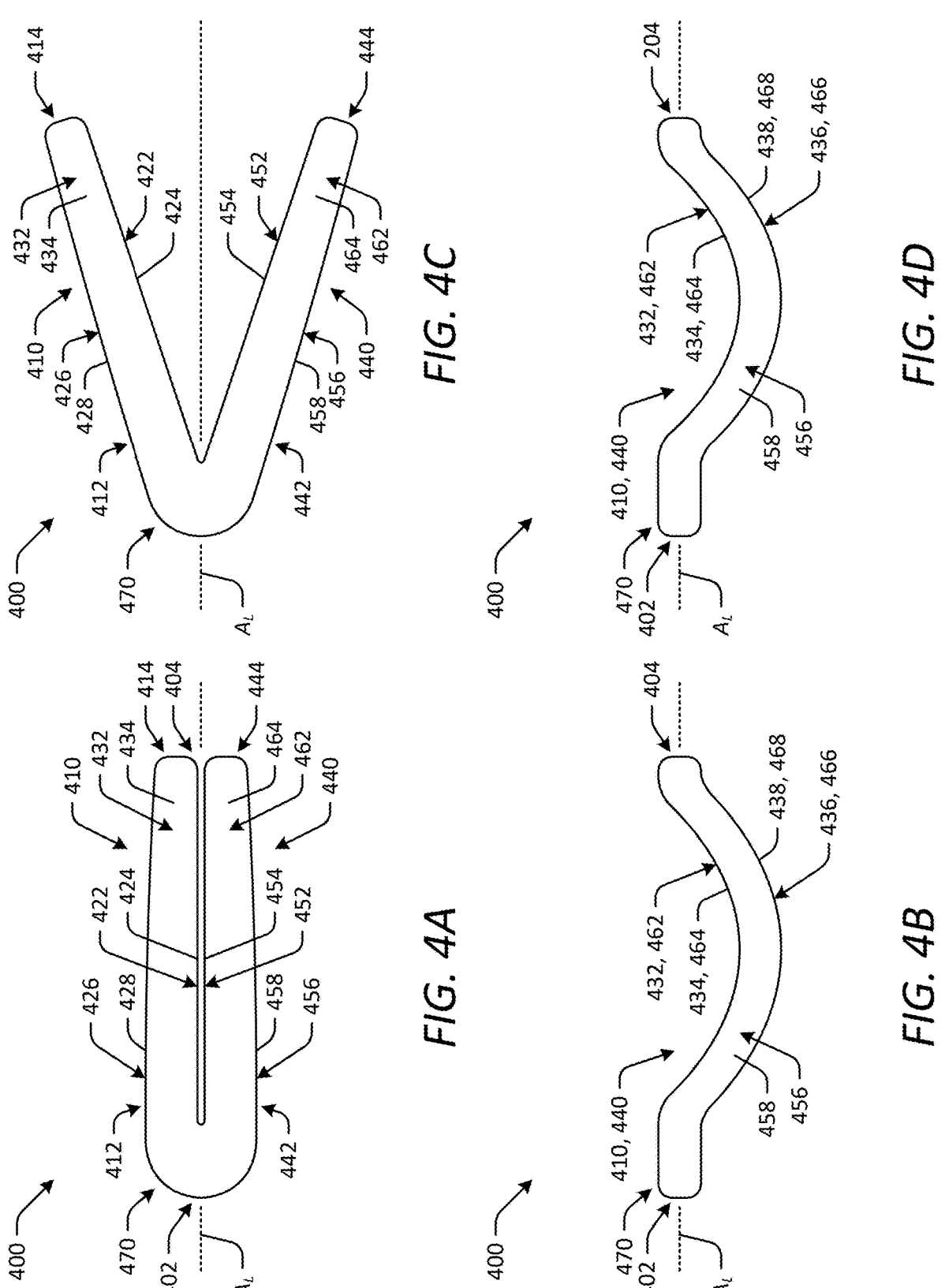
FIG. 4A is a top view of an example occlusion device in accordance with one or more embodiments of the disclosure, showing the occlusion device in a closed configuration.
FIG. 4B is a side view of the occlusion device of FIG. 4A in the closed configuration.
FIG. 4C is a top view of the occlusion device of FIG. 4A in an open configuration.
FIG. 4D is a side view of the occlusion device of FIG. 4A in the open configuration.

FIGS. 4A-4F illustrate an example occlusion device 400 (which also may be referred to as a "left atrial appendage occlusion device," a "device," a "clamp," a "clip," or an "implant") in accordance with embodiments of the disclosure. The occlusion device 400 may be formed as an elongate structure, with a first end 402 and a second end 404 disposed opposite one another along a longitudinal axis $A_L$ of the device 400. As shown, the device 400 may include a first clamping portion 410 and a second clamping portion 440 connected to one another by a connecting portion 470. The connecting portion 470 may be configured to allow the first clamping portion 410 and the second clamping portion 440 to move relative to one another. Specifically, the occlusion device 400 may be configured to transition between a closed configuration, as shown in FIGS. 4A and 4B, and an open configuration, as shown in FIGS. 4C and 4D. The device 400 may be biased from the open configuration toward, or to, the closed configuration. For example, the connecting portion 470 may bias the device 400 from the open configuration toward, or to, the closed configuration. As shown, the connecting portion 470 may be formed as a hinge and configured to allow the first clamping portion 410 and the second clamping portion 440 to pivot relative to one another as the device 400 transitions between the closed configuration and the open configuration.

The first clamping portion 410 may be formed as an elongate structure, with a first end 412 and a second end 414 disposed opposite one another. The first clamping portion 410 may extend from the connecting portion 470 to the second end 404 of the device 400. As shown, the first clamping portion 410 may include an inner side 422 having an inner surface 424, an outer side 426 disposed opposite the inner side 422 and having an outer surface 428, a top side 432 (which also may be referred to as a "concave side") having a top surface 434 (which also may be referred to as a "concave surface"), and a bottom side 436 (which also may be referred to as a "convex side") disposed opposite the top side 432 and having a bottom surface 438 (which also may be referred to as a "convex side"). As shown, the inner surface 424 may be a planar surface having a linear profile when viewed from the top side or the bottom side of the device 400, while the outer surface 428 may be a slightly contoured surface having a non-linear profile when viewed from the top side or the bottom side of the device 400. As shown, the top surface 434 may be a concave surface having a concave profile when viewed from one of the lateral sides of the device 400, and the bottom surface 438 may be a convex surface having a convex profile when viewed from one of the lateral sides of the device 400. According to various embodiments, the radius of curvature and the depth of curvature of the top surface 434 and the bottom surface 438 may be varied to better accommodate the anatomy of different subjects.

Similarly, the second clamping portion 440 may be formed as an elongate structure, with a first end 442 and a second end 444 disposed opposite one another. The second clamping portion 440 may extend from the connecting portion 470 to the second end 404 of the device 400. As shown, the second clamping portion 440 may include an inner side 452 having an inner surface 454, an outer side 456 disposed opposite the inner side 452 and having an outer surface 458, a top side 462 (which also may be referred to as a "concave side") having a top surface 464 (which also may be referred to as a "concave surface"), and a bottom side 466 (which also may be referred to as a "convex side") disposed opposite the top side 462 and having a bottom surface 468 (which also may be referred to as a "convex surface"). As shown, the inner surface 454 may be a planar surface having a linear profile when viewed from the top ide or the bottom side of the device 400, while the outer surface 458 may be a slightly contoured surface having a non-linear profile when viewed from the top side or the bottom side of the device 400. As shown, the top surface 464 may be a concave surface having a concave profile when viewed from one of the lateral sides of the device 400, and the bottom surface 468 may be a convex surface having a convex profile when viewed from one of the lateral sides of the device 400. According to various embodiments, the radius of curvature and the depth of curvature of the top surface 464 and the bottom surface 468 may be varied to better accommodate the anatomy of different subjects. As shown, the second clamping portion 440 may be formed as a mirror image of the first clamping portion 410 across a plane extending through the longitudinal axis $A_L$ of the device 400.

Figure 4F:
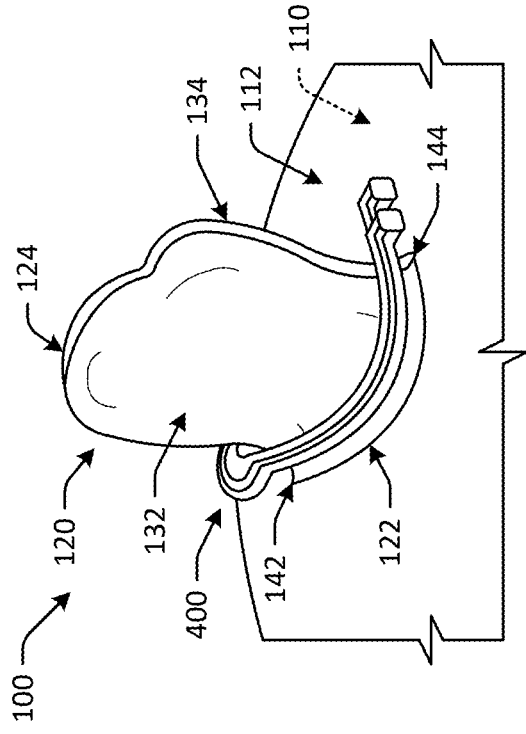
FIG. 4F is a perspective view of the occlusion device of FIG. 4A in the deployed configuration, showing the occlusion device secured to the left atrial appendage of the portion of the heart of FIG. 1A while the heart is in situ.
Figure 4E:
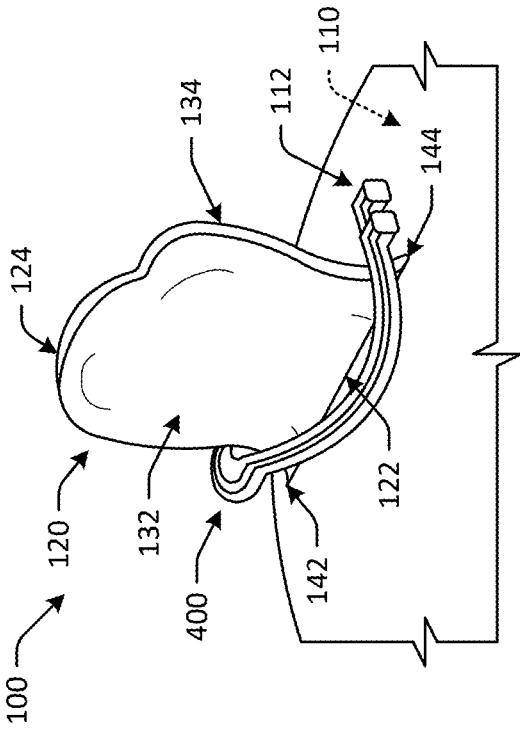
FIG. 4E is a perspective view of the occlusion device of FIG. 4A in a deployed configuration, showing the occlusion device secured to the left atrial appendage of the portion of the heart of FIG. 1A while the heart is elevated from the chest.

During use, the occlusion device 400 may be introduced and positioned relative to a left atrial appendage while the device 400 is in the open configuration. Upon positioning, the device 400 may be transitioned from the open configuration toward the closed configuration. It will be appreciated that, with the left atrial appendage positioned between the first clamping portion 410 and the second clamping portion 440, the appendage may inhibit the device 400 from transitioning all the way to the closed configuration shown in FIGS. 4A and 4B. Rather, the device 400 may transition to a deployed configuration, as shown in FIGS. 4E and 4F. As shown, one of the clamping portions 410, 440 may be positioned along the first side 132 of the left atrial appendage 120, while the other clamping portion 410, 440 may be positioned along the second side 134 of the left atrial appendage 120. When the device 400 is in the deployed configuration, the inner sides 422, 452 of the clamping portions 410, 440 may face toward the left atrial appendage 120, the outer sides 426, 456 of the clamping portions 410, 440 may face away from the left atrial appendage 120, the top sides 432, 462 of the clamping portions 410, 440 may face away from the lateral wall 112 of the left atrium 110, and the bottom sides 436, 466 of the clamping portions 410, 440 may face toward the lateral wall 112 of the left atrium 110.

FIGS. 4E and 4F illustrate how the shapes of the clamping portions 410, 440 of the occlusion device 400 may alleviate the problem of incomplete occlusion of the left atrial appendage 120 due to the non-linear shape of the base 122 when the heart 100 is in situ. FIG. 4E illustrates the portion of the heart 100 while the heart 100 is elevated during implantation of the device 400, showing the base 122 having a linear, or substantially linear, shape. FIG. 4F illustrates the portion of the heart 100 while the heart 100 is in situ, showing the base 122 having a non-linear shape. As compared to the clamping portions 210, 240 of the device 200 described above, the shapes of the clamping portions 410, 440 of the device 400 may better accommodate the non-linear shape of the base 122, reducing the incidence of incomplete occlusion of the left atrial appendage 120 when using the occlusion device 400.

FIGS. 5A-5F illustrate another example occlusion device 500 (which also may be referred to as a "left atrial appendage occlusion device," a "device," a "clamp," a "clip," or an "implant") in accordance with embodiments of the disclosure. Certain similarities and differences between the occlusion device 500 and the occlusion device 400 described above will be appreciated from the following description and the respective drawings. The occlusion device 500 may be formed as an elongate structure, with a first end 502 and a second end 504 disposed opposite one another along a longitudinal axis $A_L$ of the device 500. As shown, the device 500 may include a first clamping portion 510 and a second clamping portion 540 connected to one another by each of a first connecting portion 570 and a second connecting portion 580. The first connecting portion 570 and the second connecting portion 580 may be configured to allow the first clamping portion 510 and the second clamping portion 540 to move relative to one another. Specifically, the occlusion device 500 may be configured to transition between a closed configuration, as shown in FIGS. 5A-5C, and an open configuration, as shown in FIGS. 5D-5F. The device 500 may be biased from the open configuration toward, or to, the closed configuration. For example, the connecting portions 570, 580 may bias the device 500 from the open configuration toward, or to, the closed configuration. As shown, the connecting portions 570, 580 may be formed as curved members configured to allow the first clamping portion 510 and the second clamping portion 540 to translate relative to one another as the device 500 transitions between the closed configuration and the open configuration.

The first clamping portion 510 may be formed as an elongate structure, with a first end 512 and a second end 514 disposed opposite one another. The first clamping portion 510 may extend from the first connecting portion 570 to the second connecting portion 580. As shown, the first clamping portion 510 may include an inner side 522 having an inner surface 524, an outer side 526 disposed opposite the inner side 522 and having an outer surface 528, a top side 532 (which also may be referred to as a "concave side") having a top surface 534 (which also may be referred to as a "concave surface"), and a bottom side 536 (which also may be referred to as a "convex side") disposed opposite the top side 532 and having a bottom surface 538 (which also may be referred to as a "convex surface"). As shown, the inner surface 524 may be a curved surface having a linear profile when viewed from the top side or the bottom side of the device 500, and the outer surface 528 may be a curved surface having a linear profile when viewed from the top side or the bottom side of the device 500. As shown, the top surface 534 may be a curved surface having a concave profile when viewed from one of the lateral sides of the device 500, and the bottom surface 538 may be a curved surface having a convex profile when viewed from one of the lateral sides of the device 500. According to various embodiments, the radius of curvature and the depth of curvature of the top surface 534 and the bottom surface 538 may be varied to better accommodate the anatomy of different subjects.

Similarly, the second clamping portion 540 may be formed as an elongate structure, with a first end 542 and a second end 544 disposed opposite one another. The second clamping portion 540 may extend from the first connecting portion 570 to the second connecting portion 580. As shown, the second clamping portion 540 may include an inner side 552 having an inner surface 554, an outer side 556 disposed opposite the inner side 552 and having an outer surface 558, a top side 562 (which also may be referred to as a "concave side") having a top surface 564 (which also may be referred to as a "concave surface"), and a bottom side 566 (which also may be referred to as a "convex side") disposed opposite the top side 562 and having a bottom surface 568 (which also may be referred to as a "convex surface"). As shown, the inner surface 554 may be a curved surface having a linear profile when viewed from the top side or the bottom side of the device 500, and the outer surface 558 may be curved having a linear profile when viewed from the top side or the bottom side of the device 500. As shown, the top surface 564 may be a curved surface having a concave profile when viewed from one of the lateral sides of the device 500, and the bottom surface 568 may be a curved surface having a convex profile when viewed from one of the lateral sides of the device 500. According to various embodiments, the radius of curvature and the depth of curvature of the top surface 564 and the bottom surface 568 may be varied to better accommodate the anatomy of different subjects. As shown, the second clamping portion 540 may be formed as a mirror image of the first clamping portion 510 across a plane extending through the longitudinal axis $A_L$ of the device 500.

During use, the occlusion device 500 may be introduced and positioned relative to a left atrial appendage while the device 500 is in the open configuration. Upon positioning, the device 500 may be transitioned from the open configuration toward the closed configuration. It will be appreciated that, with the left atrial appendage positioned between the first clamping portion 510 and the second clamping portion 540, the appendage may inhibit the device 500 from transitioning all the way to the closed configuration shown in FIGS. 5A-5C. Rather, the device 500 may transition to a deployed configuration between the open configuration and the closed configuration. One of the clamping portions 510, 540 may be positioned along the first side 132 of the left atrial appendage 120, while the other clamping portion 510, 540 may be positioned along the second side 134 of the left atrial appendage 120. When the device 500 is in the deployed configuration, the inner sides 522, 552 of the clamping portions 510, 540 may face toward the left atrial appendage 120, the outer sides 526, 556 of the clamping portions 510, 540 may face away from the left atrial appendage 120, the top sides 532, 562 of the clamping portions 510, 540 may face away from the lateral wall 112 of the left atrium 110, and the bottom sides 536, 566 of the clamping portions 510, 540 may face toward the lateral wall 112 of the left atrium 110.

It will be appreciated that use of the occlusion device 500, similar to the occlusion device 400 described above, also may alleviate the problem of incomplete occlusion of the left atrial appendage 120 due to the non-linear shape of the base 122 when the heart 100 is in situ. As compared to the clamping portions 310, 340 of the device 300 described above, the shapes of the clamping portions 510, 540 of the device 500 may better accommodate the non-linear shape of the base 122, reducing the incidence of incomplete occlusion of the left atrial appendage 120 when using the occlusion device 500.

FIGS. 6A-6F illustrate another example occlusion device 600 (which also may be referred to as a "left atrial appendage occlusion device," a "device," a "clamp," a "clip," or an "implant") in accordance with embodiments of the disclosure. Certain similarities and differences between the occlusion device 600 and the occlusion devices 400, 500 described above will be appreciated from the following description and the respective drawings. The occlusion device 600 may be formed as an elongate structure, with a first end 602 and a second end 604 disposed opposite one another along a longitudinal axis $A_L$ of the device 600. As shown, the device 600 may include a first clamping portion 610 and a second clamping portion 640 connected to one another by each of a first connecting portion 670 and a second connecting portion 680. The first connecting portion 670 and the second connecting portion 680 may be configured to allow the first clamping portion 610 and the second clamping portion 640 to move relative to one another. Specifically, the occlusion device 600 may be configured to transition between a closed configuration, as shown in FIGS. 6A-6C, and an open configuration, as shown in FIGS. 6D-6F. The device 600 may be biased from the open configuration toward, or to, the closed configuration. For example, the connecting portions 670, 680 may bias the device 600 from the open configuration toward, or to, the closed configuration. As shown, the connecting portions 670, 680 may be formed as curved members configured to allow the first clamping portion 610 and the second clamping portion 640 to translate relative to one another as the device 600 transitions between the closed configuration and the open configuration.

The first clamping portion 610 may be formed as an elongate structure, with a first end 612 and a second end 614 disposed opposite one another. The first clamping portion 610 may extend from the first connecting portion 670 to the second connecting portion 680. As shown, the first clamping portion 610 may include an inner side 622 having an inner surface 624, an outer side 626 disposed opposite the inner side 622 and having an outer surface 628, a top side 632 (which also may be referred to as a "concave side") having a top surface 634 (which also may be referred to as a "concave surface"), and a bottom side 636 (which also may be referred to as a "convex side") disposed opposite the top side 632 and having a bottom surface 638 (which also may be referred to as a "convex surface"). As shown, the inner surface 624 may be a curved surface having a linear profile when viewed from the top side or the bottom side of the device 600, and the outer surface 628 may be a curved surface having a linear profile when viewed from the top side or the bottom side of the device 600. As shown, the top surface 634 may be a curved surface having a concave profile when viewed from one of the lateral sides of the device 600, and the bottom surface 638 may be a curved surface having a convex profile when viewed from one of the lateral sides of the device 600. According to various embodiments, the radius of curvature and the depth of curvature of the top surface 634 and the bottom surface 638 may be varied to better accommodate the anatomy of different subjects.

Similarly, the second clamping portion 640 may be formed as an elongate structure, with a first end 642 and a second end 644 disposed opposite one another. The second clamping portion 640 may extend from the first connecting portion 670 to the second connecting portion 680. As shown, the second clamping portion 640 may include an inner side 652 having an inner surface 654, an outer side 656 disposed opposite the inner side 652 and having an outer surface 658, a top side 662 (which also may be referred to as a "concave side") having a top surface 664 (which also may be referred to as a "concave surface"), and a bottom side 666 (which also may be referred to as a "convex side") disposed opposite the top side 662 and having a bottom surface 668 (which also may be referred to as a "convex surface"). As shown, the inner surface 654 may be a curved surface having a linear profile when viewed from the top side or the bottom side of the device 600, and the outer surface 658 may be curved having a linear profile when viewed from the top side or the bottom side of the device 600. As shown, the top surface 664 may be a curved surface having a concave profile when viewed from one of the lateral sides of the device 600, and the bottom surface 668 may be a curved surface having a convex profile when viewed from one of the lateral sides of the device 600. According to various embodiments, the radius of curvature and the depth of curvature of the top surface 664 and the bottom surface 668 may be varied to better accommodate the anatomy of different subjects. As shown, the second clamping portion 640 may be formed as a mirror image of the first clamping portion 610 across a plane extending through the longitudinal axis $A_L$ of the device 600.

During use, the occlusion device 600 may be introduced and positioned relative to a left atrial appendage while the device 600 is in the open configuration. Upon positioning, the device 600 may be transitioned from the open configuration toward the closed configuration. It will be appreciated that, with the left atrial appendage positioned between the first clamping portion 610 and the second clamping portion 640, the appendage may inhibit the device 600 from transitioning all the way to the closed configuration shown in FIGS. 6A-6C. Rather, the device 600 may transition to a deployed configuration between the open configuration and the closed configuration. One of the clamping portions 610, 640 may be positioned along the first side 132 of the left atrial appendage 120, while the other clamping portion 610, 640 may be positioned along the second side 134 of the left atrial appendage 120. When the device 600 is in the deployed configuration, the inner sides 622, 652 of the clamping portions 610, 640 may face toward the left atrial appendage 120, the outer sides 626, 656 of the clamping portions 610, 640 may face away from the left atrial appendage 120, the top sides 632, 662 of the clamping portions 610, 640 may face away from the lateral wall 112 of the left atrium 110, and the bottom sides 636, 666 of the clamping portions 610, 640 may face toward the lateral wall 112 of the left atrium 110.

It will be appreciated that use of the occlusion device 600, similar to the occlusion device 400 described above, also may alleviate the problem of incomplete occlusion of the left atrial appendage 120 due to the non-linear shape of the base 122 when the heart 100 is in situ. As compared to the clamping portions 310, 340 of the device 300 described above, the shapes of the clamping portions 610, 640 of the device 600 may better accommodate the non-linear shape of the base 122, reducing incidence of incomplete occlusion of the left atrial appendage 120 when using the occlusion device 600.

It will be appreciated that the example occlusion devices 400, 500, 600 depicted in the drawings are merely a few examples of occlusion devices in accordance with the present disclosure. In some embodiments of the disclosed occlusion devices, certain features and/or relationships illustrated in the drawings may not be present. In other embodiments of the disclosed occlusion devices, certain features and/or relationships not illustrated in the drawings may be present. In some embodiments, features of the occlusion devices 400, 500, 600 may have the relative dimensional relationships illustrated in the drawings. In other embodiments, features of the occlusion devices 400, 500, 600 may have relative dimensional relationships different from those illustrated in the drawings.

FIGS. 7A-7D illustrate an example occlusion device 700 (which also may be referred to as a "left atrial appendage occlusion device," a "device," a "clamp," a "clip," or an "implant") in accordance with embodiments of the disclosure. The occlusion device 700 may be formed as an elongate structure, with a first end 702 and a second end 704 disposed opposite one another along a longitudinal axis $A_L$ of the device 700. As shown, the device 700 may include a first clamping portion 710 and a second clamping portion 740 connected to one another by a connecting portion 770. The connecting portion 770 may be configured to allow the first clamping portion 710 and the second clamping portion 740 to move relative to one another. Specifically, the occlusion device 700 may be configured to transition between a closed configuration, as shown in FIGS. 7A and 7B, and an open configuration, as shown in FIGS. 7C and 7D. The device 700 may be biased from the open configuration toward, or to, the closed configuration. For example, the connecting portion 770 may bias the device 700 from the open configuration toward, or to, the closed configuration. As shown, the connecting portion 770 may be formed as a hinge and configured to allow the first clamping portion 710 and the second clamping portion 740 to pivot relative to one another as the device 700 transitions between the closed configuration and the open configuration.

The first clamping portion 710 may be formed as an elongate structure, with a first end 712 and a second end 714 disposed opposite one another. The first clamping portion 710 may extend from the connecting portion 770 to the second end 704 of the device 700. As shown, the first clamping portion 710 may include an inner side 722 having an inner surface 724, an outer side 726 disposed opposite the inner side 722 and having an outer surface 728, a top side 732 (which also may be referred to as a "concave side") having a top surface 734 (which also may be referred to as a "concave surface"), and a bottom side 736 (which also may be referred to as a "convex side") disposed opposite the top side 732 and having a bottom surface 738 (which also may be referred to as a "convex surface"). As shown, the inner surface 724 may be a planar surface having a linear profile when viewed from the top side or the bottom side of the device 700, while the outer surface 728 may be a slightly contoured surface having a non-linear profile when viewed from the top side or the bottom side of the device 700. As shown, the top surface 734 may be a concave surface having a concave profile when viewed from one of the lateral sides of the device 700, and the bottom surface 738 may be a convex surface having a convex profile when viewed from one of the lateral sides of the device 700. According to various embodiments, the radius of curvature and the depth of curvature of the top surface 734 and the bottom surface 738 may be varied to better accommodate the anatomy of different subjects.

Similarly, the second clamping portion 740 may be formed as an elongate structure, with a first end 742 and a second end 744 disposed opposite one another. The second clamping portion 740 may extend from the connecting portion 770 to the second end 704 of the device 700. As shown, the second clamping portion 740 may include an inner side 752 having an inner surface 754, an outer side 756 disposed opposite the inner side 752 and having an outer surface 758, a top side 762 (which also may be referred to as a "concave side") having a top surface 764 (which also may be referred to as a "concave surface"), and a bottom side 766 (which also may be referred to as a "convex side") disposed opposite the top side 762 and having a bottom surface 768 (which also may be referred to as a "convex surface"). As shown, the inner surface 754 may be a planar surface having a linear profile when viewed from the top side or the bottom side of the device 700, while the outer surface 758 may be a slightly contoured surface having a non-linear profile when viewed from the top side or the bottom side of the device 700. As shown, the top surface 764 may be a concave surface having a concave profile when viewed from one of the lateral sides of the device 700, and the bottom surface 768 may be a convex surface having a convex profile when viewed from one of the lateral sides of the device 700. According to various embodiments, the radius of curvature and the depth of curvature of the top surface 764 and the bottom surface 768 may be varied to better accommodate the anatomy of different subjects. As shown, the second clamping portion 740 may be formed as a mirror image of the first clamping portion 710 across a plane extending through the longitudinal axis $A_L$ of the device 700.

The occlusion device 700 further includes a first sleeve 780 integrally coupled to and extending from the outer surface 728 of the first clamping portion 710. The first sleeve 780 includes a first end 781 and a second end 782 opposite and spaced apart from the first end 781. The first sleeve 780 defines a first opening 784 on a first end 781 of the first sleeve 780 and a second opening 786 on a second end 782 of the first sleeve 780. The first sleeve 780 defines a first channel 788 extending from the first opening 784 to the second opening 786 of the first sleeve 780. As shown, the first end 781 of the first sleeve 780 is closer to the first end 702 of the device 700, and the second end 782 of the first sleeve 780 is closer to the second end 704 of the device 700. However, in other implementations, the first sleeve is flipped such that the first end of the first sleeve, and the corresponding first opening, are closer to the second end of the device.

Similarly, the device 700 further includes a second sleeve 790 substantially similar to the first sleeve 780. The second sleeve 790 is integrally coupled to and extends from the outer surface 758 of the second clamping portion 740. The second sleeve 790 includes a first end 791 and a second end 792 opposite and spaced apart from the first end 791. The second sleeve 790 defines a first opening 794 on the first end 791 of the second sleeve 790 and a second opening 796 on the second end 792 of the second sleeve 790. The second sleeve 790 defines a second channel 798 extending from the first opening 794 to the second opening 796 of the second sleeve 790. As shown, the first end 791 of the second sleeve 790 is closer to the first end 702 of the device 700, and the second end 792 of the second sleeve 790 is closer to the second end 704 of the device 700. However, in other implementations, the second sleeve is flipped such that the first end of the second sleeve, and the corresponding second opening, are closer to the second end of the device.

The sleeves 780, 790 shown in FIGS. 7A-7D, their corresponding channels 788, 798, are substantially cylindrical with openings on either end. However, in other implementations, the second ends of the sleeves may be a closed end (e.g., forming a pocket as shown in FIGS. 10A-10D). A closed second end of the sleeve/pocket may retain the tips of the forceps within the sleeve/pocket when subjected to axial force, preventing the forceps from passing through the channel of the sleeve/pocket and potentially damaging the occlusion device or adjacent anatomy. However, in some implementations, sleeves having openings on both ends may retain the tips of the forceps due to the shape and structure of the channel. For example, the channel may be frustoconical in shape, having a narrowing diameter from the first end to the second end. Such an arrangement would retain the tips of the forceps at the point wherein the diameter of the tips matches that of the narrowing channel. In other implementations, other structures and geometries forming a pocket or a repository for the tips of a medical tool are contemplated by this disclosure.

During use, a medical device or instrument (e.g., a pair of forceps having two opposing tips) may be used along with the occlusion device 700. The sleeves 780, 790 are sized to accept and retain the tips of the forceps (not shown). Each tip of the forceps is inserted into the first openings 784, 794 of each corresponding sleeve 780, 790 and into the channels 788, 798. Thus, the sleeves 780, 790 facilitate moving the device 700 between the open and closed configuration via the forceps.

During use, the occlusion device 700 may be introduced and positioned relative to a left atrial appendage while the device 700 is in the open configuration. Upon positioning, the device 700 may be transitioned from the open configuration toward the closed configuration via the forceps. It will be appreciated that, with the left atrial appendage positioned between the first clamping portion 710 and the second clamping portion 740, the appendage may inhibit the device 700 from transitioning all the way to the closed configuration shown in FIGS. 7A and 7B. Rather, the device 700 may transition to a deployed configuration wherein one of the clamping portions 710, 740 may be positioned along the first side 132 of the left atrial appendage 120, while the other clamping portion 710, 740 may be positioned along the second side 134 of the left atrial appendage 120 (e.g., similar to the arrangement shown in FIGS. 4E and 4F). When the device 700 is in the deployed configuration, the inner sides 722, 752 of the clamping portions 710, 740 may face toward the left atrial appendage 120, the outer sides 726, 756 of the clamping portions 710, 740 may face away from the left atrial appendage 120, the top sides 732, 762 of the clamping portions 710, 740 may face away from the lateral wall 112 of the left atrium 110, and the bottom sides 736, 766 of the clamping portions 710, 740 may face toward the lateral wall 112 of the left atrium 110. The device 700 may be re-attached and re-deployed, as needed, based on the location of the device relative to the left atrial appendage 120. The sleeves 780, 790 facilitate the retraction of the forceps and the subsequent engagement of the forceps with the device 700 as needed. Similar to the device 400 shown in FIGS. 4E and 4F, the clamping portions 710, 740 of the occlusion device 700 may alleviate the problem of incomplete occlusion of the left atrial appendage 120 due to the non-linear shape of the base 122 when the heart 100 is in situ.

As shown, the sleeves 780, 790 are integrally formed with the first and second clamping portions 710, 740. For example, each of the sleeves and clamping portions may comprise the same material (e.g., nitinol, titanium, stainless steel, woven polyester, suture material (silk, ti-cron, tev-dek), Dacron cloth, additive manufacturing materials, plastic, and/or other biocompatible materials). In other implementations, each of the sleeves is not integrally formed with the clamping portions, but they are coupled to the clamping portions via a suture, a fastener, a clip, or another fastening means. For example, see the device and sleeves of FIGS. 12A-12C, showing a cloth sleeve attachable via sutures. In other implementations, the couplable sleeve may be removable after the device is implanted (e.g., by removing the sutures, by dissolving the sutures, by removing the sleeves, or by any other combination or variation of removing the sleeves).

In other implementations, each clamping portion may include more than one sleeve coupled to and extending therefrom (e.g., to provide multiple leverage points for engaging the device with the forceps, such as a distal sleeve and a proximal sleeve). In other implementations, the shape of the opening of the sleeves may be a shape other than circular (e.g., elliptical or square). In other implementations, the shape of the channel of the sleeves may be a shape other than cylindrical (e.g., conical, frustoconical, or rectangular prism). While forceps are specially mentioned in conjunction with the use of the device, the device may be configured for use with a variety of off-the-shelf tools. For example, the sleeves may be sized to fit a variety of surgical instruments in a variety of shapes and sizes, reducing the need for custom tools. While the sleeves in FIGS. 7A-7D are positioned roughly in the middle of the clamping portions, in other implementations the sleeves may be positioned anywhere along the length of the clamping portion (e.g., at the tip of the clamping portion).

While the device 700 is configured for occluding the left atrial appendage of the heart of a subject, the sleeves 780, 790 may be coupled to a different device for occluding different anatomy. For example, the same concept of sleeves coupled to either side of a clip biased inwardly for moving the clip between a closed and open configuration may be applied to a clip for occluding any hollow tissue structure of a living subject. For example, the sleeves of this disclosure may be applied to a clip for occluding other vascular structures (such as an aortic cross-clamp), a clip for clamping a bowel, a device for occluding an aneurysm to reduce the pressure therein, a device for restricting a hemorrhage, or a device for reducing blood supply to tumor).

FIG. 8 shows a top view and a side view of an example occlusion device 800 that is similar to the occlusion device 700 shown and described in FIGS. 7A-7D except as described below. The device 800 includes lateral pockets or cups, similar to the sleeves of the device 700. However, the second end of the lateral pockets of the device 800 are closed. The pockets and the corresponding channel therein are curved to match the concave shape of the device 800. As shown, the first and second clamping portions, including the first and second pockets, comprise titanium. As shown, the connecting portion between the first and second clamping portions comprises Nitinol.

FIG. 9 shows a side view and a top view of an example occlusion device 900, as well as a top view of another example occlusion device 901, according to one implementation. The devices 900, 901 are similar to the occlusion device 700 shown and described in FIGS. 7A-7D. The devices 900, 901 include lateral pockets with a corresponding channel curved to match the concave shape of the devices 900, 901. However, the second end of the lateral pockets of the devices 900, 901 are closed. The connecting portion of the devices 900, 901 comprise Nitinol while the first and second clamping portions comprise titanium, similar to the device 800. However, the Nitinol connecting portion in devices 900, 901 extends further down the first and second clamping portions on the outer sides. Thus, at least a portion of the first and second clamping portions comprise Nitinol as well.

The device 901 differs from the device 900 in that the connecting portion of the device 901 has a thinner body as compared to the connecting portion of the device 900. This arrangement may be used, for example, to reduce the force needed to separate the first and second clamping portions when moving the device from the closed configuration to the open configuration.

FIGS. 10A-10D show perspective views of an example occlusion device 1000, according to one implementation. The device 1000 is substantially similar to the occlusion device 700 shown and described in FIGS. 7A-7D. However, the second end of the lateral pockets of the device 1000 are closed. Furthermore, the first and second pockets coupled to each of the first and second clamping portions are linear in shape. The corresponding channel of each of the pockets is also linear. A pocket longitudinal axis defined by each channel of the pockets is thus transverse to each clamping portion and its corresponding concave shape. As shown, the pockets are disposed at the "apex" of each of the clamping points. However, in other implementations, the pockets may be disposed on a different portion of the clamping portion (e.g., closer to the free end or closer to the connecting portion).

Section III. Example Embodiments of Occlusion Devices

FIGS. 11A-11C illustrate an example occlusion device 2000 (which also may be referred to as a "left atrial appendage occlusion device," a "device," a "clamp," a "clip," or an "implant") in accordance with embodiments of the disclosure. The occlusion device 2000 may be formed as an elongate structure, with a proximal or first end 2002 and a distal or second end 2004 disposed opposite one another along a curved longitudinal axis 2001 of the device 2000.

The occlusion device 2000 is similar to the above-described devices (e.g., any of the devices shown and described with reference to FIGS. 2A-10D) in that the device 2000 is configured for moving between a closed, open, and deployed configuration with respect to a tissue portion. For example, the occlusion device 2000 is configured for occluding the left atrial appendage 120 of FIGS. 1A-1C. The device 2000 includes a first inner arm 2100, a second inner arm 2200, a first outer arm 2300, and a second outer arm 2400. Each of the first inner arm 2100, the second inner arm 2200, the first outer arm 2300, and the second outer arm 2400 are integrally formed into a single occlusion device 2000 as described below.

The first inner arm 2100 extends from a first end 2102 of the first inner arm 2100 to a second end 2104 of the first inner arm 2100 along a first direction. The first direction is defined as a direction parallel to the curved longitudinal axis 2001 (e.g., either from the first end 2002 towards the second end 2004, or from the second end 2004 towards the first end 2002, of the occlusion device 2000).

The first inner arm 2100 includes a first inner surface 2106 and a first outer surface 2108 disposed opposite the first inner surface 2106. The first inner surface 2106 (shown more clearly in FIG. 13A) is positioned adjacent to the curved longitudinal axis 2001 and facing inwardly towards the curved longitudinal axis 2001. The first outer surface 2108 is positioned opposite the first inner surface 2106 with respect to the curved longitudinal axis 2001 and faces away from the curved longitudinal axis 2001. As shown, the first inner surface 2106 may be a planar surface having a linear profile when viewed from the top side or the bottom side of the device 2000.

The first inner arm 2100 further includes a concave surface 2110 positioned and extending between the first inner surface 2106 and the first outer surface 2108. The concave surface 2110 may be substantially perpendicular to each of the first inner surface 2106 and the first outer surface 2108. The concave surface 2110 is positioned to face the concave side of the curved longitudinal axis 2001 and the device 2000. The first inner arm 2100 further includes a convex surface 2112 positioned and extending between the first inner surface 2106 and the first outer surface 2108 (e.g., substantially perpendicular to each of the first inner surface 2106 and the 2108). The convex surface 2112 is positioned opposite from the concave surface 2110 such that the convex surface 2112 faces the convex side of the curved longitudinal axis 2001 and the device 2000. As shown, the concave surface 2110 has a concave profile when viewed from one of the lateral sides of the device 2000, and the convex surface 2112 has a convex profile when viewed from one of the lateral sides of the device 2000.

Similar to the first inner arm 2100, the second inner arm 2200 extends from a first end 2202 of the second inner arm 2200 to a second end 2204 of the second inner arm 2200 along the first direction. The second inner arm 2200 positioned adjacent to the first inner arm 2100 such that the first end 2202 of the second inner arm 2200 is positioned adjacent to the first end 2102 of the first inner arm 2100. Specifically, the second inner arm 2200 extends along the first direction substantially parallel and adjacent to the first inner arm 2100. The second inner arm 2200 is spaced apart from the first inner arm 2100 in a lateral or second direction that is substantially perpendicular to the curved longitudinal axis 2001.

The second inner arm 2200 includes a second inner surface 2206 and a second outer surface 2208 disposed opposite the second inner surface 2206. The second inner surface 2206 (shown more clearly in FIG. 13A) is positioned adjacent to the curved longitudinal axis 2001 and facing inwardly towards the 2001 and facing towards the first inner surface 2106 of the first inner arm 2100. The second outer surface 2208 is positioned opposite the second inner surface 2206 with respect to the curved longitudinal axis 2001 and faces away from the curved longitudinal axis 2001. As shown, the second inner surface 2206 may be a planar surface having a linear profile when viewed from the top side or the bottom side of the device 2000.

The second inner arm 2200 further includes a concave surface 2210 positioned and extending between the second inner surface 2206 and the second outer surface 2208. The concave surface 2210 may be substantially perpendicular to each of the second inner surface 2206 and the second outer surface 2208. The concave surface 2210 is positioned to face the concave side of the curved longitudinal axis 2001 and the device 2000. The second inner arm 2200 further includes a convex surface 2212 positioned and extending between the second inner surface 2206 and the second outer surface 2208 (e.g., substantially perpendicular to each of the second inner surface 2206 and the second outer surface 2208). The convex surface 2212 is positioned opposite from the concave surface 2210 such that the convex surface 2212 faces the convex side of the curved longitudinal axis 2001 and the device 2000. As shown, the concave surface 2210 has a concave profile when viewed from one of the lateral sides of the device 2000, and the convex surface 2212 has a convex profile when viewed from one of the lateral sides of the device 2000.

In particular, the shapes of the concave sides and the convex sides of the first inner arm 2100 and the second inner arm 2200 may better accommodate the shape of the base of the left atrial appendage in a manner that avoids a residual stump remaining un-occluded. According to various embodiments, the radius of curvature and the depth of curvature of the concave sides and the convex sides may be varied to better accommodate the anatomy of different subjects The first outer arm 2300 extends from a first end 2302 of the first outer arm 2300 to a second end 2304 of the first outer arm 2300 along the first direction. The first outer arm 2300 extends along the first direction with a curvature matching that of the curved longitudinal axis 2001, the first inner arm 2100, and the second inner arm 2200. The first outer arm 2300 is spaced outwardly apart from the first inner arm 2100 with respect to the curved longitudinal axis 2001. In other words, the first outer arm 2300 is spaced apart from the first inner arm 2100 in the second direction on a side of the first inner arm 2100 opposite from that of the second inner arm 2200.

The first end 2302 of the first outer arm 2300 is coupled to the second end 2104 of the first inner arm 2100. A first distal extent 2350 is defined on the first end 2302 of the first outer arm 2300 and on the second end 2104 of the first inner arm 2100 (e.g., at least partially comprising the connection between the first inner arm 2100 and the first outer arm 2300). The first distal extent 2350 extends at least partially in the second direction laterally away from the curved longitudinal axis 2001 (e.g., forming a wider surface 2352 on the concave surface of the first outer arm 2300 and the first inner arm 2100, as further described below).

The second outer arm 2400 extends from a first end 2402 of the second outer arm 2400 to a second end 2404 of the second outer arm 2400 along the first direction. The second outer arm 2400 extends along the first direction with a curvature matching that of the curved longitudinal axis 2001, the first inner arm 2100, the second inner arm 2200, and the first outer arm 2300. The second outer arm 2400 is spaced outwardly apart from the second inner arm 2200 with respect to the curved longitudinal axis 2001. In other words, the second outer arm 2400 is spaced apart from the second inner arm 2200 in the second direction on a side of the second inner arm 2200 opposite from that of the first inner arm 2100.

The first end 2402 of the second outer arm 2400 is coupled to the second end 2204 of the second inner arm 2200. A second distal extent 2450 is defined on the first end 2402 of the second outer arm 2400 and on the second end 2204 of the second inner arm 2200 (e.g., at least partially comprising the connection between the second inner arm 2200 and the second outer arm 2400). The second distal extent 2450 extends at least partially in the second direction laterally away from the curved longitudinal axis 2001 (e.g., forming a wider surface 2452 on the concave surface of the second outer arm 2400 and the second inner arm 2200, as further described below).

The first outer arm 2300 is also coupled to the second outer arm 2400 on the proximal or second end 2004 of the device 2000. The second end 2304 of the first outer arm 2300 opposite from the first distal extent 2350 is coupled to the second end 2404 of the second outer arm 2400 opposite from the second distal extent 2450. Specifically, the second end 2304 of the first outer arm 2300 is coupled to the second end 2404 of the second outer arm 2400 via a hinge portion 2500 extending therebetween. The hinge portion 2500 thus forms a connecting portion coupled to and integrally formed with each of the first outer arm 2300 and the second outer arm 2400.

The hinge portion 2500 includes a hinge outer surface 2502 and a hinge inner surface 2504 opposite from the hinge outer surface 2502. The hinge outer surface 2502 faces outwardly with respect to the device 2000 (e.g., in a proximal direction along the curved longitudinal axis 2001 away from the second end 2004). The hinge inner surface 2504 faces inwardly with respect to the device 2000 (e.g., in a distal direction along the curved longitudinal axis 2001 toward the second end 2004). Furthermore, the hinge inner surface 2504 of the hinge portion 2500 faces towards and is adjacent to each of the first end 2102 of the first inner arm 2100 and the first end 2202 of the second inner arm 2200.

The hinge portion 2500 extends across the curved longitudinal axis 2001 in substantially the second direction between the second end 2304 of the first outer arm 2300 and the second end 2404 of the second outer arm 2400. The hinge portion 2500 defines a curved portion 2510 that curves inwardly. Specifically, at the curved portion 2510 of the hinge portion 2500, each of the hinge outer surface 2502 and the hinge inner surface 2504 of the hinge portion 2500 curve inwardly towards the second end 2004 of the device 2000.

The first outer arm 2300, the second outer arm 2400, and the hinge portion 2500 are positioned "outside" of the first inner arm 2100 and the second inner arm 2200. For example, each of the first inner arm 2100 and the second inner arm 2200 are disposed closer to the curved longitudinal axis 2001 than each of the first outer arm 2300 and the second outer arm 2400. Additionally, the hinge portion 2500 is disposed further in the proximal direction that each of the first inner arm 2100 and the second inner arm 2200. Thus, the hinge inner surface 2504 of the hinge portion 2500 and each of the inwardly facing surfaces of the first outer arm 2300 and the second outer arm 2400 define an opening 2030 within which the first inner arm 2100 and the second inner arm 2200 are disposed. The opening 2030 may extend from the hinge inner surface 2504 on the first end 2002 of the device 2000 to the first end 2102 of the first inner arm 2100 and the first end 2202 of the second inner arm 2200 near the second end 2004 of the device 2000. The opening 2030 may be partially defined by a portion of the first distal extent 2350 and the second distal extent 2450 on the second end 2004 of the device 2000.

The device 2000 is generally movable between (i) a closed configuration and (ii) an open configuration, similar to other occlusion devices of the present disclosure. In the closed configuration (e.g., as shown in FIG. 11A), the second end 2104 of the first inner arm 2100 is spaced apart from the second end 2204 of the second inner arm 2200 by a first lateral distance in the second direction. In the closed configuration, the first inner arm 2100 is substantially parallel to the first outer arm 2300.

In the open configuration (e.g., as shown in FIG. 13A), the second end 2104 of the first inner arm 2100 is spaced apart from the second end 2204 of the second inner arm 2200 by a second lateral distance in the second direction that is greater than the first lateral distance. In the open configuration, the first inner arm 2100 is angled with respect to the first outer arm 2300. For example, each of the first inner surface 2106 of the first inner arm 2100 and the second inner surface 2206 of the second inner arm 2200 form an angle with respect to the curved longitudinal axis 2001 (e.g., an angle greater than 0 degrees and less than 90 degrees, such as 30 degrees).

The device 2000 is generally biased towards the closed configuration. The material properties of the device 2000 may inherently bias the device 2000 towards the closed configuration (e.g., wherein the device includes nitinol or other materials disclosed herein). The hinge portion 2500 biases the first inner arm 2100 and the first outer arm 2300 towards each other. Specifically, the hinge portion 2500 biases the second end 2304 of the first outer arm 2300 and the second end 2404 of the second outer arm 2400 towards each other (e.g., inwardly in the second direction, towards the curved longitudinal axis 2001). The hinge portion 2500 additionally biases each of the first distal extent 2350 and the second distal extent 2450 coupled to the first outer arm 2300 and the second outer arm 2400, respectively, towards the curved longitudinal axis 2001.

The device 2000 defines a plurality of suture holes configured to accept a thread or suture (e.g., to couple an adjacent sleeve or other connective device). For example, FIGS. 12A-12C show a device 2000 having a plurality of sleeves coupled to the device 2000 via the plurality of suture holes. While different numbers, arrangements, and sizes of suture holes are shown with respect to the device 2000, this disclosure contemplates different numbers, arrangements, and sizes of suture holes than what is shown. The suture holes shown in FIGS. 11A-12C are exemplary only. While different numbers, orientations, and configurations of sleeves are shown with respect to the device 2000, this disclosure contemplates different numbers, orientations, and configurations than what is shown. The sleeves shown in FIGS. 12A-12C are exemplary only.

The first end 2102 of the first inner arm 2100 defines at least one suture hole extending at least partially through the first inner arm 2100. Specifically, the first end 2102 of the first inner arm 2100 includes a first suture hole 2120 and a second suture hole 2122. Each of the first suture hole 2120 and the second suture hole 2122 extend from the concave surface 2110 to the convex surface 2112. In some implementations, the suture holes may extend in a third direction that is perpendicular to both the curved longitudinal axis and the second direction. In some implementations, the suture holes extend parallel to each other. However, in other implementations (not shown), the suture holes may extend only partially through the first inner arm (e.g., a tunnel-like structure both entering and exiting from the same surface). The first end 2202 of the second inner arm 2200 includes a third suture hole 2220 and a fourth suture hole 2222 that are substantially similar to the first suture hole 2120 and the second suture hole 2122 of the first inner arm 2100. It is understood that the labels for each of the suture holes (e.g., "first", "second", "third", etc.) are exemplary labels only, and any one of the suture holes of the device 2000 may be termed a "first suture hole" or a "second suture hole" regardless of its location on the device 2000.

The first distal extent 2350 on the second end 2004 of the device 2000 defines a set of suture holes. The set of suture holes on the first distal extent 2350 includes suture holes 2360a, 2360b, and 2360c each spaced apart from each other in a direction substantially parallel to the first direction. Each of the suture holes 2360a-2360c extends from the concave surface to the convex surface of the device 2000, similar to the suture holes 2120, 2122 of the first inner arm 2100. However, in other implementations (not shown), the suture holes may intersect with a different surface (e.g., a lateral surface of the first distal extent 2350 facing away from the curved longitudinal axis 2001). The second distal extent 2450 on the second end 2004 of the device 2000 defines a set of suture holes that includes suture holes 2460*a*, 2460*b*, and 2460*c*. Each of the suture holes 2460*a*-2460*c* are substantially similar to the suture holes 2360*a*-2360*c*.

FIGS. 12A-12C show the device 2000 with sleeves coupled to the device 2000 via the plurality of suture holes. In particular, the device 2000 of FIGS. 12A-12C includes a first sleeve 3100 coupled to the first inner arm 2100, a second sleeve 3200 coupled to the second inner arm 2200, a third sleeve 3300 coupled to the first outer arm 2300, and a fourth sleeve 3400 coupled to the second outer arm 2400. Each of the sleeves 3100-3400 are coupled to the device 2000 via a suture thread extending through the suture holes of the device 2000. For example, a suture thread (or other threaded material as elsewhere described in this disclosure) may extend through one or more holes in the sleeve material and through one or more holes of the device 2000.

The sleeve 3100 coupled to the first inner arm 2100 includes a sleeve material extending from the concave surface 2110 of the first end 2102 of the first inner arm 2100, around the first outer arm 2300, and to the convex surface 2112 of the first end 2102 of the first inner arm 2100. Thus, the sleeve 3100 defines a channel 3102 that encapsulates a portion of the first outer arm 2300. However, the channel 3102 is large enough to accommodate a surgical tool alongside the first outer arm 2300, as further described below. The channel 3102 extends from a proximal opening 3104 that is closer to the hinge portion 2500 to a distal opening 3106 that is closer to the second end 2004 of the device 2000 than the proximal opening 3104. Thus, the sleeve 3100 defines a channel 3102 having two open ends 3104, 3106.

The sleeve 3200 coupled to the second inner arm 2200 includes a sleeve material extending from the concave surface 2210 of the first end 2202 of the second inner arm 2200, around the second outer arm 2400, and to the convex surface 2212 of the first end 2202 of the second inner arm 2200. Thus, the sleeve 3200 defines a channel 3202 that encapsulates a portion of the second outer arm 2400. However, the channel 3202 is large enough to accommodate a surgical tool alongside the second outer arm 2400, as further described below. The channel 3202 extends from a proximal opening 3204 that is closer to the hinge portion 2500 to a distal opening 3206 that is closer to the second end 2004 of the device 2000 than the proximal opening 3204. Thus, the sleeve 3200 defines a channel 3202 having two open ends 3204, 3206.

The sleeve 3300 coupled to the first distal extent 2350 defines a channel 3302 that extends from an opening 3304 towards a closed end 3306 on the second end 2004 of the device 2000. Similarly, the sleeve 3400 coupled to the second distal extent 2450 defines a channel 3402 that extends from an opening 3404 towards a closed end 3406 on the second end 2004 of the device 2000. However, in other implementations, the sleeves 3300, 3400 may includes two open ends.

In practice, the sleeves 3100-3400 described above may be used to facilitate the movement of the device 2000 between the open and closed configurations. For example, as described with respect to the device 700 of FIGS. 7A-7D, a medical device or instrument (e.g., surgical clamps or a pair of forceps having two opposing tips) may be used along with the occlusion device 2000. The sleeves are sized to accept and retain the tips of the forceps, as shown in FIGS. 13A-13C. Specifically, a first tip of a first arm of the clamps is inserted (i) through the channel 3102 of the sleeve 3100 and (ii) into the channel 3302 of the third sleeve 3300.

Furthermore, a second tip of a second arm of the clamps is inserted (i) through the channel 3202 of the sleeve 3200 and (ii) into the channel 3402 of the third sleeve 3300.

Once the tip of the clamps is engaged with the sleeves 3100-3400 coupled to the device 2000, movement of the clamps will move the device 2000 in a corresponding direction. For example, opening the tips of the clamps to move away from each other will move the device 2000 from the closed configuration to the open configuration, as shown in FIG. 13A. As elsewhere described, such opening movement facilitates implanting the device 2000 with respect to a tissue (e.g., the left atrial appendage).

A user (e.g., a medical professional), may couple each of the fabric sleeves 3100-3400 to the device 2000 via suture thread. Then, a user may couple the first and second arms of the clamps to the device 2000 via insertion into the channels defined by the sleeves 3100-3400. Then, the user may move the device 2000 from the closed configuration to the open configuration wherein the first and second inner arms 2100, 2200 are spaced apart from each other, thus holding the device 2000 against the biasing force. Then, a user may implant the device 2000 such that each of the first inner arm 2100 and the second inner arm 2200 are disposed on either side of a tissue (e.g., the left atrial appendage). Then, a user may release the device 2000 to move back towards the open configuration to encapsulate and/or occlude the tissue, which may be the deployed configuration. FIGS. 14A and 14B show a surgical application of the device 2000 wherein the device 2000 is implanted on a left atrial appendage, according to one implementation.

FIGS. 13B and 13C shows a different medical instrument, shown as clamps 3500, engaged with the device 2000 and the sleeves 3100-3400 coupled thereto. FIG. 13B shows the closed configuration, and FIG. 13C shows the open configuration with a user engaging the clamps. FIGS. 13B-13C additionally show a retention device 3600. In general, the clamps 3500 are coupled to the retention device 3600 to limit and/or guide the opening of the clamps 3500. In some situations, the maximum distance between the free tips of the clamps 3500 in the open configuration is too large. For example, for certain surgical applications, a narrow anatomical space requires the clamps 3500 to limit their total expansion (i.e., the maximum distance or range of motion of the clamps 3500 is larger than the distance allowed for the surgical situation). In other situations, the device 2000 cannot be moved in certain directions or configurations. For example, the device 2000 for a surgical procedure may need to be implanted without over-expanding device 2000 (e.g., without over-stretching the hinge portion 2500). Therefore, retention device 3600 limits the travel of the arms of the clamps 3500, thus limiting the opening capacity of the device 2000.

Section IV. Example Removable Sleeves

FIGS. 15A-15C show exemplary layouts for sleeves and/or pockets that are removably couplable to an occlusion device or clamp of this disclosure. The layouts shown in FIGS. 15A-15C are foldable and/or compliant cloth. The sleeves shown in FIGS. 15A-15C are shown in a flat configuration and an assembled configuration. The sleeve configurations of FIGS. 15A-15C are exemplary only, a user (e.g., a medical professional) may fashion a different type of sleeve having a different configuration which may also function with the devices of the present disclosure.

FIG. 15A shows the device 2000 of FIG. 13A with the attached sleeves 3100-3400. FIG. 15A shows a sleeve layout

4100 and a sleeve layout 4200, each corresponding to a different sleeve coupled to the device 2000.

The sleeve layout 4100 corresponds to one or both of the sleeves 3100, 3200 (e.g., a linear sleeve layout forming an open channel). The sleeve layout 4100 includes a substantially rectangular main portion 4110 extending from a first end 4102 to a second end 4104. A set of grommets or through holes 4106 extend through the main portion 4110 on the first end 4102. A set of grommets or through holes 4108 extend through the main portion 4110 on the second end 4104. The attachment of the sleeve layout 4100 is fairly straightforward. The first end 4102 is positioned over one set of suture holes on either the first inner arm 2100 or the second inner arm 2200 (e.g., a concave side), and the second end 4104 is positioned over the other side of the same inner arm (e.g., a convex side). A suture is threaded through each of the through holes 4106, 4108 and through the corresponding suture holes on the first inner arm 2100 or the second inner arm 2200. A knot is tied as needed, securing the sleeve 3100 to the device 2000.

The sleeve layout 4200 corresponds to one or both of sleeves 3300, 3400 (e.g., a closed-end sleeve layout). The sleeve layout 4200 includes a main portion 4210 and a secondary portion 4220 extending from the main portion 4210. The sleeve layout 4200 includes a first side 4202 and a second side 4204. The main portion 4210 includes a first set of grommets or through holes 4206 on the first side 4202 and a second set of grommets or through holes 4208 on the second side 4204. Furthermore, the secondary portion 4220 includes a first through hole 4222 on the first side 4202 and a second through hole 4224 on the second side 4204.

To form the sleeve 3300 from the 4200 and couple the third sleeve 3300 to the device 2000, the first side 4202 is positioned on the concave or convex side of the first distal extent 2350. The through holes 4206 are aligned with the suture holes 2630a-2360c. The second side 4204 of the sleeve layout 4200 is wrapped around to the opposing convex or concave side of the first distal extent 2350, and the through holes 4206 are aligned with the opposing end of the suture holes 2630a-2360c. Then, the secondary portion 4220 is folded over to form the closed end 3306 of the third sleeve 3300. The through holes 4222, 4224 are aligned with one of the suture holes 2360a-2360c (e.g., the distalmost suture hole) to overlap part of the main portion 4110. Then, a suture is threaded through each of the through holes 4206, 4208, 4222, and 4224 and through the corresponding suture holes on the first distal extent 2350. A knot is tied as needed, securing the sleeve 3300 to the device 2000.

FIG. 15B shows another implementation of a sleeve layout in a flat configuration and an assembled configuration. The sleeve layout 4300 of FIG. 15B forms a square pocket 4301 shown adjacent to the sleeve layout 4300. In the flat configuration, a series of longitudinal folds separate the sleeve layout 4300 into five sections. Each section on the side of the sleeve layout 4300 includes the grommets or through holes. The middle section includes a connector or end-cap piece configured to form the closed second end.

The sleeve layout 4300 is either placed on—or assembled while disposed on—a clamping portion/arm of an occlusion device. When moved to the assembled configuration, each section is folded at a substantially right angle with respect to each other to form the square-shaped pocket 4301. Sutures are threaded through the grommets or through holes to secure the structure of the shape of the pocket 4301 and to couple the pocket 4301 to the clamping arm.

FIG. 15C shows another implementation of a sleeve layout in a flat configuration and an assembled configuration. The sleeve layout 4400 of FIG. 15C forms a rounded pocket 4401 shown adjacent to the sleeve layout 4400. The rounded pocket 4401 is formed in a substantially similar manner as the pocket 4301.

In other implementations, a variety of geometries, shapes, folds, and connection points of the pocket are contemplated by this disclosure. The pockets 4301, 4401 comprise woven polyester. However, in other implementations, the pockets may comprise Dacron cloth, PTFE, mesh materials, and/or any pliable and biocompatible material that may be used to form the pockets.

Although specific embodiments of the disclosure have been described, one of ordinary skill in the art will recognize that numerous other modifications and alternative embodiments are within the scope of the disclosure. For example, while various illustrative implementations and structures have been described in accordance with embodiments of the disclosure, one of ordinary skill in the art will appreciate that numerous other modifications to the illustrative implementations and structures described herein are also within the scope of this disclosure. Throughout this disclosure, a dimension shown in the drawings or described in the specification is merely exemplary and does not limit the structure or function of the disclosed device(s).

Although embodiments have been described in language specific to structural features and/or methodological acts, it is to be understood that the disclosure is not necessarily limited to the specific features or acts described. Rather, the specific features and acts are disclosed as illustrative forms of implementing the embodiments. Conditional language, such as, among others, "can," "could," "might," or "may," unless specifically stated otherwise, or otherwise understood within the context as used, is generally intended to convey that certain embodiments could include, while other embodiments do not include, certain features, elements, and/or steps. Thus, such conditional language is not generally intended to imply that features, elements, and/or steps are in any way required for one or more embodiments.

Exemplary Aspects

In view of the described processes and compositions, hereinbelow are described certain more particularly described aspects of the disclosures. These particularly recited aspects should not, however, be interpreted to have any limiting effect on any different claims containing different or more general teachings described herein, or that the "particular" aspects are somehow limited in some way other than the inherent meanings of the language and formulas literally used therein.

Example 1. An occlusion device for occluding a hollow tissue structure of a living subject, wherein the hollow tissue structure is a left atrial appendage extending from a lateral wall of a left atrium of a heart, the occlusion device comprising: a first clamping portion configured for positioning along a first side of the left atrial appendage; and a second clamping portion movably connected to the first clamping portion on a first end of the occlusion device and configured for positioning along an opposite second side of the left atrial appendage while the first clamping portion is positioned along the first side; wherein the first clamping portion and the second clamping portion each comprise: an inner side configured to face toward the left atrial appendage when the occlusion device is in a deployed configuration; an outer side disposed opposite the inner side and configured to face away from the left atrial appendage when the occlusion device is in the deployed configuration; and at least one sleeve, including a first sleeve coupled to and extending from the outer side of the first clamping portion, the first sleeve defining a first opening on a first end of the first sleeve and a first channel extending from the first opening towards a second end of the first sleeve.

Example 2. The occlusion device according to any example herein, particularly Example 1, wherein the second end of the first sleeve defines a second opening of the first sleeve.

Example 3. The occlusion device according to any example herein, particularly Examples 1-2, wherein the first channel is frustoconical in shape and has a narrowing diameter from the first end to the second end of the first sleeve.

Example 4. The occlusion device according to any example herein, particularly Examples 1-3, wherein the second end of the first sleeve is closed.

Example 5. The occlusion device according to any example herein, particularly Examples 1-4, wherein the first end of the first sleeve is closer to the first end of the occlusion device than an opposite second end of the occlusion device.

Example 6. The occlusion device according to any example herein, particularly Examples 1-4, wherein the first end of the first sleeve is closer to an opposite second end of the occlusion device than the first end of the occlusion device.

Example 7. The occlusion device according to any example herein, particularly Examples 1-6, wherein the at least one sleeve further comprises: a second sleeve coupled to and extending from the outer side of the second clamping portion, the second sleeve defining a first opening of the second sleeve on a first end of the second sleeve and a second channel extending from the first opening towards a second end of the second sleeve.

Example 8. The occlusion device according to any example herein, particularly Example 7, wherein the second end of the second sleeve defines a second opening of the second sleeve.

Example 9. The occlusion device according to any example herein, particularly Examples 8-9, wherein the second channel is frustoconical in shape and has a narrowing diameter from the first end to the second end of the second sleeve.

Example 10. The occlusion device according to any example herein, particularly Examples 7-9, wherein the second end of the second sleeve is closed.

Example 11. The occlusion device according to any example herein, particularly Examples 7-10, wherein the first end of the second sleeve is closer to the first end of the occlusion device than an opposite second end of the occlusion device.

Example 12. The occlusion device according to any example herein, particularly Examples 7-10, wherein the first end of the second sleeve is closer to an opposite second end of the occlusion device from the first end of the occlusion device.

Example 13. The occlusion device according to any example herein, particularly Examples 1-12, wherein the first opening of the first sleeve and the first opening of the second sleeve are configured to accept a tip of a medical instrument to facilitate moving the first clamping portion away from or towards the second clamping portion.

Example 14. The occlusion device according to any example herein, particularly Examples 1-13, wherein the medical instrument is a pair of forceps.

Example 15. The occlusion device according to any example herein, particularly Examples 1-14, wherein the first clamping portion and the second clamping portion further comprise: a concave side configured to face away from the lateral wall when the occlusion device is in the deployed configuration; and a convex side disposed opposite the concave side and configured to face toward the lateral wall when the occlusion device is in the deployed configuration.

Example 16. The occlusion device according to any example herein, particularly Examples 1-15, further comprising a connecting portion connected to the first clamping portion and the second clamping portion and positioned at the first end of the occlusion device, wherein the second clamping portion is movably connected to the first clamping portion via the connecting portion.

Example 17. The occlusion device according to any example herein, particularly Example 16, wherein the second clamping portion and the first clamping portion are not connected to one another at the opposite second end of the occlusion device.

Example 18. The occlusion device according to any example herein, particularly Examples 1-16, wherein the occlusion device is configured to transition between an open configuration and a closed configuration.

Example 19. The occlusion device according to any example herein, particularly Examples 16-18, wherein the connecting portion is configured to bias the occlusion device toward the closed configuration.

Example 20. The occlusion device according to any example herein, particularly Examples 16-19, wherein the connecting portion comprises a hinge.

Example 21. The occlusion device according to any example herein, particularly Examples 1-20, wherein the second clamping portion and the first clamping portion are configured to pivot relative to one another as the occlusion device is transitioned between the open configuration and the closed configuration.

Example 22. The occlusion device according to any example herein, particularly Examples 1-21, further comprising: a first connecting portion connected to the first clamping portion and the second clamping portion and positioned at a first end of the occlusion device; and a second connecting portion connected to the first clamping portion and the second clamping portion and positioned at an opposite second end of the occlusion device; wherein the second clamping portion is movably connected to the first clamping portion via the first connecting portion and the second connecting portion.

Example 23. The occlusion device according to any example herein, particularly Example 22, wherein the first clamping portion, the second clamping portion, the first connecting portion, and the second connecting portion form an enclosed loop defining an opening configured to receive the left atrial appendage therethrough.

Example 24. The occlusion device according to any example herein, particularly Examples 1-23, wherein the occlusion device is configured to transition between an open configuration and a closed configuration.

Example 25. The occlusion device according to any example herein, particularly Examples 22-24, wherein the first connecting portion and the second connecting portion are configured to bias the occlusion device toward the closed configuration.

Example 26. The occlusion device according to any example herein, particularly Examples 22-25, wherein the first connecting portion and the second connecting portion each have a curved shape.

Example 27. The occlusion device according to any example herein, particularly Examples 1-26, wherein the second clamping portion and the first clamping portion are configured to translate relative to one another as the occlusion device is transitioned between the open configuration and the closed configuration.

Example 28. The occlusion device according to any example herein, particularly Examples 1-27, wherein the inner side comprises a planar surface having a linear profile viewed from a top side or a bottom side of the occlusion device.

Example 29. The occlusion device according to any example herein, particularly Examples 1-29, wherein the inner side comprises a contoured surface having a contoured profile viewed from a top side or a bottom side of the occlusion device.

Example 30. The occlusion device according to any example herein, particularly Examples 1-29, wherein the first sleeve is curved along a longitudinal axis of the first sleeve to match either one of the convex side and the convex side of the first clamping portion.

Example 31. The occlusion device according to any example herein, particularly Examples 1-30, wherein the first sleeve is linear from the first end to the second end of the first sleeve such that a longitudinal axis of the first sleeve is transverse to either one of the convex side and the convex side of the first clamping portion.

Example 32. The occlusion device according to any example herein, particularly Examples 1-31, wherein the concave side comprises a concave surface having a concave profile viewed from a lateral side of the occlusion device.

Example 33. The occlusion device according to any example herein, particularly Example 32, wherein the concave surface extends along at least a majority of a length of the first or second clamping portion.

Example 34. The occlusion device according to any example herein, particularly Examples 32-33, wherein the concave surface extends along an entirety of the length of the first or second clamping portion.

Example 35. The occlusion device according to any example herein, particularly Examples 1-34, wherein the convex side comprises a convex surface having a convex profile viewed from a lateral side of the occlusion device.

Example 36. The occlusion device according to any example herein, particularly Example 35, wherein the convex surface extends along at least a majority of a length of the first or second clamping portion.

Example 37. The occlusion device according to any example herein, particularly Examples 35-36, wherein the convex surface extends along an entirety of the length of the first or second clamping portion.

Example 38. The occlusion device according to any example herein, particularly Examples 1-37, further comprising a fabric covering extending over at least a portion of each of the first clamping portion and the second clamping portion.

Example 39. The occlusion device according to any example herein, particularly Example 38, wherein the fabric covering extends over at least a portion of each of the inner side, the outer side, the concave side, and the convex side.

Example 40. A method for occluding a hollow tissue structure of a living subject, wherein the hollow tissue structure is a left atrial appendage extending from a lateral wall of a left atrium of a heart, the method comprising: causing an occlusion device to transition from a closed configuration to an open configuration, wherein the occlusion device comprises a first clamping portion and a second clamping portion movably connected to the first clamping portion, and wherein the first clamping portion and the second clamping portion each comprise: an inner side; an outer side disposed opposite the inner side; and a first sleeve coupled to and extending from the outer side of the first clamping portion and a second sleeve coupled to and extending from the outer side of the second clamping portion; positioning the occlusion device relative to the left atrial appendage such that the first clamping portion is positioned along a first side of the left atrial appendage and the second clamping portion is positioned along an opposite second side of the left atrial appendage; and causing the occlusion device to transition from the open configuration to a deployed configuration in which the occlusion device occludes the left atrial appendage, wherein, when the occlusion device is in the deployed configuration, the inner sides of the first clamping portion and the second clamping portion each face toward the left atrial appendage, the outer sides of the first clamping portion and the second clamping portion each face away from the left atrial appendage.

Example 41. The method according to any example herein, particularly Example 40, wherein the first clamping portion and the second clamping portion of the occlusion device each further comprise a concave side and a convex side, wherein, when the occlusion device is in the deployed configuration, the concave sides of the first clamping portion and the second clamping portion each face away from the lateral wall of the left atrium of the heart, and the convex sides of the first clamping portion and the second clamping portion each face toward the lateral wall of the left atrium of the heart.

Example 42. The method according to any example herein, particularly Examples 40-41, wherein causing the occlusion device to transition between the closed configuration and the open configuration comprises inserting a first tip of a pair of forceps into the first sleeve and inserting a second tip of the pair of forceps into the second sleeve, the first and second tip of the forceps being selectively movable apart from and towards each other.

Example 43. The method according to any example herein, particularly Examples 40-42, wherein the occlusion device further comprises a connecting portion connected to the first clamping portion and the second clamping portion and positioned at a first end of the occlusion device, wherein the second clamping portion is movably connected to the first clamping portion via the connecting portion.

Example 44. The method according to any example herein, particularly Example 43, wherein the second clamping portion and the first clamping portion are not connected to one another at an opposite second end of the occlusion device.

Example 45. The method according to any example herein, particularly Examples 40-44, wherein causing the occlusion device to transition from the closed configuration to the open configuration comprises causing the first clamping portion and the second clamping portion to pivot away from one another.

Example 46. The method according to any example herein, particularly Examples 40-45, wherein the connecting portion is configured to bias the occlusion device toward the closed configuration.

Example 47. The method according to any example herein, particularly Examples 40-46, wherein causing the occlusion device to transition from the closed configuration to the open configuration comprises applying an external force to the occlusion device to overcome a biasing force provided by the connecting portion.

Example 48. The method according to any example herein, particularly Examples 40-47, wherein causing the occlusion device to transition from the open configuration to the deployed configuration comprises removing the external force.

Example 49. The method according to any example herein, particularly Examples 40-48, wherein causing the occlusion device to transition from the open configuration to the deployed configuration comprises allowing the connecting portion to bias the occlusion device to the deployed configuration.

Example 50. The method according to any example herein, particularly Examples 40-49, wherein the connecting portion comprises a hinge.

Example 51. The method according to any example herein, particularly Example 40, wherein the occlusion device further comprises: a first connecting portion connected to the first clamping portion and the second clamping portion and positioned at a first end of the occlusion device; and a second connecting portion connected to the first clamping portion and the second clamping portion and positioned at an opposite second end of the occlusion device; wherein the second clamping portion is movably connected to the first clamping portion via the first connecting portion and the second connecting portion.

Example 52. The method according to any example herein, particularly Example 50, wherein the first clamping portion, the second clamping portion, the first connecting portion, and the second connecting portion form an enclosed loop defining an opening, and wherein positioning the occlusion device relative to the left atrial appendage comprises positioning the occlusion device such that the left atrial appendage is received through the opening.

Example 53. The method according to any example herein, particularly Examples 50-51, wherein causing the occlusion device to transition from the closed configuration to the open configuration comprises causing the first clamping portion and the second clamping portion to translate away from one another.

Example 54. The method according to any example herein, particularly Examples 50-53, wherein the first connecting portion and the second connecting portion are configured to bias the occlusion device toward the closed configuration.

Example 55. The method according to any example herein, particularly Examples 50-54, wherein causing the occlusion device to transition from the closed configuration to the open configuration comprises applying an external force to the occlusion device to overcome a biasing force provided by the first connecting portion and the second connecting portion.

Example 56. The method according to any example herein, particularly Example 55, wherein causing the occlusion device to transition from the open configuration to the deployed configuration comprises removing the external force.

Example 57. The method according to any example herein, particularly Examples 50-56, wherein causing the occlusion device to transition from the open configuration to the deployed configuration comprises allowing the first connecting portion and the second connecting portion to bias the occlusion device to the deployed configuration.

Example 58. The method according to any example herein, particularly Examples 40-57, wherein causing the occlusion device to transition between the closed configuration and the open configuration comprises inserting a first tip of a pair of forceps into the first sleeve and inserting a second tip of the pair of forceps into the second sleeve, the first and second tip of the forceps being selectively movable apart from and towards each other.

Example 59. The method according to any example herein, particularly Example 51, wherein the first connecting portion and the second connecting portion each have a curved shape.

Example 60. The method according to any example herein, particularly Example 51, wherein causing the occlusion device to transition from the closed configuration to the open configuration comprises causing the first clamping portion and the second clamping portion to pivot away from one another.

Example 61. The method according to any example herein, particularly Examples 40-60, wherein the first sleeve is curved along a longitudinal axis of the first sleeve to match either one of the convex side and the convex side of the first clamping portion.

Example 62. The occlusion device according to any example herein, particularly Examples 1-61, wherein the first sleeve is linear from the first end to the second end of the first sleeve such that a longitudinal axis of the first sleeve is transverse to either one of the convex side and the convex side of the first clamping portion.

Example 63. The method according to any example herein, particularly Examples 1-62, wherein the occlusion device further comprises a fabric covering extending over at least a portion of each of the first clamping portion and the second clamping portion.

Example 64. The method according to any example herein, particularly Example 63, wherein the fabric covering extends over at least a portion of each of the inner side, the outer side, the concave side, and the convex side.

Example 65. A system comprising: an occlusion device disclosed herein; and a pair of forceps having opposing tips, wherein the first sleeve of the device is configured to accept a tip of the forceps.

Example 66. An occlusion device for occluding a hollow tissue structure of a living subject, the occlusion device comprising: a first inner arm extending from a first end to a second end along a first direction parallel to a curved longitudinal axis of the occlusion device; a second inner arm extending from a first end to a second end along the first direction, the second inner arm being adjacent to first inner arm in a second direction that is perpendicular to the curved longitudinal axis; a first outer arm extending from a first end to a second end along the first direction, the first end of the first outer arm being coupled to the second end of the first inner arm to define a first distal extent at a distal end of the occlusion device, wherein the first outer arm is spaced apart from the first inner arm in the second direction on a side of the first inner arm opposite of the second inner arm; and a second outer arm extending from a first end to a second end along the first direction, the first end of the second outer arm being coupled to the second end of the second inner arm to define a second distal extent at the distal end of the occlusion device, wherein the second outer arm is spaced apart from the second inner arm in the second direction on a side of the second inner arm opposite of the first inner arm; wherein the second end of the first outer arm is coupled to the second end of the second outer arm at a proximal end of the occlusion device via a hinge portion, and wherein each of the first outer arm, the second outer arm, and the hinge portion define an opening within which the first inner arm and the second inner arm are disposed.

Example 67. The occlusion device according to any example herein, particularly Example 66, wherein the first inner arm includes a first inner surface configured for positioning along a first side of the hollow tissue structure, and the second inner arm includes a second inner surface configured for positioning along a second side of the hollow tissue structure, wherein the first inner surface is arranged parallel to the second inner surface on either side of the curved longitudinal axis.

Example 68. The occlusion device according to any example herein, particularly Examples 66-67, wherein the inner surfaces of each of the first and second inner arms comprise a planar surface having a linear profile viewed from a top side or a bottom side of the occlusion device.

Example 69. The occlusion device according to any example herein, particularly Examples 66-68, wherein the hinge portion biases the first and second distal extents, including the second ends of the first and second inner arms, inwardly towards the curved longitudinal axis.

Example 70. The occlusion device according to any example herein, particularly Examples 66-69, wherein the first end of the first inner arm and the first end of the second inner arm are biased inwardly towards each other.

Example 71. The occlusion device according to any example herein, particularly Examples 66-70, wherein the occlusion device is moveable between: (i) a closed configuration wherein the second end of the first inner arm is spaced apart from the second end of the second inner arm by a first lateral distance, and (ii) an open configuration wherein the second end of the first inner arm is spaced apart from the second end of the second inner arm by a second lateral distance that is greater than the first lateral distance.

Example 72. The occlusion device according to any example herein, particularly Examples 66-71, wherein, in the closed configuration, the first inner arm is substantially parallel to the second inner arm, and, in the open configuration, the first inner arm is angled with respect to the second inner arm.

Example 73. The occlusion device according to any example herein, particularly Examples 66-72, wherein the occlusion device is biased towards the closed configuration.

Example 74. The occlusion device according to any example herein, particularly Examples 66-73, wherein the occlusion device and the curved longitudinal axis thereof defines a concave side of the occlusion device and a convex side of the occlusion device opposite from the concave side.

Example 75. The occlusion device according to any example herein, particularly Example 74, wherein the concave side comprises a concave surface having a concave profile viewed from a lateral side of the occlusion device.

Example 76. The occlusion device according to any example herein, particularly Examples 66-75, wherein the hollow tissue structure is a left atrial appendage extending from a lateral wall of a left atrium of a heart.

Example 77. The occlusion device according to any example herein, particularly Examples 66-76, wherein the occlusion device comprises nitinol.

Example 78. The occlusion device according to any example herein, particularly Examples 66-77, wherein the first end of the first inner arm defines at least one suture hole extending at least partially through the first inner arm, and the second end of the second inner arm defines at least one suture hole extending at least partially through the second inner arm.

Example 79. The occlusion device according to any example herein, particularly Examples 66-78, wherein the first distal extent defines at least one suture hole extending at least partially through the occlusion device, and the second distal extent defines at least one suture hole extending at least partially through the occlusion device.

Example 80. The occlusion device according to any example herein, particularly Examples 66-79, further comprising: a first suture hole defined by and extending at least partially through the first end of the first inner arm; a second suture hole defined by and extending at least partially through the second end of the second inner arm; a third suture hole defined by and extending at least partially through the first distal extent adjacent the second end of the first inner arm; and a fourth suture hole defined by and extending at least partially through the second distal extent adjacent to the second end of the second inner arm.

Example 81. A system comprising: the occlusion device according to any example herein, particularly Example 80; a first sleeve defining a first channel, the first sleeve coupled to the first suture hole; and a second sleeve defining a second channel, the second sleeve coupled to the second suture hole.

Example 82. The system according to any example herein, particularly Example 80, further comprising: a third sleeve defining a third channel, the third sleeve coupled to the third suture hole; and a fourth sleeve defining a fourth channel, the fourth sleeve coupled to the fourth suture hole.

Example 83. The system according to any example herein, particularly Examples 81-80, wherein each of the first, second, third, and fourth channels are configured to accept a portion of a medical instrument.

Example 84. The system according to any example herein, particularly Examples 81-83, wherein the medical instrument is a surgical clamp.

Example 85. The system according to any example herein, particularly Examples 81-84, wherein the medical instrument facilitates movement of the occlusion device between a closed configuration and an open configuration.

Example 86. The system according to any example herein, particularly Examples 81-85, wherein each of the first and third channels extend in the second direction laterally away from the first outer arm.

Example 87. A method of using an occlusion device, the method comprising: (1) providing an occlusion device comprising: a first inner arm extending from a first end to a second end along a first direction parallel to a curved longitudinal axis of the occlusion device; a second inner arm extending from a first end to a second end along the first direction, the second inner arm being adjacent to first inner arm in a second direction that is perpendicular to the curved longitudinal axis; a first outer arm extending from a first end to a second end along the first direction, the first end of the first outer arm being coupled to the second end of the first inner arm to define a first distal extent at a distal end of the occlusion device, wherein the first outer arm is spaced apart from the first inner arm in the second direction on a side of the first inner arm opposite of the second inner arm; and a second outer arm extending from a first end to a second end along the first direction, the first end of the second outer arm being coupled to the second end of the second inner arm to define a second distal extent at the distal end of the occlusion device, wherein the second outer arm is spaced apart from the second inner arm in the second direction on a side of the second inner arm opposite of the first inner arm; wherein the second end of the first outer arm is coupled to the second end of the second outer arm at a proximal end of the occlusion device via a hinge portion, and wherein each of the first outer arm, the second outer arm, and the hinge portion define an opening within which the first inner arm and the second inner arm are disposed; (2) coupling a first arm of a medical instrument to at least a first suture hole defined by and extending at least partially through the first distal extent of the occlusion device; (3) coupling a second arm of the medical instrument to at least a second suture hole defined by and extending at least partially through the first distal extent of the occlusion device, wherein the second arm of the medical instrument is hingably coupled to the first arm of the medical instrument; and (4) moving the occlusion device from (i) a closed configuration wherein the second end of the first inner arm is spaced apart from the second end of the second inner arm by a first lateral distance, to (ii) an open configuration, wherein the second end of the first inner arm is spaced apart from the second end of the second inner arm by a second lateral distance that is greater than the first lateral distance.

Example 88. The method according to any example herein, particularly Example 87, wherein moving the device between the closed configuration and the open configuration comprises pivoting the first arm of the medical instrument with respect to the second arm of the medical instrument.

Example 89. The method according to any example herein, particularly Examples 87-88, wherein, in the closed configuration, the first inner arm is substantially parallel to the second inner arm, and, in the open configuration, the first inner arm is angled with respect to the second inner arm.

Example 90. The method according to any example herein, particularly Examples 87-89, further comprising: coupling the first arm of the medical instrument to at least a first suture hole defined by and extending at least partially through the first end of the first inner arm of the occlusion device; and coupling the second arm of the medical instrument to at least a second suture hole defined by and extending at least partially through the first end of the second inner arm of the occlusion device.

Example 91. The method according to any example herein, particularly Examples 87-90, wherein the hinge portion biases the first and second distal extents, including the second ends of the first and second inner arms, inwardly towards the curved longitudinal axis.

Example 92. The method according to any example herein, particularly Examples 87-91, wherein the first end of the first inner arm and the first end of the second inner arm are biased inwardly towards each other.

Example 93. The method according to any example herein, particularly Examples 87-92, wherein the medical instrument is a surgical clamp.

Example 94. The method according to any example herein, particularly Examples 87-93, further comprising: coupling a first sleeve defining a first channel to at least the first suture hole, wherein coupling the first arm of the medical instrument to the first suture hole includes inserting a portion of the first arm into the first channel of the first sleeve.

Example 95. The method according to any example herein, particularly Example 94, further comprising: coupling a second sleeve defining a second channel to at least the second suture hole, wherein coupling the second arm of the medical instrument to the second suture hole includes inserting a portion of the second arm into the second channel of the second sleeve.

Example 96. A method for occluding a hollow tissue structure, the method comprising: (1) moving an occlusion device from a closed configuration to an open configuration, wherein the occlusion device comprises: a first inner arm extending from a first end to a second end along a first direction parallel to a curved longitudinal axis of the occlusion device, the first inner arm having an inner surface and an outer surface opposite the inner surface; a second inner arm extending from a first end to a second end along the first direction, the second inner arm having an inner surface and an outer surface opposite the inner surface, wherein the second inner arm is adjacent to first inner arm in a second direction that is perpendicular to the curved longitudinal axis; a first outer arm extending from a first end to a second end along the first direction, the first end of the first outer arm being coupled to the second end of the first inner arm to define a first distal extent at a distal end of the occlusion device, wherein the first outer arm is spaced apart from the first inner arm in the second direction on a side of the first inner arm opposite of the second inner arm; and a second outer arm extending from a first end to a second end along the first direction, the first end of the second outer arm being coupled to the second end of the second inner arm to define a second distal extent at the distal end of the occlusion device, wherein the second outer arm is spaced apart from the second inner arm in the second direction on a side of the second inner arm opposite of the first inner arm, wherein the second end of the first outer arm is coupled to the second end of the second outer arm at a proximal end of the occlusion device via a hinge portion, and wherein each of the first outer arm, the second outer arm, and the hinge portion define an opening within which the first inner arm and the second inner arm are disposed, and wherein the occlusion device and the curved longitudinal axis thereof defines a concave side of the occlusion device and a convex side of the occlusion device opposite from the concave side; (2) positioning the occlusion device relative to the hollow tissue structure such that the first inner arm is positioned along a first side of the hollow tissue structure and the second inner arm is positioned along an opposite second side of the hollow tissue structure; and (3) causing the occlusion device to transition from the open configuration toward the closed configuration in which the occlusion device occludes the hollow tissue structure, wherein, when the occlusion device is in the closed configuration, the inner surface of the first inner arm and the inner surface of the second inner arm each face toward the hollow tissue structure.

Example 97. The method according to any example herein, particularly Example 96, wherein in the closed configuration, the second end of the first inner arm is spaced apart from the second end of the second inner arm by a first lateral distance, and in the open configuration, the second end of the first inner arm is spaced apart from the second end of the second inner arm by a second lateral distance that is greater than the first lateral distance.

Example 98. The method according to any example herein, particularly Examples 96-97, wherein causing the occlusion device to transition from the closed configuration to the open configuration comprises causing the second end of the first inner arm and the second end of the second inner arm to pivot away from one another.

Example 99. The method according to any example herein, particularly Examples 96-98, wherein causing the second end of the first inner arm and the second end of the second inner arm to pivot away from one another comprises pivoting the a arm of a medical instrument with respect to a second arm of a medical instrument.

Example 100. The method according to any example herein, particularly Examples 96-99, wherein the medical instrument is a surgical clamp.

Example 101. The method according to any example herein, particularly Examples 96-100, wherein the hinge portion biases the first and second distal extents, including the second ends of the first and second inner arms, inwardly towards the curved longitudinal axis.

Example 102. The method according to any example herein, particularly Examples 96-101, wherein the first end of the first inner arm and the first end of the second inner arm are biased inwardly towards each other.

Example 103. The method according to any example herein, particularly Examples 96-102, wherein the outer surface of the first inner arm and the outer surface of the second inner arm each face away from the hollow tissue structure, the concave side of the occlusion device faces away from the lateral wall, and the convex surface of the occlusion device faces toward the lateral wall.

In view of the many possible aspects to which the principles of the disclosed disclosure can be applied, it should be recognized that the illustrated aspects are only preferred examples of the disclosure and should not be taken as limiting the scope of the disclosure. Rather, the scope of the disclosure is defined by the following claims. We, therefore, claim as our disclosure all that comes within the scope and spirit of these claims.

What is claimed is:

1. An occlusion device for occluding a hollow tissue structure of a living subject, the occlusion device comprising:

a first inner arm extending from a first end to a second end along a first direction parallel to a central longitudinal axis of the occlusion device;

a second inner arm extending from a first end to a second end along the first direction, the second inner arm being adjacent to first inner arm in a second direction that is perpendicular to the central longitudinal axis;

a first outer arm extending from a first end to a second end along the first direction, the first end of the first outer arm being coupled to the first end of the first inner arm to define a first distal extent at a distal end of the occlusion device, wherein the first outer arm is spaced apart from the first inner arm in the second direction on a side of the first inner arm opposite of the second inner arm;

a second outer arm extending from a first end to a second end along the first direction, the first end of the second outer arm being coupled to the first end of the second inner arm to define a second distal extent at the distal end of the occlusion device, wherein the second outer arm is spaced apart from the second inner arm in the second direction on a side of the second inner arm opposite of the first inner arm;

a first sleeve coupled to the first outer arm by a first suture hole, the first suture hole defined by and extending at least partially through the first distal extent, the first sleeve defining a first channel extending between a proximal end and a distal of the first sleeve along an outer lateral side of the first outer arm opposite the first inner arm, the distal end of the first sleeve forming a closed end; and a second sleeve coupled to the second outer arm by a second suture hole, the second suture hole defined by and extending at least partially through the second distal extent, the second sleeve defining a second channel extending between a proximal end and a distal end of the second sleeve along an outer lateral side of the second outer arm opposite the second inner arm, the distal end of the second sleeve forming a closed end, wherein the second end of the first outer arm is coupled to the second end of the second outer arm at a proximal end of the occlusion device via a hinge portion, and wherein each of the first outer arm, the second outer arm, and the hinge portion define an opening within which the first inner arm and the second inner arm are disposed.

2. The occlusion device of claim 1, wherein the first inner arm includes a first inner surface configured for positioning along a first side of the hollow tissue structure, and the second inner arm includes a second inner surface configured for positioning along a second side of the hollow tissue structure, wherein the first inner surface is arranged parallel to the second inner surface on either side of the central longitudinal axis.

3. The occlusion device of claim 2, wherein the inner surfaces of each of the first and second inner arms comprise a planar surface having a linear profile viewed from a top side or a bottom side of the occlusion device, and wherein the first and second inner arms decrease in width from the second end toward the first end when viewed from the top side or the bottom side of the occlusion device.

4. The occlusion device of claim 1, wherein the hinge portion defines a curved surface that curves inwardly toward the second ends of the first and second inner arms, wherein an end surface at the second ends of each of the first and second inner arms is angled toward the central longitudinal axis at an angle complementary to the curved surface of the hinge portion, and wherein the hinge portion biases the first and second distal extents, including the first ends of the first and second inner arms, inwardly towards the central longitudinal axis.

5. The occlusion device of claim 1, wherein the occlusion device is moveable between: (i) a closed configuration wherein the first end of the first inner arm is spaced apart from the first end of the second inner arm by a first lateral distance, and (ii) an open configuration wherein the first end of the first inner arm is spaced apart from the first end of the second inner arm by a second lateral distance that is greater than the first lateral distance.

6. The occlusion device of claim 5, wherein, in the closed configuration, the first inner arm is substantially parallel to the second inner arm, and, in the open configuration, the first inner arm is angled with respect to the second inner arm.

7. The occlusion device of claim 5, wherein the occlusion device is biased towards the closed configuration.

8. The occlusion device of claim 1, wherein the occlusion device and the central longitudinal axis thereof defines a concave side of the occlusion device and a convex side of the occlusion device opposite from the concave side.

9. The occlusion device of claim 8, wherein the concave side comprises a concave surface having a concave profile viewed from a lateral side of the occlusion device.

10. The occlusion device of claim 1, further comprising:

a third suture hole defined by and extending at least partially through the second end of the first inner arm;

a fourth suture hole defined by and extending at least partially through the second end of the second inner arm;

wherein the second ends of the first and second inner arms each comprise an enlarged head having a width greater than the width of the respective first and second inner arm.

11. The occlusion device of claim 10, further comprising:

a third sleeve defining a third channel, the third sleeve coupled to the third suture hole; and a fourth sleeve defining a fourth channel, the fourth sleeve coupled to the fourth suture hole.

12. The occlusion device of claim 11, wherein each of the first, second, third, and fourth channels are configured to accept a portion of a medical instrument.

13. A method of using an occlusion device, the method comprising:

(1) providing an occlusion device comprising:

a first inner arm extending from a first end to a second end along a first direction parallel to a central longitudinal axis of the occlusion device;

a second inner arm extending from a first end to a second end along the first direction, the second inner arm being adjacent to first inner arm in a second direction that is perpendicular to the central longitudinal axis;

a first outer arm extending from a first end to a second end along the first direction, the first end of the first outer arm being coupled to the first end of the first inner arm to define a first distal extent at a distal end of the occlusion device, wherein the first outer arm is spaced apart from the first inner arm in the second direction on a side of the first inner arm opposite of the second inner arm;

a second outer arm extending from a first end to a second end along the first direction, the first end of the second outer arm being coupled to the first end of the second inner arm to define a second distal extent at the distal end of the occlusion device, wherein the second outer arm is spaced apart from the second inner arm in the second direction on a side of the second inner arm opposite of the first inner arm;

a first sleeve coupled to the first outer arm by a first suture hole defined by and extending at least partially through the first distal extent of the occlusion device, the first sleeve defining a first channel extending between a proximal end and a distal of the first sleeve along an outer lateral side of the first outer arm opposite the first inner arm, the distal end of the first sleeve forming a closed end; and a second sleeve coupled to the second outer arm by a second suture hole defined by and extending at least partially through the second distal extent of the occlusion device, the second sleeve defining a second channel extending between a proximal end and a distal of the second sleeve along an outer lateral side of the second outer arm opposite the second inner arm, the distal end of the second sleeve forming a closed end, wherein the second end of the first outer arm is coupled to the second end of the second outer arm at a proximal end of the occlusion device via a hinge portion, and wherein each of the first outer arm, the second outer arm, and the hinge portion define an opening within which the first inner arm and the second inner arm are disposed;

(2) coupling a first arm of a medical instrument to the first sleeve;

(3) coupling a second arm of the medical instrument to the second sleeve, wherein the second arm of the medical instrument is hingably coupled to the first arm of the medical instrument; and (4) moving the occlusion device from (i) a closed configuration wherein the first end of the first inner arm is spaced apart from the first end of the second inner arm by a first lateral distance, to (ii) an open configuration, wherein the first end of the first inner arm is spaced apart from the first end of the second inner arm by a second lateral distance that is greater than the first lateral distance.

14. The method of claim 13, wherein moving the occlusion device between the closed configuration and the open configuration comprises pivoting the first arm of the medical instrument with respect to the second arm of the medical instrument.

15. The method of claim 13, wherein, in the closed configuration, the first inner arm is substantially parallel to the second inner arm, and, in the open configuration, the first inner arm is angled with respect to the second inner arm.

16. The method of claim 13, further comprising:

coupling the first arm of the medical instrument to a third sleeve defining a third channel, the third sleeve coupled to a third suture hole defined by and extending at least partially through the second end of the first inner arm of the occlusion device; and coupling the second arm of the medical instrument to a fourth sleeve defining a fourth channel, the fourth sleeve coupled to a fourth suture hole defined by and extending at least partially through the second end of the second inner arm of the occlusion device.

17. The method of claim 13, wherein coupling the first arm of the medical instrument to the first sleeve includes inserting a portion of the first arm into the first channel of the first sleeve.

18. The method of claim 17, wherein coupling the second arm of the medical instrument to the second sleeve includes inserting a portion of the second arm into the second channel of the second sleeve.

19. A method for occluding a hollow tissue structure, the method comprising:

(1) moving an occlusion device from a closed configuration to an open configuration, wherein the occlusion device comprises:

a first inner arm extending from a first end to a second end along a first direction parallel to a central longitudinal axis of the occlusion device, the first inner arm having an inner surface and an outer surface opposite the inner surface;

a second inner arm extending from a first end to a second end along the first direction, the second inner arm having an inner surface and an outer surface opposite the inner surface, wherein the second inner arm is adjacent to first inner arm in a second direction that is perpendicular to the central longitudinal axis;

a first outer arm extending from a first end to a second end along the first direction, the first end of the first outer arm being coupled to the first end of the first inner arm to define a first distal extent at a distal end of the occlusion device, wherein the first outer arm is spaced apart from the first inner arm in the second direction on a side of the first inner arm opposite of the second inner arm;

a second outer arm extending from a first end to a second end along the first direction, the first end of the second outer arm being coupled to the first end of the second inner arm to define a second distal extent at the distal end of the occlusion device, wherein the second outer arm is spaced apart from the second inner arm in the second direction on a side of the second inner arm opposite of the first inner arm;

a first sleeve coupled to the first outer arm by a first suture hole, the first suture hole defined by and extending at least partially through the first distal extent, the first sleeve defining a first channel extending between a proximal end and a distal of the first sleeve along an outer lateral side of the first outer arm opposite the first inner arm, the distal end of the first sleeve forming a closed end; and a second sleeve coupled to the second outer arm by a second suture hole, the second suture hole defined by and extending at least partially through the second distal extent, the second sleeve defining a second channel extending between a proximal end and a distal of the second sleeve along an outer lateral side of the second outer arm opposite the second inner arm, the distal end of the second sleeve forming a closed end, wherein the second end of the first outer arm is coupled to the second end of the second outer arm at a proximal end of the occlusion device via a hinge portion, and wherein each of the first outer arm, the second outer arm, and the hinge portion define an opening within which the first inner arm and the second inner arm are disposed, and wherein the occlusion device and the central longitudinal axis thereof defines a concave side of the occlusion device and a convex side of the occlusion device opposite from the concave side;

(2) positioning the occlusion device relative to the hollow tissue structure such that the first inner arm is positioned along a first side of the hollow tissue structure and the second inner arm is positioned along an opposite second side of the hollow tissue structure; and (3) causing the occlusion device to transition from the open configuration toward the closed configuration in which the occlusion device occludes the hollow tissue structure, wherein, when the occlusion device is in the closed configuration, the inner surface of the first inner arm and the inner surface of the second inner arm each face toward the hollow tissue structure.

* * * * *